US012723036B2

(12) United States Patent
Tanaka et al.

(10) Patent No.: US 12,723,036 B2
(45) Date of Patent: Sep. 1, 2026

(54) ARYLTETRAHYDROPYRIDAZINE DERIVATIVE OR SALT THEREOF, INSECTICIDAL AGENT CONTAINING THE COMPOUND, AND METHOD OF USE THEREOF

(71) Applicant: NIHON NOHYAKU CO., LTD., Tokyo (JP)

(72) Inventors: Koji Tanaka, Kawachinagano (JP); Ryosuke Tanaka, Kawachinagano (JP); Shunsuke Matsui, Kawachinagano (JP); Takayuki Yamada, Kawachinagano (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 768 days.

(21) Appl. No.: 18/012,779

(22) PCT Filed: Jun. 24, 2021

(86) PCT No.: PCT/JP2021/023984

§ 371 (c)(1),
(2) Date: Dec. 23, 2022

(87) PCT Pub. No.: WO2021/261563

PCT Pub. Date: Dec. 30, 2021

(65) Prior Publication Data

US 2023/0303522 A1 Sep. 28, 2023

(30) Foreign Application Priority Data

Jun. 26, 2020 (JP) ................................ 2020-110400

(51) Int. Cl.
*C07D 401/14* (2006.01)
*A01N 43/58* (2006.01)
(Continued)

(52) U.S. Cl.
CPC ........... *C07D 401/14* (2013.01); *A01N 43/58* (2013.01); *A01N 43/60* (2013.01); *A01N 43/653* (2013.01); *A01N 43/66* (2013.01); *A01N 43/76* (2013.01); *A01N 43/78* (2013.01); *A01N 43/80* (2013.01); *A01N 43/82* (2013.01); *A01N 43/90* (2013.01);
(Continued)

(58) Field of Classification Search
CPC .. C07D 401/14; C07D 237/24; C07D 401/04; C07D 401/12; C07D 403/04; C07D 403/12; C07D 405/04; C07D 405/12; C07D 405/14; C07D 409/04; C07D 409/14; C07D 413/04; C07D 413/12; C07D 417/04; C07D 417/12; C07D 417/14; C07D 471/04; C07D 513/04; A01N 43/58; A01N 43/60; A01N 43/653; A01N 43/66; A01N 43/76;
(Continued)

(56) References Cited

U.S. PATENT DOCUMENTS 3,976,785 A 8/1976 Diehl et al.
2006/0089499 A1 4/2006 Gebauer et al.
2016/0002251 A1 1/2016 Ohtake et al.

FOREIGN PATENT DOCUMENTS

DE 2213010 A1 * 9/1972 ........... C07D 237/04
EP 2975030 B1 * 7/2020 ........... C07D 237/04
(Continued)

OTHER PUBLICATIONS

STNext, Chemical Abstracts Service, 1,6-dihydro-5-hydroxy-1-methyl-2-phenyl-3(2H)-pyridazinone, (CAS 20335-18-7) CAS Registry File Accessed Sep. 5, 2025 from STN, entered into STN Nov. 16, 1984 (Year: 1984).*

(Continued)

*Primary Examiner* — Andrew D Kosar
*Assistant Examiner* — Jonathan D Mahlum
(74) *Attorney, Agent, or Firm* — Birch, Stewart, Kolasch & Birch, LLP

(57) ABSTRACT

Crop production in agriculture, horticulture, and the like has still been significantly damaged by pests and the like, and pests that are resistant to existing drugs have appeared. Due to such concerns, it is desired to develop novel insecticidal agents and acaricides.

The present invention has found that a compound represented by general formula (1):

[Formula 1]

(1)

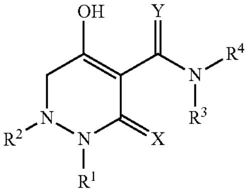

wherein X and Y represent an oxygen atom or a sulfur atom, $R^1$ represents a hydrogen atom or the like, $R^2$ represents a substituted phenyl group or the like, $R^3$ represents a hydrogen atom or the like, and $R^4$ represents a phenyl group or the like, or a salt thereof has a high insecticidal effect on pests in agriculture and horticulture, and the like. The present invention provides an agricultural and horticultural insecticidal agent containing the compound or a salt thereof as an active ingredient, and a method of use thereof.

17 Claims, No Drawings

(51) Int. Cl.

| | |
|---|---|
| ***A01N 43/60*** | (2006.01) |
| ***A01N 43/653*** | (2006.01) |
| ***A01N 43/66*** | (2006.01) |
| ***A01N 43/76*** | (2006.01) |
| ***A01N 43/78*** | (2006.01) |
| ***A01N 43/80*** | (2006.01) |
| ***A01N 43/82*** | (2006.01) |
| ***A01N 43/90*** | (2006.01) |
| ***A01P 7/04*** | (2006.01) |
| ***C07D 237/24*** | (2006.01) |
| ***C07D 401/04*** | (2006.01) |
| ***C07D 401/12*** | (2006.01) |
| ***C07D 403/04*** | (2006.01) |
| ***C07D 403/12*** | (2006.01) |
| ***C07D 405/04*** | (2006.01) |
| ***C07D 405/12*** | (2006.01) |
| ***C07D 405/14*** | (2006.01) |
| ***C07D 409/04*** | (2006.01) |
| ***C07D 409/14*** | (2006.01) |
| ***C07D 413/04*** | (2006.01) |
| ***C07D 413/12*** | (2006.01) |
| ***C07D 417/04*** | (2006.01) |
| ***C07D 417/12*** | (2006.01) |
| ***C07D 417/14*** | (2006.01) |
| ***C07D 471/04*** | (2006.01) |
| ***C07D 513/04*** | (2006.01) |

(52) U.S. Cl.

CPC .............. *A01P 7/04* (2021.08); *C07D 237/24* (2013.01); *C07D 401/04* (2013.01); *C07D 401/12* (2013.01); *C07D 403/04* (2013.01); *C07D 403/12* (2013.01); *C07D 405/04* (2013.01); *C07D 405/12* (2013.01); *C07D 405/14* (2013.01); *C07D 409/04* (2013.01); *C07D 409/14* (2013.01); *C07D 413/04* (2013.01); *C07D 413/12* (2013.01); *C07D 417/04* (2013.01); *C07D 417/12* (2013.01); *C07D 417/14* (2013.01); *C07D 471/04* (2013.01); *C07D 513/04* (2013.01)

(58) Field of Classification Search

CPC ........ A01N 43/78; A01N 43/80; A01N 43/82; A01N 43/90; A01P 7/04

See application file for complete search history.

(56) References Cited

FOREIGN PATENT DOCUMENTS

| | | | | | |
|---|---|---|---|---|---|
| JP | 4-5276 | A | | 1/1992 | |
| JP | 11-152273 | A | | 6/1999 | |
| JP | 2001288173 | A | * | 10/2001 | ........... C07D 237/04 |
| JP | 2005-533070 | A | | 11/2005 | |
| WO | WO 2014/142273 | A1 | | 9/2014 | |

OTHER PUBLICATIONS

Witschel, Bioactive Heterocyclic Compound Classes: Agrochemicals, 2012, 1 ed., Ch. 5 (Year: 2012).*

International Search Report, issued in PCT/JP2021/023984, PCT/ISA/210, dated Sep. 7, 2021.

Written Opinion of the International Searching Authority, issued in PCT/JP2021/023984, PCT/ISA/237, dated Sep. 7, 2021.

Extended European Search Report for European Application No. 21828251.5, dated Jul. 8, 2024.

Colombian Office Action and Search Report for Colombian Application No. NC2023/0000248, dated Mar. 18, 2026.

Gelin, "Synthesis and Reactions of Some 5-Hydroxypyridazinium Hydroxide Inner Salts from 3(2H)- Furanones," J. Org. Chem. , vol. 44, No. 17, 1979, pp. 3053-3057.

* cited by examiner

ARYLTETRAHYDROPYRIDAZINE DERIVATIVE OR SALT THEREOF, INSECTICIDAL AGENT CONTAINING THE COMPOUND, AND METHOD OF USE THEREOF

TECHNICAL FIELD

The present invention relates to an aryltetrahydropyridazine derivative or a salt thereof, and an insecticidal agent containing the compound as an active ingredient, and a method of use thereof.

BACKGROUND ART

Patent Literature 1 describes that certain tetrahydropyridazine-3,5-dione derivatives are useful as pharmaceutical compounds. However, the literature neither discloses nor suggests compounds useful as insecticidal agents.

CITATION LIST

Patent Literature

Patent Literature 1: International Publication No. WO 2014/142273

SUMMARY OF INVENTION

Technical Problem

Crop production in agriculture, horticulture, and the like has still been significantly damaged by pests and the like, and pests that are resistant to existing drugs have appeared. Due to such concerns, it is desired to develop novel insecticidal agents and acaricides.

Solution to Problem

The present inventors have conducted intensive studies to develop novel insecticidal agents, especially agricultural and horticultural insecticidal agents. As a result, the present inventors have found that a compound represented by general formula (1) of the present invention, having an aryltetrahydropyridazine derivative as a carboxylic acid moiety of carboxamide, or a salt thereof exhibits an excellent effect as insecticidal agents, and have completed the present invention.

That is, the present invention relates to the following.

[1]A compound represented by general formula (1):

[Formula 1]

[Formula 1]

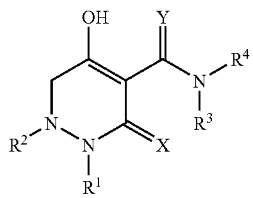

(1)

wherein, $R^1$ represents (a1) a hydrogen atom;

(a2) a $(C_1-C_6)$alkyl group;
(a3) a $(C_2-C_6)$alkenyl group;
(a4) a $(C_2-C_6)$alkynyl group;
(a5) a $(C_3-C_6)$cycloalkyl group;
(a6) a $(C_1-C_6)$alkoxy group;
(a7) a halo$(C_1-C_6)$alkyl group;
(a8) a $(C_1-C_6)$alkylcarbonyl group;
(a9) a $(C_1-C_6)$alkoxycarbonyl group;
(a10) a substituted $(C_1-C_6)$alkyl group having on the chain one to three substituents each independently selected from the group consisting of a cyano group, a $(C_1-C_6)$alkoxy group, and a $(C_3-C_6)$cycloalkyl group;
(a11) a thiazolylmethyl group;
(a12) a substituted thiazolylmethyl group having on the ring one to two substituents each independently selected from the group consisting of a halogen atom, a $(C_1-C_6)$alkyl group, and a $(C_1-C_6)$alkoxy group;
(a13) a benzyl group; or
(a14) a substituted benzyl group having on the ring one to three substituents each independently selected from the group consisting of a halogen atom, a $(C_1-C_6)$alkyl group, and a $(C_1-C_6)$alkoxy group, $R^2$ represents
(b1) an aryl group;
(b2) a substituted aryl group having on the ring one or more substituents each independently selected from substituent group A;
(b3) a 5- to 10-membered ring heterocyclic group; or
(b4) a substituted 5- to 10-membered ring heterocyclic group having on the ring one or more substituents each independently selected from the substituent group A, provided that $R^2$ does not have a substitution with a $(C_1-C_6)$alkylsulfonyl group, a halo$(C_1-C_6)$alkylsulfonyl group, an N— $(C_1-C_6)$alkylaminosulfonyl group, an N,N-di$(C_1-C_6)$alkylaminosulfonyl group, and an $R^6$—($R^7$—N═)O═S group (wherein $R^6$ represents a $(C_1-C_6)$alkyl group, a $(C_3-C_6)$ cycloalkyl group, a halo$(C_1-C_6)$alkyl group, or a $(C_1-C_6)$alkoxy$(C_1-C_6)$ alkyl group, and $R^7$ represents a hydrogen atom, a cyano group, a $(C_1-C_6)$alkyl group, a $(C_3-C_6)$ cycloalkyl group, a halo$(C_1-C_6)$alkyl group, a $(C_2-C_6)$alkylcarbonyl group, or a halo$(C_2-C_6)$alkylcarbonyl group) at an adjacent atom to an atom attached to the tetrahydropyridazine ring, $R^3$ represents
(c1) a hydrogen atom;
(c2) a $(C_1-C_6)$alkyl group;
(c3) a $(C_3-C_6)$cycloalkyl group;
(c4) a $(C_1-C_6)$alkoxy group; or
(c5) a $(C_1-C_6)$alkylcarbonyl group, $R^4$ represents
(d1) a $(C_1-C_6)$alkyl group;
(d2) a $(C_2-C_6)$alkenyl group;
(d3) a $(C_2-C_6)$alkynyl group;
(d4) a $(C_3-C_6)$cycloalkyl group;
(d5) a halo$(C_1-C_6)$alkyl group;
(d6) a halo$(C_2-C_6)$alkenyl group;
(d7) a halo$(C_2-C_6)$alkynyl group;
(d8) a substituted $(C_1-C_6)$alkyl group having one to three substituents each independently selected from substituent group B;
(d9) a substituted $(C_3-C_6)$cycloalkyl group having on the ring one to three substituents each independently selected from substituent group C;
(d10) a $(C_1-C_6)$alkylsulfonyl group;
(d11) an N— $(C_1-C_6)$alkylsulfamoyl group;
(d12) a phenyl group;

(d13) a substituted phenyl group having on the ring one to five substituents each independently selected from substituent group D;
(d14) a phenyl($C_1$-$C_6$)alkyl group;
(d15) a substituted phenyl($C_1$-$C_6$)alkyl group having on the ring one to five substituents each independently selected from the substituent group D;
(d16) a pyridyl group;
(d17) a substituted pyridyl group having on the ring one to four substituents each independently selected from the substituent group D;
(d18) a pyridazinyl group;
(d19) a substituted pyridazinyl group having on the ring one to three substituents each independently selected from the substituent group D;
(d20) a pyrimidinyl group;
(d21) a substituted pyrimidinyl group having on the ring one to three substituents each independently selected from the substituent group D;
(d22) a pyrazinyl group;
(d23) a substituted pyrazinyl group having on the ring one to three substituents each independently selected from the substituent group D;
(d24) a pyrazolyl group;
(d25) a substituted pyrazolyl group having on the ring one to three substituents each independently selected from the substituent group D;
(d26) an isoxazolyl group;
(d27) a substituted isoxazolyl group having on the ring one to two substituents each independently selected from the substituent group D;
(d28) an isothiazolyl group;
(d29) a substituted isothiazolyl group having on the ring one to two substituents each independently selected from the substituent group D;
(d30) an oxazolyl group;
(d31) a substituted oxazolyl group having on the ring one to two substituents each independently selected from the substituent group D;
(d32) a thiazolyl group;
(d33) a substituted thiazolyl group having on the ring one to two substituents each independently selected from the substituent group D;
(d34) a triazolyl group;
(d35) a substituted triazolyl group having on the ring one to two substituents each independently selected from the substituent group D;
(d36) a thiadiazolyl group;
(d37) a substituted thiadiazolyl group having on the ring one substituent each independently selected from the substituent group D;
(d38) a tetrazolyl group;
(d39) a substituted tetrazolyl group having on the ring one substituent each independently selected from the substituent group D;
(d40) a triazinyl group;
(d41) a substituted triazinyl group having on the ring one to two substituents each independently selected from the substituent group D;
(d42) a furyl($C_1$-$C_6$)alkyl group;
(d43) a substituted furyl($C_1$-$C_6$)alkyl group having on the ring one to three substituents each independently selected from the substituent group D;
(d44) a thienyl($C_1$-$C_6$)alkyl group;
(d45) a substituted thienyl($C_1$-$C_6$)alkyl group having on the ring one to three substituents each independently selected from the substituent group D;
(d46) a quinolinyl group;
(d47) a substituted quinolinyl group having on the ring one to six substituents each independently selected from the substituent group D;
(d48) a benzothiazolyl group;
(d49) a substituted benzothiazolyl group having on the ring one to four substituents each independently selected from the substituent group D;
(d50) a pyridyl($C_1$-$C_6$)alkyl group;
(d51) a substituted pyridyl($C_1$-$C_6$)alkyl group having on the ring one to four substituents each independently selected from the substituent group D;
(d52) a pyrazinyl($C_1$-$C_6$)alkyl group;
(d53) a substituted pyrazinyl($C_1$-$C_6$)alkyl group having on the ring one to three substituents each independently selected from the substituent group D;
(d54) a naphthyl group;
(d55) a substituted naphthyl group having on the ring one to seven substituents each independently selected from the substituent group D;
(d56) a tetrahydronaphthyl group; or
(d57) a substituted tetrahydronaphthyl group having on the ring one to ten substituents each independently selected from the substituent group D, X and Y each independently represent an oxygen atom or a sulfur atom, the substituent group A consists of
(e1) a halogen atom;
(e2) a cyano group;
(e3) a nitro group;
(e4) a hydroxyl group;
(e5) a carboxyl group;
(e6) a ($C_1$-$C_6$)alkyl group;
(e7) a ($C_2$-$C_6$)alkenyl group;
(e8) a ($C_2$-$C_6$)alkynyl group;
(e9) a ($C_1$-$C_6$)alkoxy group;
(e10) a ($C_3$-$C_6$)cycloalkyl group;
(e11) a ($C_1$-$C_6$)alkylthio group;
(e12) a ($C_1$-$C_6$)alkylsulfinyl group;
(e13) a ($C_1$-$C_6$)alkylsulfonyl group;
(e14) a halo($C_1$-$C_6$)alkyl group;
(e15) a halo($C_2$-$C_6$)alkenyl group;
(e16) a halo($C_2$-$C_6$)alkynyl group;
(e17) a halo($C_1$-$C_6$)alkoxy group;
(e18) a halo($C_3$-$C_6$) cycloalkyl group;
(e19) a halo($C_1$-$C_6$)alkylthio group;
(e20) a halo($C_1$-$C_6$)alkylsulfinyl group;
(e21) a halo($C_1$-$C_6$)alkylsulfonyl group;
(e22) a ($C_1$-$C_6$)alkylcarbonylamino group;
(e23) a halo($C_1$-$C_6$)alkylcarbonylamino group;
(e24) a ($C_1$-$C_6$)alkylsulfonylamino group;
(e25) a halo($C_1$-$C_6$)alkylsulfonylamino group;
(e26) an $SF_5$ group;
(e27) a ($C_1$-$C_6$)alkoxy($C_1$-$C_6$)alkyl group;
(e28) an N— ($C_1$-$C_6$)alkylcarboxamide group;
(e29) an N-halo($C_1$-$C_6$)alkylcarboxamide group;
(e30) an oxadiazolyl group;
(e31) a substituted oxadiazolyl group having on the ring one substituent each independently selected from the group consisting of a halogen atom, a cyano group, a ($C_1$-$C_6$)alkyl group, a ($C_1$-$C_6$)alkoxy group, a ($C_3$-$C_6$) cycloalkyl group, a ($C_1$-$C_6$)alkylthio group, a ($C_1$-$C_6$) alkylsulfinyl group, a ($C_1$-$C_6$)alkylsulfonyl group, a halo($C_1$-$C_6$)alkyl group, and a halo($C_1$-$C_6$)alkoxy group;
(e32) a ($C_1$-$C_6$)alkoxycarbonyl group;

(e33) a methylenedioxy group formed by two adjacent substituents, wherein the methylenedioxy group is optionally substituted with one to two substituents selected from the group consisting of a halogen atom, a phenyl group, and a $(C_1-C_6)$alkyl group;

(e34) an N— $(C_1-C_6)$alkylaminosulfonyl group;

(e35) an N,N-di$(C_1-C_6)$alkylaminosulfonyl group;

(e36) an $R^6$—($R^7$—N═)O═S group, wherein $R^6$ represents a $(C_1-C_6)$alkyl group, a $(C_3-C_6)$ cycloalkyl group, a halo$(C_1-C_6)$alkyl group, or a $(C_1-C_6)$alkoxy $(C_1-C_6)$ alkyl group, and $R^7$ represents a hydrogen atom, a cyano group, a $(C_1-C_6)$alkyl group, a $(C_3-C_6)$ cycloalkyl group, a halo$(C_1-C_6)$alkyl group, a $(C_2-C_6)$alkylcarbonyl group, or a halo$(C_2-C_6)$alkylcarbonyl group; and (e37) a substituted $(C_3-C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group, the substituent group B consists of (f1) a cyano group;

(f2) a $(C_3-C_6)$cycloalkyl group;

(f3) a $(C_1-C_6)$alkoxy group;

(f4) a $(C_1-C_6)$alkylthio group;

(f5) a $(C_1-C_6)$alkylsulfinyl group;

(f6) a $(C_1-C_6)$alkylsulfonyl group;

(f7) a halo$(C_3-C_6)$ cycloalkyl group;

(f8) a halo$(C_1-C_6)$alkoxy group;

(f9) a halo$(C_1-C_6)$alkylthio group;

(f10) a halo$(C_1-C_6)$alkylsulfinyl group;

(f11) a halo$(C_1-C_6)$alkylsulfonyl group;

(f12) a carboxamide group; and (f13) a phenylcarbonyl group, the substituent group C consists of (g1) a cyano group;

(g2) a $(C_1-C_6)$alkyl group;

(g3) a $(C_3-C_6)$cycloalkyl group;

(g4) a $(C_1-C_6)$alkoxy group;

(g5) a $(C_1-C_6)$alkylthio group;

(g6) a $(C_1-C_6)$alkylsulfinyl group;

(g7) a $(C_1-C_6)$alkylsulfonyl group;

(g8) a halo$(C_3-C_6)$ cycloalkyl group;

(g9) a halo$(C_1-C_6)$alkoxy group;

(g10) a halo$(C_1-C_6)$alkylthio group;

(g11) a halo$(C_1-C_6)$alkylsulfinyl group;

(g12) a halo$(C_1-C_6)$alkylsulfonyl group;

(g13) a halo$(C_1-C_6)$alkyl group;

(g14) a carboxamide group;

(g15) a $(C_2-C_6)$alkynyl group; and (g16) a phenyl group, the substituent group D consists of (h1) a halogen atom;

(h2) a cyano group;

(h3) a hydroxyl group;

(h4) a carboxyl group;

(h5) a $(C_1-C_6)$alkyl group;

(h6) a $(C_1-C_6)$alkoxy group;

(h7) a $(C_3-C_6)$cycloalkyl group;

(h8) a $(C_1-C_6)$alkylthio group;

(h9) a $(C_1-C_6)$alkylsulfinyl group;

(h10) a $(C_1-C_6)$alkylsulfonyl group;

(h11) a halo$(C_1-C_6)$alkyl group;

(h12) a halo$(C_3-C_6)$alkoxy group;

(h13) a halo$(C_1-C_6)$ cycloalkyl group;

(h14) a halo$(C_1-C_6)$alkylthio group;

(h15) a halo$(C_1-C_6)$alkylsulfinyl group;

(h116) a halo$(C_1-C_6)$alkylsulfonyl group;

(h17) a $(C_1-C_6)$alkoxycarbonyl group;

(h18) an N— $(C_1-C_6)$alkylcarboxamide group;

(h19) an N-halo$(C_1-C_6)$alkylcarboxamide group;

(h20) a methylenedioxy group formed by two adjacent substituents, wherein the methylenedioxy group is optionally substituted with one to two substituents selected from the group consisting of a halogen atom, a phenyl group, and a $(C_1-C_6)$alkyl group;

(h21) a nitro group;

(h22) an amino group; and (h23) a benzyloxycarbonyl group, and a salt thereof.

[2] The compound and a salt thereof according to [1], wherein $R^1$, $R^3$, $R^4$, X, Y, and the substituent groups A, B, C, and D are as defined in [1], and $R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b15) a furyl group;

(b16) a substituted furyl group having on the ring one to three substituents each independently selected from the substituent group A;

(b17) a thienyl group;

(b18) a substituted thienyl group having on the ring one to three substituents each independently selected from the substituent group A;

(b19) an isoxazolyl group;

(b20) a substituted isoxazolyl group having on the ring one to two substituents each independently selected from the substituent group A;

(b21) an oxazolyl group;

(b22) a substituted oxazolyl group having on the ring one to two substituents each independently selected from the substituent group A;

(b23) a pyrazolyl group;

(b24) a substituted pyrazolyl group having on the ring one to three substituents each independently selected from the substituent group A;

(b25) an imidazolyl group;

(b26) a substituted imidazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b31) an isothiazolyl group;

(b32) a substituted isothiazolyl group having on the ring one to two substituents each independently selected from the substituent group A;

(b33) a thiadiazolyl group;

(b34) a substituted thiadiazolyl group having on the ring one substituent each independently selected from the substituent group A;

(b35) an imidazopyridyl group;

(b36) a substituted imidazopyridyl group having on the ring one to five substituents each independently selected from the substituent group A;

(b37) a quinoxalinyl group;

(b38) a substituted quinoxalinyl group having on the ring one to five substituents each independently selected from the substituent group A;

(b39) a benzoxazolyl group;

(b40) a substituted benzoxazolyl group having on the ring one to four substituents each independently selected from the substituent group A;

(b41) a benzimidazolyl group;

(b42) a substituted benzimidazolyl group having on the ring one to five substituents each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group;

(b48) a substituted quinolinyl group having on the ring one to six substituents each independently selected from the substituent group A;

(b49) a naphthyl group;

(b50) a substituted naphthyl group having on the ring one to seven substituents each independently selected from the substituent group A;

(b51) a triazinyl group;

(b52) a substituted triazinyl group having on the ring one to two substituents each independently selected from the substituent group A;

(b53) a pyrrolyl group;

(b54) a substituted pyrrolyl group having on the ring one to four substituents each independently selected from the substituent group A;

(b55) a tetrazolyl group;

(b56) a substituted tetrazolyl group having on the ring one substituent each independently selected from the substituent group A;

(b57) an oxadiazonyl group;

(b58) a substituted oxadiazonyl group having on the ring one substituent each independently selected from the substituent group A;

(b59) a 2-oxopyridyl group;

(b60) a substituted 2-oxopyridyl group having on the ring one to four substituents each independently selected from the substituent group A;

(b61) a benzofuranyl group;

(b62) a substituted benzofuranyl group having on the ring one to five substituents each independently selected from the substituent group A;

(b63) a benzisoxazolyl group;

(b64) a substituted benzisoxazolyl group having on the ring one to four substituents each independently selected from the substituent group A;

(b65) a benzothienyl group;

(b66) a substituted benzothienyl group having on the ring one to five substituents each independently selected from the substituent group A;

(b67) a benzisothiazolyl group;

(b68) a substituted benzisothiazolyl group having on the ring one to four substituents each independently selected from the substituent group A;

(b69) an indolyl group;

(b70) a substituted indolyl group having on the ring one to six substituents each independently selected from the substituent group A;

(b71) an isoindolyl group;

(b72) a substituted isoindolyl group having on the ring one to six substituents each independently selected from the substituent group A;

(b73) an indazolyl group;

(b74) a substituted indazolyl group having on the ring one to five substituents each independently selected from the substituent group A;

(b75) a benzotriazolyl group;

(b76) a substituted benzotriazolyl group having on the ring one to four substituents each independently selected from the substituent group A;

(b77) a furopyridyl group;

(b78) a substituted furopyridyl group having on the ring one to four substituents each independently selected from the substituent group A;

(b79) a thienopyridyl group;

(b80) a substituted thienopyridyl group having on the ring one to four substituents each independently selected from the substituent group A;

(b81) an indolizinyl group;

(b82) a substituted indolizinyl group having on the ring one to six substituents each independently selected from the substituent group A;

(b83) a pyrrolopyridyl group;

(b84) a substituted pyrrolopyridyl group having on the ring one to five substituents each independently selected from the substituent group A;

(b85) a pyrrolopyrimidinyl group;

(b86) a substituted pyrrolopyrimidinyl group having on the ring one to five substituents each independently selected from the substituent group A;

(b87) an oxazolopyridyl group;

(b88) a substituted oxazolopyridyl group having on the ring one to three substituents each independently selected from the substituent group A;

(b89) an isoxazolopyridyl group;

(b90) a substituted isoxazolopyridyl group having on the ring one to three substituents each independently selected from the substituent group A;

(b91) an isothiazolopyridyl group;

(b92) a substituted isothiazolopyridyl group having on the ring one to three substituents each independently selected from the substituent group A;

(b93) an imidazopyrimidinyl group;

(b94) a substituted imidazopyrimidinyl group having on the ring one to five substituents each independently selected from the substituent group A;

(b95) a pyrazolopyridyl group;

(b96) a substituted pyrazolopyridyl group having on the ring one to five substituents each independently selected from the substituent group A;
(b97) a pyrazolopyrimidinyl group;
(b98) a substituted pyrazolopyrimidinyl group having on the ring one to five substituents each independently selected from the substituent group A;
(b99) a triazolopyridyl group;
(b100) a substituted triazolopyridyl group having on the ring one to four substituents each independently selected from the substituent group A;
(b101) a triazolopyrimidinyl group;
(b102) a substituted triazolopyrimidinyl group having on the ring one to four substituents each independently selected from the substituent group A;
(b103) an isoquinolinyl group;
(b104) a substituted isoquinolinyl group having on the ring one to six substituents each independently selected from the substituent group A;
(b105) a cinnolinyl group;
(b106) a substituted cinnolinyl group having on the ring one to five substituents each independently selected from the substituent group A;
(b107) a phthalazinyl group;
(b108) a substituted phthalazinyl group having on the ring one to five substituents each independently selected from the substituent group A;
(b109) a quinazolinyl group;
(b110) a substituted quinazolinyl group having on the ring one to five substituents each independently selected from the substituent group A; (bill) a naphthyridinyl group; or
(b112) a substituted naphthyridinyl group having on the ring one to five substituents each independently selected from the substituent group A.

[3] The compound and a salt thereof according to [1] or [2], wherein
$R^1$ represents
(a1) a hydrogen atom;
(a2) a $(C_1\text{-}C_6)$alkyl group; or
(a4) a $(C_2\text{-}C_6)$alkynyl group,
$R^2$ represents
(b5) a phenyl group;
(b6) a substituted phenyl group having on the ring one to five substituents each independently selected from the substituent group A;
(b7) a pyridyl group;
(b8) a substituted pyridyl group having on the ring one to four substituents each independently selected from the substituent group A;
(b9) a pyridazinyl group;
(b10) a substituted pyridazinyl group having on the ring one to three substituents each independently selected from the substituent group A;
(b11) a pyrimidinyl group;
(b12) a substituted pyrimidinyl group having on the ring one to three substituents each independently selected from the substituent group A;
(b13) a pyrazinyl group;
(b14) a substituted pyrazinyl group having on the ring one to three substituents each independently selected from the substituent group A;
(b15) a furyl group;
(b16) a substituted furyl group having on the ring one to three substituents each independently selected from the substituent group A;
(b17) a thienyl group;
(b18) a substituted thienyl group having on the ring one to three substituents each independently selected from the substituent group A;
(b19) an isoxazolyl group;
(b20) a substituted isoxazolyl group having on the ring one to two substituents each independently selected from the substituent group A;
(b21) an oxazolyl group;
(b22) a substituted oxazolyl group having on the ring one to two substituents each independently selected from the substituent group A;
(b23) a pyrazolyl group;
(b24) a substituted pyrazolyl group having on the ring one to three substituents each independently selected from the substituent group A;
(b25) an imidazolyl group;
(b26) a substituted imidazolyl group having on the ring one to three substituents each independently selected from the substituent group A;
(b27) a triazolyl group;
(b28) a substituted triazolyl group having on the ring one to two substituents each independently selected from the substituent group A;
(b29) a thiazolyl group;
(b30) a substituted thiazolyl group having on the ring one to two substituents each independently selected from the substituent group A;
(b31) an isothiazolyl group;
(b32) a substituted isothiazolyl group having on the ring one to two substituents each independently selected from the substituent group A;
(b33) a thiadiazolyl group;
(b34) a substituted thiadiazolyl group having on the ring one substituent each independently selected from the substituent group A;
(b35) an imidazopyridyl group;
(b36) a substituted imidazopyridyl group having on the ring one to five substituents each independently selected from the substituent group A;
(b37) a quinoxalinyl group;
(b38) a substituted quinoxalinyl group having on the ring one to five substituents each independently selected from the substituent group A;
(b39) a benzoxazolyl group;
(b40) a substituted benzoxazolyl group having on the ring one to four substituents each independently selected from the substituent group A;
(b41) a benzimidazolyl group;
(b42) a substituted benzimidazolyl group having on the ring one to five substituents each independently selected from the substituent group A;
(b43) a benzothiazolyl group;
(b44) a substituted benzothiazolyl group having on the ring one to four substituents each independently selected from the substituent group A;
(b45) a thiazolopyridyl group;
(b46) a substituted thiazolopyridyl group having on the ring one to four substituents each independently selected from the substituent group A;
(b47) a quinolinyl group; or
(b48) a substituted quinolinyl group having on the ring one to six substituents each independently selected from the substituent group A,
$R^3$ represents
(c1) a hydrogen atom; or
(c2) a $(C_1\text{-}C_6)$alkyl group, $R^4$ represents (d1) a $(C_2-C_6)$alkyl group;

(d2) a $(C_2-C_6)$alkenyl group;

(d3) a $(C_2-C_6)$alkynyl group;

(d4) a $(C_3-C_6)$cycloalkyl group;

(d5) a halo$(C_1-C_6)$alkyl group;

(d8) a substituted $(C_1-C_6)$alkyl group having one to three substituents each independently selected from the substituent group B;

(d9) a substituted $(C_3-C_6)$cycloalkyl group having on the ring one to three substituents each independently selected from the substituent group C;

(d10) a $(C_1-C_6)$alkylsulfonyl group;

(d11) an N— $(C_1-C_6)$alkylsulfamoyl group;

(d12) a phenyl group;

(d13) a substituted phenyl group having on the ring one to five substituents each independently selected from the substituent group D;

(d14) a phenyl$(C_1-C_6)$alkyl group;

(d15) a substituted phenyl$(C_1-C_6)$alkyl group having on the ring one to five substituents each independently selected from the substituent group D;

(d16) a pyridyl group;

(d17) a substituted pyridyl group having on the ring one to four substituents each independently selected from the substituent group D;

(d18) a pyridazinyl group;

(d19) a substituted pyridazinyl group having on the ring one to three substituents each independently selected from the substituent group D;

(d20) a pyrimidinyl group;

(d21) a substituted pyrimidinyl group having on the ring one to three substituents each independently selected from the substituent group D;

(d22) a pyrazinyl group;

(d23) a substituted pyrazinyl group having on the ring one to three substituents each independently selected from the substituent group D;

(d24) a pyrazolyl group;

(d25) a substituted pyrazolyl group having on the ring one to three substituents each independently selected from the substituent group D;

(d26) an isoxazolyl group;

(d27) a substituted isoxazolyl group having on the ring one to two substituents each independently selected from the substituent group D;

(d28) an isothiazolyl group;

(d29) a substituted isothiazolyl group having on the ring one to two substituents each independently selected from the substituent group D;

(d30) an oxazolyl group;

(d31) a substituted oxazolyl group having on the ring one to two substituents each independently selected from the substituent group D;

(d32) a thiazolyl group;

(d33) a substituted thiazolyl group having on the ring one to two substituents each independently selected from the substituent group D;

(d34) a triazolyl group;

(d35) a substituted triazolyl group having on the ring one to two substituents each independently selected from the substituent group D;

(d36) a thiadiazolyl group;

(d37) a substituted thiadiazolyl group having on the ring one substituent each independently selected from the substituent group D;

(d38) a tetrazolyl group;

(d39) a substituted tetrazolyl group having on the ring one substituent each independently selected from the substituent group D;

(d40) a triazinyl group;

(d41) a substituted triazinyl group having on the ring one to two substituents each independently selected from the substituent group D;

(d42) a furyl$(C_1-C_6)$alkyl group;

(d43) a substituted furyl$(C_1-C_6)$alkyl group having on the ring one to three substituents each independently selected from the substituent group D;

(d44) a thienyl$(C_1-C_6)$alkyl group;

(d45) a substituted thienyl$(C_1-C_6)$alkyl group having on the ring one to three substituents each independently selected from the substituent group D;

(d46) a quinolinyl group;

(d47) a substituted quinolinyl group having on the ring one to six substituents each independently selected from the substituent group D;

(d48) a benzothiazolyl group;

(d49) a substituted benzothiazolyl group having on the ring one to four substituents each independently selected from the substituent group D;

(d50) a pyridyl$(C_1-C_6)$alkyl group;

(d51) a substituted pyridyl$(C_1-C_6)$alkyl group having on the ring one to four substituents each independently selected from the substituent group D;

(d52) a pyrazinyl$(C_1-C_6)$alkyl group;

(d53) a substituted pyrazinyl$(C_1-C_6)$alkyl group having on the ring one to three substituents each independently selected from the substituent group D;

(d54) a naphthyl group;

(d55) a substituted naphthyl group having on the ring one to seven substituents each independently selected from the substituent group D;

(d56) a tetrahydronaphthyl group; or (d57) a substituted tetrahydronaphthyl group having on the ring one to ten substituents each independently selected from the substituent group D, the substituent group A consists of (e1) a halogen atom;

(e2) a cyano group;

(e4) a hydroxyl group;

(e5) a carboxyl group;

(e6) a $(C_1-C_6)$alkyl group;

(e9) a $(C_1-C_6)$alkoxy group;

(e10) a $(C_3-C_6)$cycloalkyl group;

(e11) a $(C_1-C_6)$alkylthio group;

(e12) a $(C_1-C_6)$alkylsulfinyl group;

(e13) a $(C_1-C_6)$alkylsulfonyl group;

(e14) a halo$(C_1-C_6)$alkyl group;

(e17) a halo$(C_1-C_6)$alkoxy group;

(e18) a halo$(C_3-C_6)$ cycloalkyl group;

(e19) a halo$(C_1-C_6)$alkylthio group;

(e20) a halo$(C_1-C_6)$alkylsulfinyl group;

(e21) a halo$(C_1-C_6)$alkylsulfonyl group;

(e22) a $(C_1-C_6)$alkylcarbonylamino group;

(e24) a $(C_1-C_6)$alkylsulfonylamino group;

(e28) an N— $(C_1-C_6)$alkylcarboxamide group;

(e30) an oxadiazolyl group;

(e31) a substituted oxadiazolyl group having on the ring one substituent each independently selected from the group consisting of a halogen atom, a cyano group, a $(C_1-C_6)$alkyl group, a $(C_1-C_6)$alkoxy group, a $(C_3-C_6)$ cycloalkyl group, a $(C_1-C_6)$alkylthio group, a $(C_1-C_6)$ alkylsulfinyl group, a $(C_1-C_6)$alkylsulfonyl group, a halo$(C_1-C_6)$alkyl group, and a halo$(C_1-C_6)$alkoxy group;

(e32) a $(C_1-C_6)$alkoxycarbonyl group;

(e33) a methylenedioxy group formed by two adjacent substituents, wherein the methylenedioxy group is optionally substituted with one or two substituents selected from the group consisting of a halogen atom, a phenyl group, and a $(C_1-C_6)$alkyl group;

(e34) an N— $(C_1-C_6)$alkylaminosulfonyl group;

(e35) an N,N-di$(C_1-C_6)$alkylaminosulfonyl group;

(e36) an $R^6$—($R^7$—N═)O═S group, wherein $R^6$ represents a $(C_1-C_6)$alkyl group, a $(C_3-C_6)$ cycloalkyl group, a halo$(C_1-C_6)$alkyl group, or a $(C_1-C_6)$alkoxy $(C_1-C_6)$ alkyl group, and $R^7$ represents a hydrogen atom, a cyano group, a $(C_1-C_6)$alkyl group, a $(C_3-C_6)$ cycloalkyl group, a halo$(C_1-C_6)$alkyl group, a $(C_2-C_6)$alkylcarbonyl group, or a halo$(C_2-C_6)$alkylcarbonyl group; and (e37) a substituted $(C_3-C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group, the substituent group B consists of (f1) a cyano group;

(f2) a $(C_3-C_6)$cycloalkyl group;

(f3) a $(C_1-C_6)$alkoxy group;

(f4) a $(C_1-C_6)$alkylthio group;

(f5) a $(C_1-C_6)$alkylsulfinyl group;

(f6) a $(C_1-C_6)$alkylsulfonyl group;

(f7) a halo$(C_3-C_6)$ cycloalkyl group;

(f8) a halo$(C_1-C_6)$alkoxy group;

(f9) a halo$(C_1-C_6)$alkylthio group;

(f10) a halo$(C_1-C_6)$alkylsulfinyl group; and (f11) a halo$(C_1-C_6)$alkylsulfonyl group, the substituent group C consists of (g1) a cyano group;

(g2) a $(C_1-C_6)$alkyl group;

(g3) a $(C_3-C_6)$cycloalkyl group;

(g4) a $(C_1-C_6)$alkoxy group;

(g5) a $(C_1-C_6)$alkylthio group;

(g6) a $(C_1-C_6)$alkylsulfinyl group;

(g7) a $(C_1-C_6)$alkylsulfonyl group;

(g8) a halo$(C_3-C_6)$ cycloalkyl group;

(g9) a halo$(C_1-C_6)$alkoxy group;

(g10) a halo$(C_1-C_6)$alkylthio group;

(g11) a halo$(C_1-C_6)$alkylsulfinyl group;

(g12) a halo$(C_1-C_6)$alkylsulfonyl group;

(g13) a halo$(C_1-C_6)$alkyl group;

(g15) a $(C_2-C_6)$alkynyl group; and (g16) a phenyl group, and the substituent group D consists of (h1) a halogen atom;

(h2) a cyano group;

(h3) a hydroxyl group;

(h4) a carboxyl group;

(h5) a $(C_1-C_6)$alkyl group;

(h6) a $(C_1-C_6)$alkoxy group;

(h7) a $(C_3-C_6)$cycloalkyl group;

(h8) a $(C_1-C_6)$alkylthio group;

(h9) a $(C_1-C_6)$alkylsulfinyl group;

(h10) a $(C_1-C_6)$alkylsulfonyl group;

(h11) a halo$(C_1-C_6)$alkyl group;

(h12) a halo$(C_1-C_6)$alkoxy group;

(h13) a halo$(C_3-C_6)$ cycloalkyl group;

(h14) a halo$(C_1-C_6)$alkylthio group;

(h15) a halo$(C_1-C_6)$alkylsulfinyl group;

(h16) a halo$(C_1-C_6)$alkylsulfonyl group;

(h17) a $(C_1-C_6)$alkoxycarbonyl group;

(h18) an N— $(C_1-C_6)$alkylcarboxamide group;

(h20) a methylenedioxy group formed by two adjacent substituents, wherein the methylenedioxy group is optionally substituted with one or two substituents selected from the group consisting of a halogen atom, a phenyl group, and a $(C_1-C_6)$alkyl group;

(h21) a nitro group;

(h22) an amino group; and (h23) a benzyloxycarbonyl group.

[4] The compound and a salt thereof according to any one of [1] to [3], wherein $R^1$ is (a1) a hydrogen atom;

$R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b23) a pyrazolyl group;

(b24) a substituted pyrazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b33) a thiadiazolyl group;

(b34) a substituted thiadiazolyl group having on the ring one substituent each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group; or (b48) a substituted quinolinyl group having on the ring one to six substituents each independently selected from the substituent group A, $R^3$ represents (c1) a hydrogen atom; or (c2) a $(C_1-C_6)$alkyl group, $R^4$ represents
(d1) a ($C_2$-$C_6$)alkyl group;
(d2) a ($C_2$-$C_6$)alkenyl group;
(d3) a ($C_2$-$C_6$)alkynyl group;
(d4) a ($C_3$-$C_6$)cycloalkyl group;
(d5) a halo($C_1$-$C_6$)alkyl group;
(d8) a substituted ($C_1$-$C_6$)alkyl group having one to three substituents each independently selected from the substituent group B;
(d9) a substituted ($C_3$-$C_6$)cycloalkyl group having on the ring one to three substituents each independently selected from the substituent group C;
(d12) a phenyl group;
(d13) a substituted phenyl group having on the ring one to five substituents each independently selected from the substituent group D;
(d14) a phenyl($C_1$-$C_6$)alkyl group;
(d15) a substituted phenyl($C_1$-$C_6$)alkyl group having on the ring one to five substituents each independently selected from the substituent group D;
(d16) a pyridyl group;
(d17) a substituted pyridyl group having on the ring one to four substituents each independently selected from the substituent group D;
(d18) a pyridazinyl group;
(d19) a substituted pyridazinyl group having on the ring one to three substituents each independently selected from the substituent group D;
(d20) a pyrimidinyl group;
(d21) a substituted pyrimidinyl group having on the ring one to three substituents each independently selected from the substituent group D;
(d22) a pyrazinyl group;
(d24) a pyrazolyl group;
(d25) a substituted pyrazolyl group having on the ring one to three substituents each independently selected from the substituent group D;
(d26) an isoxazolyl group;
(d27) a substituted isoxazolyl group having on the ring one to two substituents each independently selected from the substituent group D;
(d32) a thiazolyl group;
(d33) a substituted thiazolyl group having on the ring one to two substituents each independently selected from the substituent group D;
(d34) a triazolyl group;
(d35) a substituted triazolyl group having on the ring one to two substituents each independently selected from the substituent group D;
(d36) a thiadiazolyl group;
(d37) a substituted thiadiazolyl group having on the ring one substituent each independently selected from the substituent group D;
(d42) a furyl($C_1$-$C_6$)alkyl group;
(d43) a substituted furyl($C_1$-$C_6$)alkyl group having on the ring one to three substituents each independently selected from the substituent group D;
(d44) a thienyl($C_1$-$C_6$)alkyl group;
(d45) a substituted thienyl($C_1$-$C_6$)alkyl group having on the ring one to three substituents each independently selected from the substituent group D;
(d46) a quinolinyl group;
(d47) a substituted quinolinyl group having on the ring one to six substituents each independently selected from the substituent group D;
(d48) a benzothiazolyl group;
(d49) a substituted benzothiazolyl group having on the ring one to four substituents each independently selected from the substituent group D;
(d50) a pyridyl($C_1$-$C_6$)alkyl group;
(d51) a substituted pyridyl($C_1$-$C_6$)alkyl group having on the ring one to four substituents each independently selected from the substituent group D;
(d52) a pyrazinyl($C_1$-$C_6$)alkyl group;
(d53) a substituted pyrazinyl($C_1$-$C_6$)alkyl group having on the ring one to three substituents each independently selected from the substituent group D;
(d54) a naphthyl group;
(d55) a substituted naphthyl group having on the ring one to seven substituents each independently selected from the substituent group D;
(d56) a tetrahydronaphthyl group; or
(d57) a substituted tetrahydronaphthyl group having on the ring one to ten substituents each independently selected from the substituent group D, the substituent group A consists of
(e1) a halogen atom;
(e2) a cyano group;
(e6) a ($C_1$-$C_6$)alkyl group;
(e9) a ($C_1$-$C_6$)alkoxy group;
(e11) a ($C_1$-$C_6$)alkylthio group;
(e12) a ($C_1$-$C_6$)alkylsulfinyl group;
(e13) a ($C_1$-$C_6$)alkylsulfonyl group;
(e14) a halo($C_1$-$C_6$)alkyl group;
(e17) a halo($C_1$-$C_6$)alkoxy group;
(e19) a halo($C_1$-$C_6$)alkylthio group;
(e21) a halo($C_1$-$C_6$)alkylsulfonyl group;
(e32) a ($C_1$-$C_6$)alkoxycarbonyl group;
(e34) an N—($C_1$-$C_6$)alkylaminosulfonyl group; and
(e35) an N,N-di($C_1$-$C_6$)alkylaminosulfonyl group;
the substituent group B consists of
(f1) a cyano group;
(f2) a ($C_3$-$C_6$)cycloalkyl group;
(f3) a ($C_1$-$C_6$)alkoxy group; and
(f4) a ($C_1$-$C_6$)alkylthio group;
the substituent group C consists of
(g1) a cyano group;
(g2) a ($C_1$-$C_6$)alkyl group;
(g13) a halo($C_1$-$C_6$)alkyl group;
(g15) a ($C_2$-$C_6$)alkynyl group; and
(g16) a phenyl group,
the substituent group D consists of
(h1) a halogen atom;
(h2) a cyano group;
(h3) a hydroxyl group;
(h5) a ($C_1$-$C_6$)alkyl group;
(h6) a ($C_1$-$C_6$)alkoxy group;
(h8) a ($C_1$-$C_6$)alkylthio group;
(h11) a halo($C_1$-$C_6$)alkyl group;
(h12) a halo($C_1$-$C_6$)alkoxy group;
(h17) a ($C_1$-$C_6$)alkoxycarbonyl group;
(h20) a methylenedioxy group formed by two adjacent substituents, wherein the methylenedioxy group is optionally substituted with one or two substituents selected from the group consisting of a halogen atom, a phenyl group, and a ($C_1$-$C_6$)alkyl group; and
(h21) a nitro group.
[5] An insecticidal agent containing the compound or a salt thereof according to any one of [1] to [4] or an N-oxide as an active ingredient.

[6] An agricultural and horticultural insecticidal agent containing the compound or a salt thereof according to any one of [1] to [4] or an N-oxide as an active ingredient.

[7] An animal ectoparasite control agent containing the compound or a salt thereof according to any one of [1] to [4] or an N-oxide as an active ingredient.

[8] An animal endoparasite control agent containing the compound or a salt thereof according to any one of [1] to [4] or an N-oxide as an active ingredient.

[9]A method of using an insecticidal agent, including applying an effective amount of the insecticidal agent according to [5] or [6] to a plant or soil.

[10] Use of the compound or a salt thereof according to any one of [1] to [4] or an N-oxide as an insecticidal agent.

[11]A compound represented by general formula (13A):

[Formula 2]

(13A)

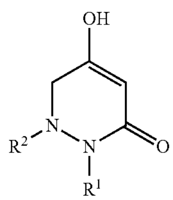

wherein, $R^1$ represents (a1) a hydrogen atom;
(a2) a $(C_1-C_6)$alkyl group;
(a3) a $(C_2-C_6)$alkenyl group;
(a4) a $(C_2-C_6)$alkynyl group;
(a5) a $(C_3-C_6)$cycloalkyl group;
(a6) a $(C_1-C_6)$alkoxy group;
(a7) a halo$(C_1-C_6)$alkyl group;
(a8) a $(C_1-C_6)$alkylcarbonyl group;
(a9) a $(C_1-C_6)$alkoxycarbonyl group;
(a10) a substituted $(C_1-C_6)$alkyl group having on the chain one to three substituents each independently selected from the group consisting of a cyano group, a $(C_1-C_6)$alkoxy group, and a $(C_3-C_6)$cycloalkyl group;
(a11) a thiazolylmethyl group;
(a12) a substituted thiazolylmethyl group having on the ring one or two substituents each independently selected from the group consisting of a halogen atom, a $(C_1-C_6)$alkyl group, and a $(C_1-C_6)$alkoxy group;
(a13) a benzyl group; or
(a14) a substituted benzyl group having on the ring one to three substituents each independently selected from the group consisting of a halogen atom, a $(C_1-C_6)$alkyl group, and a $(C_1-C_6)$alkoxy group, $R^2$ represents (b1) an aryl group;
(b2) a substituted aryl group having on the ring one or more substituents each independently selected from substituent group A;
(b3) a 5- to 10-membered ring heterocyclic group; or
(b4) a substituted 5- to 10-membered ring heterocyclic group having on the ring one or more substituents each independently selected from the substituent group A, provided that $R^2$ does not have a substitution with a $(C_1-C_6)$alkylsulfonyl group, a halo$(C_1-C_6)$alkylsulfonyl group, an N— $(C_1-C_6)$alkylaminosulfonyl group, an N,N-di$(C_1-C_6)$alkylaminosulfonyl group, and an $R^6$—($R^7$—N═)O═S group (wherein $R^6$ represents a $(C_1-C_6)$alkyl group, a $(C_3-C_6)$ cycloalkyl group, a halo$(C_1-C_6)$alkyl group, or a $(C_1-C_6)$alkoxy$(C_1-C_6)$ alkyl group, and $R^7$ represents a hydrogen atom, a cyano group, a $(C_1-C_6)$alkyl group, a $(C_3-C_6)$ cycloalkyl group, a halo$(C_1-C_6)$alkyl group, a $(C_2-C_6)$alkylcarbonyl group, or a halo$(C_2-C_6)$alkylcarbonyl group) at an adjacent atom to an atom attached to the tetrahydropyridazine ring, the substituent group A consists of (e1) a halogen atom;
(e2) a cyano group;
(e3) a nitro group;
(e4) a hydroxyl group;
(e5) a carboxyl group;
(e6) a $(C_1-C_6)$alkyl group;
(e7) a $(C_2-C_6)$alkenyl group;
(e8) a $(C_2-C_6)$alkynyl group;
(e9) a $(C_1-C_6)$alkoxy group;
(e10) a $(C_3-C_6)$cycloalkyl group;
(e11) a $(C_1-C_6)$alkylthio group;
(e12) a $(C_1-C_6)$alkylsulfinyl group;
(e13) a $(C_1-C_6)$alkylsulfonyl group;
(e14) a halo$(C_2-C_6)$alkyl group;
(e15) a halo$(C_2-C_6)$alkenyl group;
(e16) a halo$(C_2-C_6)$alkynyl group;
(e17) a halo$(C_3-C_6)$alkoxy group;
(e18) a halo$(C_1-C_6)$ cycloalkyl group;
(e29) a halo$(C_1-C_6)$alkylthio group;
(e20) a halo$(C_1-C_6)$alkylsulfinyl group;
(e22) a halo$(C_1-C_6)$alkylsulfonyl group;
(e22) a $(C_1-C_6)$alkylcarbonylamino group;
(e23) a halo$(C_1-C_6)$alkylcarbonylamino group;
(e24) a $(C_1-C_6)$alkylsulfonylamino group;
(e25) a halo$(C_1-C_6)$alkylsulfonylamino group;
(e26) an $SF_5$ group;
(e27) a $(C_1-C_6)$alkoxy$(C_1-C_6)$alkyl group;
(e28) an N— $(C_1-C_6)$alkylcarboxamide group;
(e29) an N-halo$(C_1-C_6)$alkylcarboxamide group;
(e30) an oxadiazolyl group;
(e31) a substituted oxadiazolyl group having on the ring one substituent each independently selected from the group consisting of a halogen atom, a cyano group, a $(C_1-C_6)$alkyl group, a $(C_1-C_6)$alkoxy group, a $(C_3-C_6)$ cycloalkyl group, a $(C_1-C_6)$alkylthio group, a $(C_1-C_6)$ alkylsulfinyl group, a $(C_1-C_6)$alkylsulfonyl group, a halo$(C_1-C_6)$alkyl group, and a halo$(C_1-C_6)$alkoxy group;
(e32) a $(C_1-C_6)$alkoxycarbonyl group;
(e33) a methylenedioxy group formed by two adjacent substituents, wherein the methylenedioxy group is optionally substituted with one or two substituents selected from the group consisting of a halogen atom, a phenyl group, and a $(C_1-C_6)$alkyl group;
(e34) an N— $(C_1-C_6)$alkylaminosulfonyl group;
(e35) an N,N-di$(C_1-C_6)$alkylaminosulfonyl group;
(e36) an $R^6$—($R^7$—N═)O═S group, wherein $R^6$ represents a $(C_1-C_6)$alkyl group, a $(C_3-C_6)$ cycloalkyl group, a halo$(C_1-C_6)$alkyl group, or a $(C_1-C_6)$alkoxy $(C_1-C_6)$ alkyl group, and $R^7$ represents a hydrogen atom, a cyano group, a $(C_1-C_6)$alkyl group, a $(C_3-C_6)$ cycloalkyl group, a halo$(C_1-C_6)$alkyl group, a $(C_2-C_6)$alkylcarbonyl group, or a halo$(C_2-C_6)$alkylcarbonyl group; and
(e37) a substituted $(C_3-C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group, and a salt thereof.

[12] The compound and a salt thereof according to [11], wherein $R^1$ and the substituent group A are as defined in [11], and $R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b15) a furyl group;

(b16) a substituted furyl group having on the ring one to three substituents each independently selected from the substituent group A;

(b17) a thienyl group;

(b18) a substituted thienyl group having on the ring one to three substituents each independently selected from the substituent group A;

(b19) an isoxazolyl group;

(b20) a substituted isoxazolyl group having on the ring one to two substituents each independently selected from the substituent group A;

(b21) an oxazolyl group;

(b22) a substituted oxazolyl group having on the ring one to two substituents each independently selected from the substituent group A;

(b23) a pyrazolyl group;

(b24) a substituted pyrazolyl group having on the ring one to three substituents each independently selected from the substituent group A;

(b25) an imidazolyl group;

(b26) a substituted imidazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b31) an isothiazolyl group;

(b32) a substituted isothiazolyl group having on the ring one to two substituents each independently selected from the substituent group A;

(b33) a thiadiazolyl group;

(b34) a substituted thiadiazolyl group having on the ring one substituent each independently selected from the substituent group A;

(b35) an imidazopyridyl group;

(b36) a substituted imidazopyridyl group having on the ring one to five substituents each independently selected from the substituent group A;

(b37) a quinoxalinyl group;

(b38) a substituted quinoxalinyl group having on the ring one to five substituents each independently selected from the substituent group A;

(b39) a benzoxazolyl group;

(b40) a substituted benzoxazolyl group having on the ring one to four substituents each independently selected from the substituent group A;

(b41) a benzimidazolyl group;

(b42) a substituted benzimidazolyl group having on the ring one to five substituents each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group;

(b48) a substituted quinolinyl group having on the ring one to six substituents each independently selected from the substituent group A;

(b49) a naphthyl group;

(b50) a substituted naphthyl group having on the ring one to seven substituents each independently selected from the substituent group A;

(b51) a triazinyl group;

(b52) a substituted triazinyl group having on the ring one to two substituents each independently selected from the substituent group A;

(b53) a pyrrolyl group;

(b54) a substituted pyrrolyl group having on the ring one to four substituents each independently selected from the substituent group A;

(b55) a tetrazolyl group;

(b56) a substituted tetrazolyl group having on the ring one substituent each independently selected from the substituent group A;

(b57) an oxadiazonyl group;

(b58) a substituted oxadiazonyl group having on the ring one substituent each independently selected from the substituent group A;

(b59) a 2-oxopyridyl group;

(b60) a substituted 2-oxopyridyl group having on the ring one to four substituents each independently selected from the substituent group A;

(b61) a benzofuranyl group;

(b62) a substituted benzofuranyl group having on the ring one to five substituents each independently selected from the substituent group A;

(b63) a benzisoxazolyl group;

(b64) a substituted benzisoxazolyl group having on the ring one to four substituents each independently selected from the substituent group A;

(b65) a benzothienyl group;

(b66) a substituted benzothienyl group having on the ring one to five substituents each independently selected from the substituent group A;

(b67) a benzisothiazolyl group;
(b68) a substituted benzisothiazolyl group having on the ring one to four substituents each independently selected from the substituent group A;
(b69) an indolyl group;
(b70) a substituted indolyl group having on the ring one to six substituents each independently selected from the substituent group A;
(b71) an isoindolyl group;
(b72) a substituted isoindolyl group having on the ring one to six substituents each independently selected from the substituent group A;
(b73) an indazolyl group;
(b74) a substituted indazolyl group having on the ring one to five substituents each independently selected from the substituent group A;
(b75) a benzotriazolyl group;
(b76) a substituted benzotriazolyl group having on the ring one to four substituents each independently selected from the substituent group A;
(b77) a furopyridyl group;
(b78) a substituted furopyridyl group having on the ring one to four substituents each independently selected from the substituent group A;
(b79) a thienopyridyl group;
(b80) a substituted thienopyridyl group having on the ring one to four substituents each independently selected from the substituent group A;
(b81) an indolizinyl group;
(b82) a substituted indolizinyl group having on the ring one to six substituents each independently selected from the substituent group A;
(b83) a pyrrolopyridyl group;
(b84) a substituted pyrrolopyridyl group having on the ring one to five substituents each independently selected from the substituent group A;
(b85) a pyrrolopyrimidinyl group;
(b86) a substituted pyrrolopyrimidinyl group having on the ring one to five substituents each independently selected from the substituent group A;
(b87) an oxazolopyridyl group;
(b88) a substituted oxazolopyridyl group having on the ring one to three substituents each independently selected from the substituent group A;
(b89) an isoxazolopyridyl group;
(b90) a substituted isoxazolopyridyl group having on the ring one to three substituents each independently selected from the substituent group A;
(b91) an isothiazolopyridyl group;
(b92) a substituted isothiazolopyridyl group having on the ring one to three substituents each independently selected from the substituent group A;
(b93) an imidazopyrimidinyl group;
(b94) a substituted imidazopyrimidinyl group having on the ring one to five substituents each independently selected from the substituent group A;
(b95) a pyrazolopyridyl group;
(b96) a substituted pyrazolopyridyl group having on the ring one to five substituents each independently selected from the substituent group A;
(b97) a pyrazolopyrimidinyl group;
(b98) a substituted pyrazolopyrimidinyl group having on the ring one to five substituents each independently selected from the substituent group A;
(b99) a triazolopyridyl group;
(b100) a substituted triazolopyridyl group having on the ring one to four substituents each independently selected from the substituent group A;
(b101) a triazolopyrimidinyl group;
(b102) a substituted triazolopyrimidinyl group having on the ring one to four substituents each independently selected from the substituent group A;
(b103) an isoquinolinyl group;
(b104) a substituted isoquinolinyl group having on the ring one to six substituents each independently selected from the substituent group A;
(b105) a cinnolinyl group;
(b106) a substituted cinnolinyl group having on the ring one to five substituents each independently selected from the substituent group A;
(b107) a phthalazinyl group;
(b108) a substituted phthalazinyl group having on the ring one to five substituents each independently selected from the substituent group A;
(b109) a quinazolinyl group;
(b110) a substituted quinazolinyl group having on the ring one to five substituents each independently selected from the substituent group A;
(b111) a naphthyridinyl group; or
(b112) a substituted naphthyridinyl group having on the ring one to five substituents each independently selected from the substituent group A.

[13] The compound and a salt thereof according to [11] or [12], wherein $R^1$ represents
(a1) a hydrogen atom;
(a2) a $(C_1-C_6)$alkyl group; or
(a4) a $(C_2-C_6)$alkynyl group, $R^2$ represents
(b5) a phenyl group;
(b6) a substituted phenyl group having on the ring one to five substituents each independently selected from the substituent group A;
(b7) a pyridyl group;
(b8) a substituted pyridyl group having on the ring one to four substituents each independently selected from the substituent group A;
(b9) a pyridazinyl group;
(b10) a substituted pyridazinyl group having on the ring one to three substituents each independently selected from the substituent group A;
(b11) a pyrimidinyl group;
(b12) a substituted pyrimidinyl group having on the ring one to three substituents each independently selected from the substituent group A;
(b13) a pyrazinyl group;
(b14) a substituted pyrazinyl group having on the ring one to three substituents each independently selected from the substituent group A;
(b15) a furyl group;
(b16) a substituted furyl group having on the ring one to three substituents each independently selected from the substituent group A;
(b17) a thienyl group;
(b18) a substituted thienyl group having on the ring one to three substituents each independently selected from the substituent group A;
(b19) an isoxazolyl group;
(b20) a substituted isoxazolyl group having on the ring one to two substituents each independently selected from the substituent group A;
(b21) an oxazolyl group;

(b22) a substituted oxazolyl group having on the ring one to two substituents each independently selected from the substituent group A;

(b23) a pyrazolyl group;

(b24) a substituted pyrazolyl group having on the ring one to three substituents each independently selected from the substituent group A;

(b25) an imidazolyl group;

(b26) a substituted imidazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b31) an isothiazolyl group;

(b32) a substituted isothiazolyl group having on the ring one to two substituents each independently selected from the substituent group A;

(b33) a thiadiazolyl group;

(b34) a substituted thiadiazolyl group having on the ring one substituent each independently selected from the substituent group A;

(b35) an imidazopyridyl group;

(b36) a substituted imidazopyridyl group having on the ring one to five substituents each independently selected from the substituent group A;

(b37) a quinoxalinyl group;

(b38) a substituted quinoxalinyl group having on the ring one to five substituents each independently selected from the substituent group A;

(b39) a benzoxazolyl group;

(b40) a substituted benzoxazolyl group having on the ring one to four substituents each independently selected from the substituent group A;

(b41) a benzimidazolyl group;

(b42) a substituted benzimidazolyl group having on the ring one to five substituents each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group; or (b48) a substituted quinolinyl group having on the ring one to six substituents each independently selected from the substituent group A, the substituent group A consists of (e1) a halogen atom;

(e2) a cyano group;

(e4) a hydroxyl group;

(e5) a carboxyl group;

(e6) a $(C_1-C_6)$alkyl group;

(e9) a $(C_1-C_6)$alkoxy group;

(e10) a $(C_3-C_6)$cycloalkyl group;

(e11) a $(C_1-C_6)$alkylthio group;

(e12) a $(C_1-C_6)$alkylsulfinyl group;

(e13) a $(C_1-C_6)$alkylsulfonyl group;

(e14) a halo$(C_1-C_6)$alkyl group;

(e17) a halo$(C_1-C_6)$alkoxy group;

(e18) a halo$(C_3-C_6)$ cycloalkyl group;

(e19) a halo$(C_1-C_6)$alkylthio group;

(e20) a halo$(C_1-C_6)$alkylsulfinyl group;

(e21) a halo$(C_1-C_6)$alkylsulfonyl group;

(e22) a $(C_1-C_6)$alkylcarbonylamino group;

(e24) a $(C_1-C_6)$alkylsulfonylamino group;

(e28) an N— $(C_1-C_6)$alkylcarboxamide group;

(e30) an oxadiazolyl group;

(e31) a substituted oxadiazolyl group having on the ring one substituent each independently selected from the group consisting of a halogen atom, a cyano group, a $(C_1-C_6)$alkyl group, a $(C_1-C_6)$alkoxy group, a $(C_3-C_6)$ cycloalkyl group, a $(C_1-C_6)$alkylthio group, a $(C_1-C_6)$ alkylsulfinyl group, a $(C_1-C_6)$alkylsulfonyl group, a halo$(C_1-C_6)$alkyl group, and a halo$(C_1-C_6)$alkoxy group;

(e32) a $(C_1-C_6)$alkoxycarbonyl group;

(e33) a methylenedioxy group formed by two adjacent substituents, wherein the methylenedioxy group is optionally substituted with one or two substituents selected from the group consisting of a halogen atom, a phenyl group, and a $(C_1-C_6)$alkyl group;

(e34) an N— $(C_1-C_6)$alkylaminosulfonyl group;

(e35) an N,N-di$(C_1-C_6)$alkylaminosulfonyl group;

(e36) an $R^6$—$(R^7$—N=)O=S group, wherein $R^6$ represents a $(C_1-C_6)$alkyl group, a $(C_3-C_6)$ cycloalkyl group, a halo$(C_1-C_6)$alkyl group, or a $(C_1-C_6)$alkoxy $(C_1-C_6)$ alkyl group, and $R^7$ represents a hydrogen atom, a cyano group, a $(C_1-C_6)$alkyl group, a $(C_3-C_6)$ cycloalkyl group, a halo$(C_1-C_6)$alkyl group, a $(C_2-C_6)$alkylcarbonyl group, or a halo$(C_2-C_6)$alkylcarbonyl group; and (e37) a substituted $(C_3-C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group.

[14] The compound and a salt thereof according to any one of [11] to [13], wherein $R^1$ is (a1) a hydrogen atom;

$R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b23) a pyrazolyl group;

(b24) a substituted pyrazolyl group having on the ring one to three substituents each independently selected from the substituent group A;

(b27) a triazolyl group;

(b28) a substituted triazolyl group having on the ring one to two substituents each independently selected from the substituent group A;
(b29) a thiazolyl group;
(b30) a substituted thiazolyl group having on the ring one to two substituents each independently selected from the substituent group A;
(b33) a thiadiazolyl group;
(b34) a substituted thiadiazolyl group having on the ring one substituent each independently selected from the substituent group A;
(b43) a benzothiazolyl group;
(b44) a substituted benzothiazolyl group having on the ring one to four substituents each independently selected from the substituent group A;
(b45) a thiazolopyridyl group;
(b46) a substituted thiazolopyridyl group having on the ring one to four substituents each independently selected from the substituent group A;
(b47) a quinolinyl group; or
(b48) a substituted quinolinyl group having on the ring one to six substituents each independently selected from the substituent group A, and
the substituent group A consists of
(e1) a halogen atom;
(e2) a cyano group;
(e6) a $(C_1-C_6)$alkyl group;
(e9) a $(C_1-C_6)$alkoxy group;
(e11) a $(C_1-C_6)$alkylthio group;
(e12) a $(C_1-C_6)$alkylsulfinyl group;
(e13) a $(C_1-C_6)$alkylsulfonyl group;
(e14) a halo$(C_1-C_6)$alkyl group;
(e17) a halo$(C_1-C_6)$alkoxy group;
(e19) a halo$(C_1-C_6)$alkylthio group;
(e21) a halo$(C_1-C_6)$alkylsulfonyl group;
(e32) a $(C_1-C_6)$alkoxycarbonyl group;
(e34) an N—$(C_1-C_6)$alkylaminosulfonyl group; and
(e35) an N,N-di$(C_1-C_6)$alkylaminosulfonyl group.

[15]A compound represented by general formula (3A):

[Formula 3]

(3A)

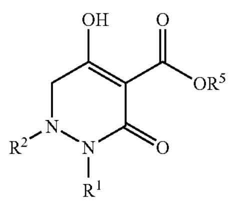

wherein,
$R^1$ represents
(a1) a hydrogen atom;
(a2) a $(C_1-C_6)$alkyl group;
(a3) a $(C_2-C_6)$alkenyl group;
(a4) a $(C_2-C_6)$alkynyl group;
(a5) a $(C_3-C_6)$cycloalkyl group;
(a6) a $(C_1-C_6)$alkoxy group;
(a7) a halo$(C_1-C_6)$alkyl group;
(a8) a $(C_1-C_6)$alkylcarbonyl group;
(a9) a $(C_1-C_6)$alkoxycarbonyl group;
(a10) a substituted $(C_1-C_6)$alkyl group having on the chain one to three substituents each independently selected from the group consisting of a cyano group, a $(C_1-C_6)$alkoxy group, and a $(C_3-C_6)$cycloalkyl group;
(a11) a thiazolylmethyl group;
(a12) a substituted thiazolylmethyl group having on the ring one to two substituents each independently selected from the group consisting of a halogen atom, a $(C_1-C_6)$alkyl group, and a $(C_1-C_6)$alkoxy group;
(a13) a benzyl group; or
(a14) a substituted benzyl group having on the ring one to three substituents each independently selected from the group consisting of a halogen atom, a $(C_1-C_6)$alkyl group, and a $(C_1-C_6)$alkoxy group,
$R^2$ represents
(b1) an aryl group;
(b2) a substituted aryl group having on the ring one or more substituents each independently selected from substituent group A;
(b3) a 5- to 10-membered ring heterocyclic group; or
(b4) a substituted 5- to 10-membered ring heterocyclic group having on the ring one or more substituents each independently selected from the substituent group A, provided that $R^2$ does not have a substitution with a $(C_1-C_6)$alkylsulfonyl group, a halo$(C_1-C_6)$alkylsulfonyl group, an N— $(C_1-C_6)$alkylaminosulfonyl group, an N,N-di$(C_1-C_6)$alkylaminosulfonyl group, and an $R^6$—$(R^7$—N=)O=S group (wherein $R^6$ represents a $(C_1-C_6)$alkyl group, a $(C_3-C_6)$ cycloalkyl group, a halo$(C_1-C_6)$alkyl group, or a $(C_1-C_6)$alkoxy$(C_1-C_6)$ alkyl group, and $R^7$ represents a hydrogen atom, a cyano group, a $(C_1-C_6)$alkyl group, a $(C_3-C_6)$ cycloalkyl group, a halo$(C_1-C_6)$alkyl group, a $(C_2-C_6)$alkylcarbonyl group, or a halo$(C_2-C_6)$alkylcarbonyl group) at an adjacent atom to an atom attached to the tetrahydropyridazine ring,
$R^5$ represents
(i1) a $(C_1-C_6)$alkyl group; or
(i2) a $(C_1-C_6)$alkoxy$(C_1-C_6)$alkyl group, and
the substituent group A consists of
(e1) a halogen atom;
(e2) a cyano group;
(e3) a nitro group;
(e4) a hydroxyl group;
(e5) a carboxyl group;
(e6) a $(C_1-C_6)$alkyl group;
(e7) a $(C_2-C_6)$alkenyl group;
(e8) a $(C_2-C_6)$alkynyl group;
(e9) a $(C_1-C_6)$alkoxy group;
(e10) a $(C_3-C_6)$cycloalkyl group;
(e11) a $(C_1-C_6)$alkylthio group;
(e12) a $(C_1-C_6)$alkylsulfinyl group;
(e13) a $(C_1-C_6)$alkylsulfonyl group;
(e14) a halo$(C_1-C_6)$alkyl group;
(e15) a halo$(C_2-C_6)$alkenyl group;
(e16) a halo$(C_2-C_6)$alkynyl group;
(e17) a halo$(C_1-C_6)$alkoxy group;
(e18) a halo$(C_1-C_6)$ cycloalkyl group;
(e29) a halo$(C_1-C_6)$alkylthio group;
(e20) a halo$(C_1-C_6)$alkylsulfinyl group;
(e22) a halo$(C_1-C_6)$alkylsulfonyl group;
(e22) a $(C_1-C_6)$alkylcarbonylamino group;
(e23) a halo$(C_1-C_6)$alkylcarbonylamino group;
(e24) a $(C_1-C_6)$alkylsulfonylamino group;
(e25) a halo$(C_1-C_6)$alkylsulfonylamino group;
(e26) an $SF_5$ group;
(e27) a $(C_1-C_6)$alkoxy$(C_1-C_6)$alkyl group;
(e28) an N— $(C_1-C_6)$alkylcarboxamide group;
(e29) an N-halo$(C_1-C_6)$alkylcarboxamide group;
(e30) an oxadiazolyl group;

(e31) a substituted oxadiazolyl group having on the ring one substituent each independently selected from the group consisting of a halogen atom, a cyano group, a $(C_1-C_6)$alkyl group, a $(C_1-C_6)$alkoxy group, a $(C_3-C_6)$ cycloalkyl group, a $(C_1-C_6)$alkylthio group, a $(C_1-C_6)$ alkylsulfinyl group, a $(C_1-C_6)$alkylsulfonyl group, a halo$(C_1-C_6)$alkyl group, and a halo$(C_1-C_6)$alkoxy group;

(e32) a $(C_1-C_6)$alkoxycarbonyl group;

(e33) a methylenedioxy group formed by two adjacent substituents, wherein the methylenedioxy group is optionally substituted with one or two substituents selected from the group consisting of a halogen atom, a phenyl group, and a $(C_1-C_6)$alkyl group;

(e34) an N— $(C_1-C_6)$alkylaminosulfonyl group;

(e35) an N,N-di$(C_1-C_6)$alkylaminosulfonyl group;

(e36) an $R^6$—$(R^7$—N=)O=S group, wherein $R^6$ represents a $(C_1-C_6)$alkyl group, a $(C_3-C_6)$ cycloalkyl group, a halo$(C_1-C_6)$alkyl group, or a $(C_1-C_6)$alkoxy $(C_1-C_6)$ alkyl group, and $R^7$ represents a hydrogen atom, a cyano group, a $(C_1-C_6)$ alkyl group, a $(C_3-C_6)$ cycloalkyl group, a halo$(C_1-C_6)$ alkyl group, a $(C_2-C_6)$alkylcarbonyl group, or a halo $(C_2-C_6)$alkylcarbonyl group; and (e37) a substituted $(C_3-C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group, and a salt thereof.

[16] The compound and a salt thereof according to [15], wherein $R^1$, $R^5$, and the substituent group A are as defined in [15], and $R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b15) a furyl group;

(b16) a substituted furyl group having on the ring one to three substituents each independently selected from the substituent group A;

(b17) a thienyl group;

(b18) a substituted thienyl group having on the ring one to three substituents each independently selected from the substituent group A;

(b19) an isoxazolyl group;

(b20) a substituted isoxazolyl group having on the ring one to two substituents each independently selected from the substituent group A;

(b21) an oxazolyl group;

(b22) a substituted oxazolyl group having on the ring one to two substituents each independently selected from the substituent group A;

(b23) a pyrazolyl group;

(b24) a substituted pyrazolyl group having on the ring one to three substituents each independently selected from the substituent group A;

(b25) an imidazolyl group;

(b26) a substituted imidazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b31) an isothiazolyl group;

(b32) a substituted isothiazolyl group having on the ring one to two substituents each independently selected from the substituent group A;

(b33) a thiadiazolyl group;

(b34) a substituted thiadiazolyl group having on the ring one substituent each independently selected from the substituent group A;

(b35) an imidazopyridyl group;

(b36) a substituted imidazopyridyl group having on the ring one to five substituents each independently selected from the substituent group A;

(b37) a quinoxalinyl group;

(b38) a substituted quinoxalinyl group having on the ring one to five substituents each independently selected from the substituent group A;

(b39) a benzoxazolyl group;

(b40) a substituted benzoxazolyl group having on the ring one to four substituents each independently selected from the substituent group A;

(b41) a benzimidazolyl group;

(b42) a substituted benzimidazolyl group having on the ring one to five substituents each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group;

(b48) a substituted quinolinyl group having on the ring one to six substituents each independently selected from the substituent group A;

(b49) a naphthyl group;

(b50) a substituted naphthyl group having on the ring one to seven substituents each independently selected from the substituent group A;

(b51) a triazinyl group;

(b52) a substituted triazinyl group having on the ring one to two substituents each independently selected from the substituent group A;

(b53) a pyrrolyl group;

(b54) a substituted pyrrolyl group having on the ring one to four substituents each independently selected from the substituent group A;
(b55) a tetrazolyl group;
(b56) a substituted tetrazolyl group having on the ring one substituent each independently selected from the substituent group A;
(b57) an oxadiazonyl group;
(b58) a substituted oxadiazonyl group having on the ring one substituent each independently selected from the substituent group A;
(b59) a 2-oxopyridyl group;
(b60) a substituted 2-oxopyridyl group having on the ring one to four substituents each independently selected from the substituent group A;
(b61) a benzofuranyl group;
(b62) a substituted benzofuranyl group having on the ring one to five substituents each independently selected from the substituent group A;
(b63) a benzisoxazolyl group;
(b64) a substituted benzisoxazolyl group having on the ring one to four substituents each independently selected from the substituent group A;
(b65) a benzothienyl group;
(b66) a substituted benzothienyl group having on the ring one to five substituents each independently selected from the substituent group A;
(b67) a benzisothiazolyl group;
(b68) a substituted benzisothiazolyl group having on the ring one to four substituents each independently selected from the substituent group A;
(b69) an indolyl group;
(b70) a substituted indolyl group having on the ring one to six substituents each independently selected from the substituent group A;
(b71) an isoindolyl group;
(b72) a substituted isoindolyl group having on the ring one to six substituents each independently selected from the substituent group A;
(b73) an indazolyl group;
(b74) a substituted indazolyl group having on the ring one to five substituents each independently selected from the substituent group A;
(b75) a benzotriazolyl group;
(b76) a substituted benzotriazolyl group having on the ring one to four substituents each independently selected from the substituent group A;
(b77) a furopyridyl group;
(b78) a substituted furopyridyl group having on the ring one to four substituents each independently selected from the substituent group A;
(b79) a thienopyridyl group;
(b80) a substituted thienopyridyl group having on the ring one to four substituents each independently selected from the substituent group A;
(b81) an indolizinyl group;
(b82) a substituted indolizinyl group having on the ring one to six substituents each independently selected from the substituent group A;
(b83) a pyrrolopyridyl group;
(b84) a substituted pyrrolopyridyl group having on the ring one to five substituents each independently selected from the substituent group A;
(b85) a pyrrolopyrimidinyl group;
(b86) a substituted pyrrolopyrimidinyl group having on the ring one to five substituents each independently selected from the substituent group A;
(b87) an oxazolopyridyl group;
(b88) a substituted oxazolopyridyl group having on the ring one to three substituents each independently selected from the substituent group A;
(b89) an isoxazolopyridyl group;
(b90) a substituted isoxazolopyridyl group having on the ring one to three substituents each independently selected from the substituent group A;
(b91) an isothiazolopyridyl group;
(b92) a substituted isothiazolopyridyl group having on the ring one to three substituents each independently selected from the substituent group A;
(b93) an imidazopyrimidinyl group;
(b94) a substituted imidazopyrimidinyl group having on the ring one to five substituents each independently selected from the substituent group A;
(b95) a pyrazolopyridyl group;
(b96) a substituted pyrazolopyridyl group having on the ring one to five substituents each independently selected from the substituent group A;
(b97) a pyrazolopyrimidinyl group;
(b98) a substituted pyrazolopyrimidinyl group having on the ring one to five substituents each independently selected from the substituent group A;
(b99) a triazolopyridyl group;
(b100) a substituted triazolopyridyl group having on the ring one to four substituents each independently selected from the substituent group A;
(b101) a triazolopyrimidinyl group;
(b102) a substituted triazolopyrimidinyl group having on the ring one to four substituents each independently selected from the substituent group A;
(b103) an isoquinolinyl group;
(b104) a substituted isoquinolinyl group having on the ring one to six substituents each independently selected from the substituent group A;
(b105) a cinnolinyl group;
(b106) a substituted cinnolinyl group having on the ring one to five substituents each independently selected from the substituent group A;
(b107) a phthalazinyl group;
(b108) a substituted phthalazinyl group having on the ring one to five substituents each independently selected from the substituent group A;
(b109) a quinazolinyl group;
(b110) a substituted quinazolinyl group having on the ring one to five substituents each independently selected from the substituent group A; (bill) a naphthyridinyl group; or
(b112) a substituted naphthyridinyl group having on the ring one to five substituents each independently selected from the substituent group A.

[17] The compound and a salt thereof according to [15] or [16], wherein
$R^1$ represents
(a1) a hydrogen atom;
(a2) a $(C_1-C_6)$alkyl group; or
(a4) a $(C_2-C_6)$alkynyl group;
$R^2$ represents
(b5) a phenyl group;
(b6) a substituted phenyl group having on the ring one to five substituents each independently selected from the substituent group A;
(b7) a pyridyl group;
(b8) a substituted pyridyl group having on the ring one to four substituents each independently selected from the substituent group A;

(b9) a pyridazinyl group;
(b10) a substituted pyridazinyl group having on the ring one to three substituents each independently selected from the substituent group A;
(b11) a pyrimidinyl group;
(b12) a substituted pyrimidinyl group having on the ring one to three substituents each independently selected from the substituent group A;
(b13) a pyrazinyl group;
(b14) a substituted pyrazinyl group having on the ring one to three substituents each independently selected from the substituent group A;
(b15) a furyl group;
(b16) a substituted furyl group having on the ring one to three substituents each independently selected from the substituent group A;
(b17) a thienyl group;
(b18) a substituted thienyl group having on the ring one to three substituents each independently selected from the substituent group A;
(b19) an isoxazolyl group;
(b20) a substituted isoxazolyl group having on the ring one to two substituents each independently selected from the substituent group A;
(b21) an oxazolyl group;
(b22) a substituted oxazolyl group having on the ring one to two substituents each independently selected from the substituent group A;
(b23) a pyrazolyl group;
(b24) a substituted pyrazolyl group having on the ring one to three substituents each independently selected from the substituent group A;
(b25) an imidazolyl group;
(b26) a substituted imidazolyl group having on the ring one to three substituents each independently selected from the substituent group A;
(b27) a triazolyl group;
(b28) a substituted triazolyl group having on the ring one to two substituents each independently selected from the substituent group A;
(b29) a thiazolyl group;
(b30) a substituted thiazolyl group having on the ring one to two substituents each independently selected from the substituent group A;
(b31) an isothiazolyl group;
(b32) a substituted isothiazolyl group having on the ring one to two substituents each independently selected from the substituent group A;
(b33) a thiadiazolyl group;
(b34) a substituted thiadiazolyl group having on the ring one substituent each independently selected from the substituent group A;
(b35) an imidazopyridyl group;
(b36) a substituted imidazopyridyl group having on the ring one to five substituents each independently selected from the substituent group A;
(b37) a quinoxalinyl group;
(b38) a substituted quinoxalinyl group having on the ring one to five substituents each independently selected from the substituent group A;
(b39) a benzoxazolyl group;
(b40) a substituted benzoxazolyl group having on the ring one to four substituents each independently selected from the substituent group A;
(b41) a benzimidazolyl group;
(b42) a substituted benzimidazolyl group having on the ring one to five substituents each independently selected from the substituent group A;
(b43) a benzothiazolyl group;
(b44) a substituted benzothiazolyl group having on the ring one to four substituents each independently selected from the substituent group A;
(b45) a thiazolopyridyl group;
(b46) a substituted thiazolopyridyl group having on the ring one to four substituents each independently selected from the substituent group A;
(b47) a quinolinyl group; or
(b48) a substituted quinolinyl group having on the ring one to six substituents each independently selected from the substituent group A,
$R^3$ represents
(i1) a $(C_1\text{-}C_6)$alkyl group; or
(i2) a $(C_1\text{-}C_6)$alkoxy$(C_1\text{-}C_6)$alkyl group, and
the substituent group A consists of
(e1) a halogen atom;
(e2) a cyano group;
(e4) a hydroxyl group;
(e5) a carboxyl group;
(e6) a $(C_1\text{-}C_6)$alkyl group;
(e9) a $(C_1\text{-}C_6)$alkoxy group;
(e10) a $(C_3\text{-}C_6)$cycloalkyl group;
(e11) a $(C_1\text{-}C_6)$alkylthio group;
(e12) a $(C_1\text{-}C_6)$alkylsulfinyl group;
(e13) a $(C_1\text{-}C_6)$alkylsulfonyl group;
(e14) a halo$(C_1\text{-}C_6)$alkyl group;
(e17) a halo$(C_1\text{-}C_6)$alkoxy group;
(e18) a halo$(C_3\text{-}C_6)$ cycloalkyl group;
(e19) a halo$(C_1\text{-}C_6)$alkylthio group;
(e20) a halo$(C_1\text{-}C_6)$alkylsulfinyl group;
(e21) a halo$(C_1\text{-}C_6)$alkylsulfonyl group;
(e22) a $(C_1\text{-}C_6)$alkylcarbonylamino group;
(e24) a $(C_1\text{-}C_6)$alkylsulfonylamino group;
(e28) an N— $(C_1\text{-}C_6)$alkylcarboxamide group;
(e30) an oxadiazolyl group;
(e31) a substituted oxadiazolyl group having on the ring one substituent each independently selected from the group consisting of a halogen atom, a cyano group, a $(C_1\text{-}C_6)$alkyl group, a $(C_1\text{-}C_6)$alkoxy group, a $(C_3\text{-}C_6)$ cycloalkyl group, a $(C_1\text{-}C_6)$alkylthio group, a $(C_1\text{-}C_6)$ alkylsulfinyl group, a $(C_1\text{-}C_6)$alkylsulfonyl group, a halo$(C_1\text{-}C_6)$alkyl group, and a halo$(C_1\text{-}C_6)$alkoxy group;
(e32) a $(C_1\text{-}C_6)$alkoxycarbonyl group;
(e33) a methylenedioxy group formed by two adjacent substituents, wherein the methylenedioxy group is optionally substituted with one or two substituents selected from the group consisting of a halogen atom, a phenyl group, and a $(C_1\text{-}C_6)$alkyl group;
(e34) an N— $(C_1\text{-}C_6)$alkylaminosulfonyl group;
(e35) an N,N-di$(C_1\text{-}C_6)$alkylaminosulfonyl group;
(e36) an $R^6$—$(R^7$—N=)O=S group, wherein $R^6$ represents a $(C_1\text{-}C_6)$alkyl group, a $(C_3\text{-}C_6)$ cycloalkyl group, a halo$(C_1\text{-}C_6)$alkyl group, or a $(C_1\text{-}C_6)$alkoxy $(C_1\text{-}C_6)$ alkyl group, and $R^7$ represents a hydrogen atom, a cyano group, a $(C_1\text{-}C_6)$alkyl group, a $(C_3\text{-}C_6)$ cycloalkyl group, a halo$(C_1\text{-}C_6)$alkyl group, a $(C_2\text{-}C_6)$alkylcarbonyl group, or a halo$(C_2\text{-}C_6)$alkylcarbonyl group; and
(e37) a substituted $(C_3\text{-}C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group.

[18] The compound and a salt thereof according to any one of [15] to [17], wherein $R^1$ is (a1) a hydrogen atom;

$R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b23) a pyrazolyl group;

(b24) a substituted pyrazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b33) a thiadiazolyl group;

(b34) a substituted thiadiazolyl group having on the ring one substituent each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group; or (b48) a substituted quinolinyl group having on the ring one to six substituents each independently selected from the substituent group A, $R^5$ represents (i1) a $(C_1-C_6)$alkyl group, and the substituent group A consists of (e1) a halogen atom;

(e2) a cyano group;

(e6) a $(C_1-C_6)$alkyl group;

(e9) a $(C_1-C_6)$alkoxy group;

(e11) a $(C_1-C_6)$alkylthio group;

(e12) a $(C_1-C_6)$alkylsulfinyl group;

(e13) a $(C_1-C_6)$alkylsulfonyl group;

(e14) a halo$(C_1-C_6)$alkyl group;

(e17) a halo$(C_1-C_6)$alkoxy group;

(e19) a halo$(C_1-C_6)$alkylthio group;

(e21) a halo$(C_1-C_6)$alkylsulfonyl group;

(e32) a $(C_1-C_6)$alkoxycarbonyl group;

(e34) an N—$(C_1-C_6)$alkylaminosulfonyl group; and (e35) an N,N-di$(C_1-C_6)$alkylaminosulfonyl group.

Advantageous Effects of Invention

The compounds or salts thereof of the present invention have an excellent effect as insecticidal agents. The compounds or salts thereof of the present invention exhibit the excellent effect not only on pests in agriculture and horticulture, but also on pests that are parasitic to pets such as dogs and cats or domestic animals such as cattle and sheep.

DESCRIPTION OF EMBODIMENTS

In the definition of the general formulae (1), (13A), and (3A) of the compounds of the present invention, the term "halo" refers to a "halogen atom," and represents a chlorine atom, a bromine atom, an iodine atom, or a fluorine atom.

The term "$(C_1-C_6)$alkyl group" refers to a linear or branched alkyl group having 1 to 6 carbon atoms, for example, a methyl group, an ethyl group, a normal-propyl group, an isopropyl group, a normal butyl group, an isobutyl group, a secondary-butyl group, a tertiary-butyl group, a normal-pentyl group, an isopentyl group, a tertiary-pentyl group, a neopentyl group, a 2,3-dimethylpropyl group, a 1-ethylpropyl group, a 1-methylbutyl group, a 2-methylbutyl group, a normal-hexyl group, an isohexyl group, a 2-hexyl group, a 3-hexyl group, a 2-methylpentyl group, a 3-methylpentyl group, a 1,1,2-trimethylpropyl group, or a 3,3-dimethylbutyl group.

The term "$(C_2-C_6)$alkenyl group" refers to a linear or branched alkenyl group having 2 to 6 carbon atoms, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, or a 3,3-dimethyl-1-butenyl group. The term "$(C_2-C_6)$alkynyl group" refers to a linear or branched alkynyl group having 2 to 6 carbon atoms, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, or a 3,3-dimethyl-1-butynyl group.

The term "$(C_3-C_6)$cycloalkyl group" refers to a cyclic alkyl group having 3 to 6 carbon atoms, for example, a cyclopropyl group, a cyclobutyl group, a cyclopentyl group, or a cyclohexyl group. The term "$(C_1-C_6)$alkoxy group" refers to a linear or branched alkoxy group having 1 to 6 carbon atoms, for example, a methoxy group, an ethoxy group, a normal-propoxy group, an isopropoxy group, a normal-butoxy group, a secondary-butoxy group, a tertiary-butoxy group, a normal-pentyloxy group, an isopentyloxy group, a tertiary-pentyloxy group, a neopentyloxy group, a 2,3-dimethylpropyloxy group, a 1-ethylpropyloxy group, a 1-methylbutyloxy group, a normal-hexyloxy group, an isohexyloxy group, or a 1,1,2-trimethylpropyloxy group.

The term "$(C_1-C_6)$alkylthio group" refers to a linear or branched alkylthio group having 1 to 6 carbon atoms, for example, a methylthio group, an ethylthio group, a normal-propylthio group, an isopropylthio group, a normal-butylthio group, a secondary-butylthio group, a tertiary-butylthio group, a normal-pentylthio group, an isopentylthio group, a tertiary-pentylthio group, a neopentylthio group, a 2,3-dimethylpropylthio group, a 1-ethylpropylthio group, a 1-methylbutylthio group, a normal-hexylthio group, an isohexylthio group, or a 1,1,2-trimethylpropylthio group.

The term "($C_1$-$C_6$)alkylsulfinyl group" refers to a linear or branched alkylsulfinyl group having 1 to 6 carbon atoms, for example, a methylsulfinyl group, an ethylsulfinyl group, a normal-propylsulfinyl group, an isopropylsulfinyl group, a normal-butylsulfinyl group, a secondary-butylsulfinyl group, a tertiary-butylsulfinyl group, a normal-pentylsulfinyl group, an isopentylsulfinyl group, a tertiary-pentylsulfinyl group, a neopentylsulfinyl group, a 2,3-dimethylpropylsulfinyl group, a 1-ethylpropylsulfinyl group, a 1-methylbutylsulfinyl group, a normal-hexylsulfinyl group, an isohexylsulfinyl group, or a 1,1,2-trimethylpropylsulfinyl group.

The term "($C_1$-$C_6$)alkylsulfonyl group" refers to a linear or branched alkylsulfonyl group having 1 to 6 carbon atoms, for example, a methylsulfonyl group, an ethylsulfonyl group, a normal-propylsulfonyl group, an isopropylsulfonyl group, a normal-butylsulfonyl group, a secondary-butylsulfonyl group, a tertiary-butylsulfonyl group, a normal-pentylsulfonyl group, an isopentylsulfonyl group, a tertiary-pentylsulfonyl group, a neopentylsulfonyl group, a 2,3-dimethylpropylsulfonyl group, a 1-ethylpropylsulfonyl group, a 1-methylbutylsulfonyl group, a normal-hexylsulfonyl group, an isohexylsulfonyl group, or a 1,1,2-trimethylpropylsulfonyl group.

The term "($C_1$-$C_6$)alkylcarbonyl group" refers to an alkylcarbonyl group having 2 to 7 carbon atoms, such as an alkylcarbonyl group having the ($C_1$-$C_6$)alkyl group described above, for example, an acetyl group, a propanoyl group, a butanoyl group, a 2-methylpropanoyl group, a pentanoyl group, a 2-methylbutanoyl group, a 3-methylbutanoyl group, a pivaloyl group, or a hexanoyl group.

The term "($C_1$-$C_6$)alkylcarbonylamino group" refers to an alkylcarbonylamino group having 2 to 7 carbon atoms, such as an alkylcarbonylamino group having the ($C_1$-$C_6$)alkyl group described above, for example, an acetylamino group, a propanoylamino group, a butanoylamino group, a 2-methylpropanoylamino group, a pentanoylamino group, a 2-methylbutanoylamino group, a 3-methylbutanoylamino group, a pivaloylamino group, or a hexanoylamino group.

The term "($C_1$-$C_6$)alkylsulfonylamino group" refers to a linear or branched alkylsulfonylamino group having 1 to 6 carbon atoms, for example, a methylsulfonylamino group, an ethylsulfonylamino group, a normal-propylsulfonylamino group, an isopropylsulfonylamino group, a normal-butylsulfonylamino group, a secondary-butylsulfonylamino group, a tertiary-butylsulfonylamino group, a normal-pentylsulfonylamino group, an isopentylsulfonylamino group, a tertiary-pentylsulfonylamino group, a neopentylsulfonylamino group, a 2,3-dimethylpropylsulfonylamino group, a 1-ethylpropylsulfonylamino group, a 1-methylbutylsulfonylamino group, a normal-hexylsulfonylamino group, an isohexylsulfonylamino group, or a 1,1,2-trimethylpropylsulfonylamino group.

The term "N—($C_1$-$C_6$)alkylcarboxamide group" refers to an alkylcarboxamide group having 2 to 7 carbon atoms which has a linear or branched alkyl group having 1 to 6 carbon atoms, for example, an N-methylcarboxamide group, an N-ethylcarboxamide group, an N-normal-propylcarboxamide group, an N-isopropylcarboxamide group, an N-normal-butylcarboxamide group, an N-isobutylcarboxamide group, an N-secondary-butylcarboxamide group, an N-tertiary-butylcarboxamide group, an N-normal-pentylcarboxamide group, an N-isopentylcarboxamide group, an N-tertiary-pentylcarboxamide group, an N-neopentylcarboxamide group, an N-normal-hexylcarboxamide group, or an N-isohexylcarboxamide group.

The term "($C_1$-$C_6$)alkoxycarbonyl group" refers to an alkoxycarbonyl group having 2 to 7 carbon atoms, such as an alkoxycarbonyl group having the ($C_1$-$C_6$)alkoxy group described above, for example, a methoxycarbonyl group, an ethoxycarbonyl group, a normal-propoxycarbonyl group, an isopropoxycarbonyl group, a normal-butoxycarbonyl group, an isobutoxycarbonyl group, a secondary-butoxycarbonyl group, a tertiary-butoxycarbonyl group, or a pentyloxycarbonyl group.

The term "N— ($C_1$-$C_6$)alkylsulfamoyl group" refers to an N-alkylsulfamoyl group having 1 to 6 carbon atoms, for example, an N-methylsulfamoyl group, an N-ethylsulfamoyl group, an N-normal-propylsulfamoyl group, an N-isopropylsulfamoyl group, an N-normal-butylsulfamoyl group, an N-isobutylsulfamoyl group, an N-secondary-butylsulfamoyl group, an N-tertiary-butylsulfamoyl group, an N-normal-pentylsulfamoyl group, an N-isopentylsulfamoyl group, an N-tertiary-pentylsulfamoyl group, an N-neopentylsulfamoyl group, an N-(2,3-dimethylpropyl)sulfamoyl group, an N-(1-ethylpropyl)sulfamoyl group, an N-(1-methylbutyl)sulfamoyl group, an N-(2-methylbutyl)sulfamoyl group, an N-normal-hexylsulfamoyl group, an N-isohexylsulfamoyl group, an N-(2-hexyl)sulfamoyl group, an N-(3-hexyl)sulfamoyl group, an N-(2-methylpentyl)sulfamoyl group, an N-(3-methylpentyl)sulfamoyl group, an N-(1,1,2-trimethylpropyl)sulfamoyl group, or an N-(3,3-dimethylbutyl)sulfamoyl group.

The term "N—($C_1$-$C_6$)alkylaminosulfonyl group" refers to a linear or branched alkylaminosulfonyl group having 1 to 6 carbon atoms, for example, an N-methylaminosulfonyl group, an N-ethylaminosulfonyl group, an N-normal-propylaminosulfonyl group, an N-isopropylaminosulfonyl group, an N-normal-butylaminosulfonyl group, an N-secondary-butylaminosulfonyl group, an N-tertiary-butylaminosulfonyl group, an N-normal-pentylaminosulfonyl group, an N-isopentylaminosulfonyl group, an N-tertiary-pentylaminosulfonyl group, an N-neopentylaminosulfonyl group, an N-(2,3-dimethylpropyl)aminosulfonyl group, an N-(1-ethylpropyl)aminosulfonyl group, an N-(1-methylbutyl)aminosulfonyl group, an N-normal-hexylaminosulfonyl group, an N-isohexylaminosulfonyl group, or an N-(1,1,2-trimethylpropyl)aminosulfonyl group.

The term "N,N-di($C_1$-$C_6$)alkylaminosulfonyl group" refers to a linear or branched dialkylaminosulfonyl group having 1 to 6 carbon atoms, for example, an N,N-dimethylaminosulfonyl group, an N,N-diethylaminosulfonyl group, an N,N-di-normal-propylaminosulfonyl group, an N,N-di-isopropylaminosulfonyl group, an N,N-di-normal-butylaminosulfonyl group, an N,N-di-secandary-butylaminosulfonyl group, an N,N-di-tertiary-butylaminosulfonyl group, an N-methyl-N-ethylaminosulfonyl group, an N-methyl-N-normal-propylaminosulfonyl group, an N-methyl-N-isopropylaminosulfonyl group, an N-methyl-N-normal-butylaminosulfonyl group, an N-methyl-N-secondary-butylaminosulfonyl group, an N-methyl-N-tertiary-butylaminosulfonyl group, an N-methyl-N-normal-pentylaminosulfonyl group, an N-methyl-N-isopentylaminosulfonyl group, an N-methyl-N-tertiary-pentylaminosulfonyl group, an N-methyl-N-neopentylaminosulfonyl group, an N-methyl-N-(2,3-dimethylpropyl)aminosulfonyl group, an N-methyl-N-(1-ethylpropyl)aminosulfonyl group, an N-methyl-N-n(1-methylbutyl)aminosulfonyl group, an N-methyl-N-normal-hexylaminosulfonyl group, an N-methyl-N-isohexylaminosulfonyl group, or an N-methyl-N-(1,1,2-trimethylpropyl)aminosulfonyl group.

One or two or more halogen atoms may be substituted at a position that may be substituted in the groups such as the "$(C_1-C_6)$alkyl group", the "$(C_2-C_6)$alkenyl group", the "$(C_2-C_6)$alkynyl group", the "$(C_1-C_6)$alkoxy group", the "$(C_1-C_6)$alkylthio group", the "$(C_1-C_6)$alkylsulfinyl group", the "$(C_1-C_6)$alkylsulfonyl group", the "$(C_3-C_6)$ cycloalkyl group", the "$(C_1-C_6)$alkylcarbonylamino group", the "$(C_1-C_6)$alkylsulfonylamino group", and the "N—$(C_1-C_6)$alkylcarboxamide group". When there are two or more halogen atoms to be substituted, the halogen atoms may be the same or different.

The substituted groups each are referred to as a "halo$(C_1-C_6)$alkyl group", a "halo$(C_2-C_6)$alkenyl group", a "halo$(C_2-C_6)$alkynyl group", a "halo$(C_1-C_6)$alkoxy group", a "halo $(C_1-C_6)$alkylthio group", a "halo$(C_1-C_6)$alkylsulfinyl group", a "halo$(C_1-C_6)$alkylsulfonyl group", a "halo$(C_3-C_6)$ cycloalkyl group", a "halo$(C_1-C_6)$alkylcarbonylamino group", a "halo$(C_1-C_6)$alkylsulfonylamino group", and a "N-halo$(C_1-C_6)$alkylcarboxamide group", respectively.

The expression such as "$(C_1-C_6)$", "$(C_2-C_6)$", or "$(C_3-C_6)$" indicates a range of carbon atoms of various substituents. Furthermore, the expression can also indicate the definition for groups to which the above-described substituents are attached. For example, in the term "$(C_1-C_6)$alkoxy $(C_1-C_6)$alkyl group", the expression indicates that a linear or branched alkoxy group having 1 to 6 carbon atoms is attached to a linear or branched alkyl group having 1 to 6 carbon atoms.

The term "aryl group" refers to an aromatic hydrocarbon group having 6 to 10 carbon atoms, for example, a phenyl group, a 1-naphthyl group, or a 2-naphthyl group.

The term "5- to 10-membered ring heterocyclic group" includes: a 5- or 6-membered monocyclic aromatic heterocyclic group containing, as a ring constituent atom, 1 to 4 heteroatoms selected from an oxygen atom, a sulfur atom, or a nitrogen atom, in addition to a carbon atom; an aromatic fused heterocyclic group in which the monocyclic aromatic heterocyclic ring is fused to a benzene ring or a monocyclic aromatic ring; a 4- to 6-membered monocyclic non-aromatic heterocyclic group; or a non-aromatic fused heterocyclic group in which the monocyclic non-aromatic heterocyclic ring is fused to a benzene ring or a monocyclic aromatic ring. The ring constituent atom of the 5- to 10-membered ring heterocyclic group may be oxidized with an oxo group.

Examples of the "monocyclic aromatic heterocyclic group" include a furyl group, a thienyl group, a pyridyl group, a 2-oxopyridyl group, a pyrimidinyl group, a pyridazinyl group, a pyrazinyl group, a pyrrolyl group, an imidazolyl group, a pyrazolyl group, a thiazolyl group, an isothiazolyl group, an oxazolyl group, an isoxazolyl group, an oxadiazolyl group (e.g., a 1,3,4-oxadiazolyl group, a 1,2,4-oxadiazolyl group), a thiadiazolyl group (e.g., a 1,3,4-thiadiazolyl group, a 1,2,4-thiadiazolyl group), a triazolyl group (e.g., a 1,2,4-triazolyl group), a tetrazolyl group, and a triazinyl group (e.g., a 1,3,5-triazinyl group, a 1,2,4-triazinyl group). Examples of the "aromatic fused heterocyclic group" include a quinolinyl group, an isoquinolinyl group, a quinazolinyl group, a quinoxalinyl group, a cinnolinyl group, a phthalazinyl group, a naphthyridinyl group, a benzofuranyl group, a benzothienyl group, a benzoxazolyl group, a benzisoxazolyl group, a benzothiazolyl group, a benzisothiazolyl group, a benzimidazolyl group, a benzotriazolyl group, an indolyl group, an isoindolyl group, an indazolyl group, a furopyridyl group, a thienopyridyl group, a pyrrolopyridyl group (e.g., a pyrrolo[1,2-a]pyridyl group, a pyrrolo[2,3-b]pyridyl group), an oxazolopyridyl group (e.g., an oxazolo[3,2-a]pyridyl group, an oxazolo[5,4-b]pyridyl group, an oxazolo[4,5-b]pyridyl group), an isoxazolopyridyl group (e.g., an isoxazolo[2,3-a]pyridyl group, an isoxazolo[4,5-b]pyridyl group, an isoxazolo[5,4-b]pyridyl group), a thiazolopyridyl group (e.g., a thiazolo[3,2-a]pyridyl group, a thiazolo[5,4-b]pyridyl group, a thiazolo[4,5-b]pyridyl group), an isothiazolopyridyl group (e.g., an isothiazolo[2,3-a]pyridyl group, an isothiazolo[4,5-b]pyridyl group, an isothiazolo[5,4-b]pyridyl group), an imidazopyridyl group (e.g., an imidazo[1,2-a]pyridyl group, an imidazo[4,5-b]pyridyl group), a pyrazolopyridyl group (e.g., a pyrazolo[1,5-a]pyridyl group, a pyrazolo[3,4-a]pyridyl group, a pyrazolo[4,3-a]pyridyl group), an indolizinyl group, a triazolopyridyl group (e.g., a [1,2,4]triazolo[1,5-a]pyridyl group), a triazolopyrimidinyl group, a pyrrolopyrimidinyl group, a pyrrolopyrazinyl group, an imidazopyrimidinyl group, an imidazopyrazinyl group, a pyrazolopyrimidinyl group, a pyrazolothienyl group, and a pyrazolotriazinyl group.

Examples of the "monocyclic non-aromatic heterocyclic group" include an oxetanyl group, a thiethanyl group, an azetidinyl group, a pyrrolidinyl group, a pyrrolidinyl-2-one group, a piperidinyl group, a morpholinyl group, a thiomorpholinyl group, a piperazinyl group, a hexamethyleniminyl group, an oxazolidinyl group, a thiazolidinyl group, an imidazolidinyl group, an oxazolinyl group, a thiazolinyl group, an isoxazolinyl group, an imidazolinyl group, a dioxolyl group, a dioxolanyl group, a dihydrooxadiazolyl group, a 2-oxo-pyrrolidin-1-yl group, a 2-oxopyridin-4-yl group, a 2,4-dioxopyrimidin-5-yl group, a 2-oxo-1,3-oxazolidin-5-yl group, a 5-oxo-1,2,4-oxadiazolin-3-yl group, a 1,3-dioxolan-2-yl group, a 1,3-dioxan-2-yl group, a 1,3-dioxepan-2-yl group, a pyranyl group, a tetrahydropyranyl group, a thiopyranyl group, a tetrahydrothiopyranyl group, a 1-oxide tetrahydrothiopyranyl group, a 1,1-dioxide tetrahydrothiopyranyl group, a tetrahydrofuranyl group, a dioxanyl group, a pyrazolidinyl group, a pyrazolinyl group, a tetrahydropyrimidinyl group, a dihydrotriazolyl group, and a tetrahydrotriazolyl group. Examples of the "non-aromatic fused heterocyclic group" include a dihydroindolyl group, a dihydroisoindolyl group, a dihydrobenzofuranyl group, a dihydrobenzodioxynyl group, a dihydrobenzodioxepinyl group, a tetrahydrobenzofuranyl group, a chromenyl group, a dihydroquinolinyl group, a tetrahydroquinolinyl group, a dihydroisoquinolinyl group, a tetrahydroisoquinolinyl group, and a dihydrophthalazinyl group.

Examples of the salt of the compounds represented by the general formulae (1), (13A), and (3A) of the present invention can include inorganic acid a salt such as hydrochloride, sulfate, nitrate, and phosphate; organic acid a salt such as acetate, fumarate, maleate, oxalate, methanesulfonate, benzenesulfonate, and para-toluenesulfonate; and a salt with an inorganic or organic base such as a sodium ion, a potassium ion, a calcium ion, or trimethylammonium.

The compounds represented by the general formulae (1), (13A), and (3A) of the present invention and their salts may have one or more asymmetric centers in the structural formulae thereof, and may have two or more optical isomers and diastereomers. The present invention encompasses all of such isomers including each optical isomer and a mixture in which the optical isomers are included at any proportion. In addition, the compounds represented by the general formulae (1), (13A), and (3A) of the present invention and their salts may have two geometric isomers based on a carbon-carbon double bond in the structural formulae thereof. The present invention encompasses all of such isomers including each geometric isomer and a mixture in which the geometric isomers are included in any proportion. Furthermore, the compounds represented by the general formulae (1), (13A), and (3A) of the present invention and their salts may have a plurality of tautomers. The present invention encompasses all of such tautomers including each tautomer and a mixture in which the tautomers are included in any proportion.

Preferred embodiments of the compounds represented by the general formulae (1), (13A), and (3A) of the present invention are shown below. The compound represented by the general formula (13A) and the compound represented by the general formula (3A) are useful as synthetic intermediates for the compound represented by the general formula (1).

In the general formula (1), it is preferred that $R^1$ represents (a1) a hydrogen atom; (a2) a $(C_1-C_6)$alkyl group; or (a4) a $(C_2-C_6)$alkynyl group, and it is more preferred that $R^1$ represents (a1) a hydrogen atom.

In the general formula (1), it is preferred that $R^2$ represents the group of (b5), (b6), (b7), (b8), (b9), (b10), (b11), (b12), (b13), (b14), (b15), (b16), (b17), (b18), (b19), (b20), (b21), (b22), (b23), (b24), (b25), (b26), (b27), (b28), (b29), (b30), (b31), (b32), (b33), (b34), (b35), (b36), (b37), (b38), (b39), (b40), (b41), (b42), (b43), (b44), (b45), (b46), (b47), (b48), (b49), (b50), (b51), (b52), (b53), (b54), (b55), (b56), (b57), (b58), (b59), (b60), (b61), (b62), (b63), (b64), (b65), (b66), (b67), (b68), (b69), (b70), (b71), (b72), (b73), (b74), (b75), (b76), (b77), (b78), (b79), (b80), (b81), (b82), (b83), (b84), (b85), (b86), (b87), (b88), (b89), (b90), (b91), (b92), (b93), (b94), (b95), (b96), (b97), (b98), (b99), (b100), (b101), (b102), (b103), (b104), (b105), (b106), (b107), (b108), (b109) (b110), (bill), or (b112) described above; it is more preferred that $R^2$ represents the group of (b5), (b6), (b7), (b8), (b9), (b10), (b11), (b12), (b13), (b14), (b15), (b16), (b17), (b18), (b19), (b20), (b21), (b22), (b23), (b24), (b25), (b26), (b27), (b28), (b29), (b30), (b31), (b32), (b33), (b34), (b35), (b36), (b37), (b38), (b39), (b40), (b41), (b42), (b43), (b44), (b45), (b46), (b47), or (b48) described above; and it is further preferred that $R^2$ represents the group of (b5), (b6), (b7), (b8), (b9), (b10), (b11), (b12), (b13), (b14), (b23), (b24), (b27), (b28), (b29), (b30), (b33), (b34), (b43), (b44), (b45), (b46), (b47), or (b48) describe above.

In the general formula (1), it is preferred that the $R^3$ represents (ci) a hydrogen atom; or (c2) a $(C_1-C_6)$alkyl group.

In the general formula (1), it is preferred that $R^4$ represents the group of (d1), (d2), (d3), (d4), (d5), (d8), (d9), (d10), (d11), (d12), (d13), (d14), (d15), (d16), (d17), (d18), (d19), (d20), (d21), (d22), (d23), (d24), (d25), (d26), (d27), (d28), (d29), (d30), (d31), (d32), (d33), (d34), (d35), (d36), (d37), (d38), (d39), (d40), (d41), (d42), (d43), (d44), (d45), (d46), (d47), (d48), (d49), (d50), (d51), (d52), (d53), (d54), (d55), (d56), or (d57) described above; and it is more preferred that $R^4$ represents the group of (d1), (d2), (d3), (d4), (d5), (d8), (d9), (d12), (d13), (d14), (d15), (d16), (d17), (d18), (d19), (d20), (d21), (d22), (d24), (d25), (d26), (d27), (d32), (d33), (d34), (d35), (d36), (d37), (d42), (d43), (d44), (d45), (d46), (d47), (d48), (d49), (d50), (d51), (d52), (d53), (d54), (d55), (d56), or (d57) described above.

In the general formula (1), it is preferred that X represents an oxygen atom. In the general formula (1), it is preferred that Y represents an oxygen atom. In the general formula (1), it is also preferred that X represents an oxygen atom, and Y represents a sulfur atom. In the general formula (1), it is also preferred that X represents a sulfur atom, and Y represents an oxygen atom.

In the general formula (1), it is preferred that the substituent group A consists of the groups of (e1), (e2), (e4), (e5), (e6), (e9), (e10), (e11), (e12), (e13), (e14), (e17), (e18), (e19), (e20), (e21), (e22), (e24), (e28), (e30), (e31), (e32), (e33), (e34), (e35), (e36), and (e37) described above, and it is more preferred that the substituent group A consists of the groups of (e1), (e2), (e6), (e9), (e11), (e12), (e13), (e14), (e17), (e19), (e21), (e32), (e34), and (e35) described above.

In the general formula (1), it is preferred that the substituent group B consists of the groups of (f1), (f2), (f3), (f4), (f5), (f6), (f7), (f8), (f9), (f10), and (f11) described above, and it is more preferred that the substituent group B consists of the groups of (f1), (f2), (f3), and (f4) described above.

In the general formula (1), it is preferred that the substituent group C consists of the groups of (g1), (g2), (g3), (g4), (g5), (g6), (g7), (g8), (g9), (g10), (g11), (g12), (g13), (g15), and (g16) described above, and it is more preferred that the substituent group C consists of the groups of (g1), (g2), (g13), (g15), and (g16) described above.

In the general formula (1), it is preferred that the substituent group D consists of the groups of (h1), (h2), (h3), (h4), (h5), (h6), (h7), (h8), (h9), (h10), (h11), (h12), (h13), (h14), (h15), (h16), (h17), (h18), (h20), (h21), (h22), and (h23) described above, and it is more preferred that the substituent group D consists of the groups of (h1), (h2), (h3), (h5), (h6), (h8), (h11), (h12), (h17), (h20), and (h21) described above.

In the general formula (13A), it is preferred that $R^1$ represents (a1) a hydrogen atom; (a2) a $(C_1-C_6)$alkyl group; or (a4) a $(C_2-C_6)$alkynyl group, and it is more preferred that $R^1$ represents (a1) a hydrogen atom.

In the general formula (13A), it is preferred that $R^2$ represents the group of (b5), (b6), (b7), (b8), (b9), (b10), (b11), (b12), (b13), (b14), (b15), (b16), (b17), (b18), (b19), (b20), (b21), (b22), (b23), (b24), (b25), (b26), (b27), (b28), (b29), (b30), (b31), (b32), (b33), (b34), (b35), (b36), (b37), (b38), (b39), (b40), (b41), (b42), (b43), (b44), (b45), (b46), (b47), (b48), (b49), (b50), (b51), (b52), (b53), (b54), (b55), (b56), (b57), (b58), (b59), (b60), (b61), (b62), (b63), (b64), (b65), (b66), (b67), (b68), (b69), (b70), (b71), (b72), (b73), (b74), (b75), (b76), (b77), (b78), (b79), (b80), (b81), (b82), (b83), (b84), (b85), (b86), (b87), (b88), (b89), (b90), (b91), (b92), (b93), (b94), (b95), (b96), (b97), (b98), (b99), (b100), (b 101), (b102), (b103), (b104), (b105), (b106), (b107), (b108), (b109), (b110), (b111), or (b112) described above, it is more preferred that $R^2$ represents the group of (b5), (b6), (b7), (b8), (b9), (b10), (b11), (b12), (b13), (b14), (b15), (b16), (b17), (b18), (b19), (b20), (b21), (b22), (b23), (b24), (b25), (b26), (b27), (b28), (b29), (b30), (b31), (b32), (b33), (b34), (b35), (b36), (b37), (b38), (b39), (b40), (b41), (b42), (b43), (b44), (b45), (b46), (b47), or (b48) described above, and it is further preferred that $R^2$ represents the group of (b5), (b6), (b7), (b8), (b9), (b10), (b11), (b12), (b13), (b14), (b23), (b24), (b27), (b28), (b29), (b30), (b33), (b34), (b43), (b44), (b45), (b46), (b47), or (b48) described above.

In the general formula (13A), it is preferred that the substituent group A consists of the groups of (e1), (e2), (e4), (e5), (e6), (e9), (e10), (e11), (e12), (e13), (e14), (e17), (e18), (e19), (e20), (e21), (e22), (e24), (e28), (e30), (e31), (e32), (e33), (e34), (e35), (e36), and (e37) described above, and it is more preferred that the substituent group A consists of the groups of (e1), (e2), (e6), (e9), (e11), (e12), (e13), (e14), (e17), (e19), (e21), (e32), (e34), and (e35) described above.

In the general formula (3A), it is preferred that $R^1$ represents (a1) a hydrogen atom; (a2) a $(C_1-C_6)$alkyl group; or (a4) a $(C_2-C_6)$alkynyl group, and it is more preferred that $R^1$ represents (a1) a hydrogen atom.

In the general formula (3A), it is preferred that $R^2$ represents the group of (b5), (b6), (b7), (b8), (b9), (b10), (b11), (b12), (b13), (b14), (b15), (b16), (b17), (b18), (b19), (b20), (b21), (b22), (b23), (b24), (b25), (b26), (b27), (b28), (b29), (b30), (b31), (b32), (b33), (b34), (b35), (b36), (b37), (b38), (b39), (b40), (b41), (b42), (b43), (b44), (b45), (b46), (b47), (b48), (b49), (b50), (b51), (b52), (b53), (b54), (b55), (b56), (b57), (b58), (b59), (b60), (b61), (b62), (b63), (b64), (b65), (b66), (b67), (b68), (b69), (b70), (b71), (b72), (b73), (b74), (b75), (b76), (b77), (b78), (b79), (b80), (b81), (b82), (b83), (b84), (b85), (b86), (b87), (b88), (b89), (b90), (b91), (b92), (b93), (b94), (b95), (b96), (b97), (b98), (b99), (b100), (b101), (b102), (b103), (b104), (b105), (b106), (b107), (b108), (b109) (b110), (bill), or (b112) described above; it is more preferred that $R^2$ represents the group of (b5), (b6), (b7), (b8), (b9), (b10), (b11), (b12), (b13), (b14), (b15), (b16), (b17), (b18), (b19), (b20), (b21), (b22), (b23), (b24), (b25), (b26), (b27), (b28), (b29), (b30), (b31), (b32), (b33), (b34), (b35), (b36), (b37), (b38), (b39), (b40), (b41), (b42), (b43), (b44), (b45), (b46), (b47), or (b48) described above; and it is further preferred that $R^2$ represents the group of (b5), (b6), (b7), (b8), (b9), (b10), (b11), (b12), (b13), (b14), (b23), (b24), (b27), (b28), (b29), (b30), (b33), (b34), (b43), (b44), (b45), (b46), (b47), or (b48) described above.

In the general formula (3A), it is preferred that the $R^5$ represents (i1) a ($C_1$-$C_6$)alkyl group.

In the general formula (3A), it is preferred that the substituent group A consists of the groups of (e1), (e2), (e4), (e5), (e6), (e9), (e10), (e11), (e12), (e13), (e14), (e17), (e18), (e19), (e20), (e21), (e22), (e24), (e28), (e30), (e31), (e32), (e33), (e34), (e35), (e36), and (e37) described above; and it is further preferred that the substituent group A consists of the groups of (e1), (e2), (e6), (e9), (e11), (e12), (e13), (e14), (e17), (e19), (e21), (e32), (e34), and (e35) described above.

Various compounds of the present invention can be produced, for example, by the following production methods, but the present invention is not limited to these.

Production Method 1

[Formula 4]

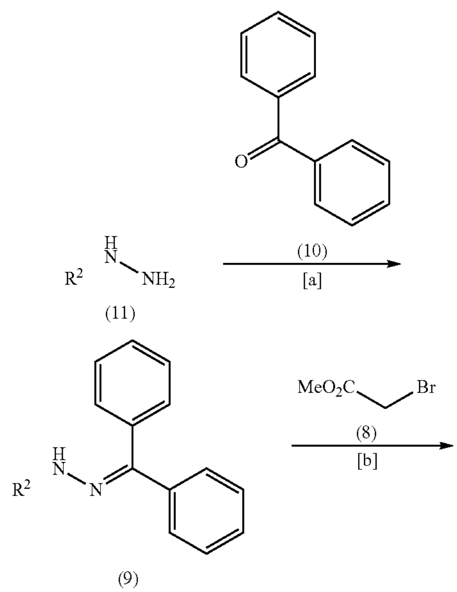

(11)

(9)

-continued

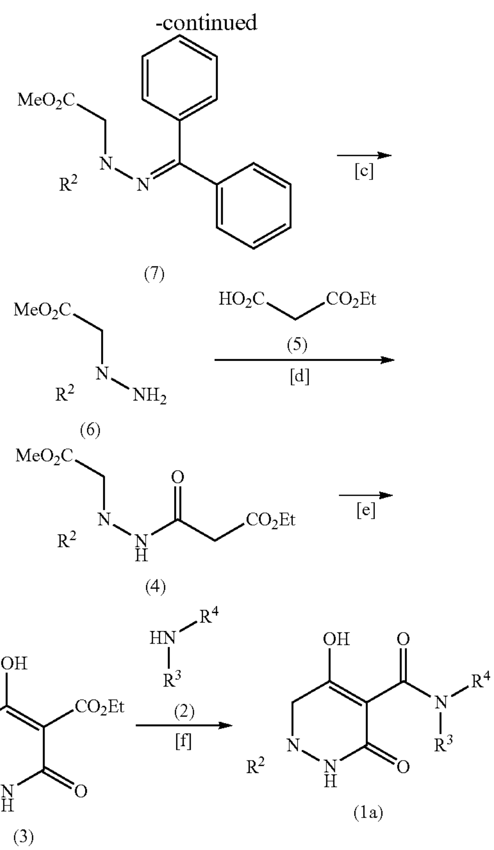

(7)

(6)

(4)

(3)

(1a)

wherein, $R^2$, $R^3$, and $R^4$ are as defined above.

The compound represented by general formula (1a) of the present invention can be produced from a compound represented by general formula (11) by steps [a], [b], [c], [d], [e] and [f] described below.

Step [a]

A step of producing a compound represented by general formula (9) by reacting a compound represented by the general formula (11) with benzophenone represented by general formula (10).

Step [b]

A step of producing a compound represented by general formula (7) by reacting a compound represented by the general formula (9) with methyl bromoacetate represented by general formula (8).

Step [c]

A step of producing a compound represented by general formula (6) by hydrolyzing a compound represented by the general formula (7).

Step [d]

A step of producing a compound represented by general formula (4) by condensing a compound represented by the general formula (6) with a compound represented by general formula (5) by an amidation reaction.

Step [e]. A step of producing a compound represented by general formula (3) by carrying out a cyclization reaction of a compound represented by the general formula (4).

Step [f]

A step of producing a compound represented by the general formula (1a) of the present invention by reacting a compound represented by the general formula (3) with a compound represented by general formula (2).

Production Method of Step [a]

A compound represented by the general formula (9) can be produced by reacting a compound represented by the general formula (11) with benzophenone represented by the general formula (10) in the presence of an acid and an inert solvent.

Examples of the acid used in this reaction include carboxylic acids such as formic acid, acetic acid, propionic acid, and trifluoroacetic acid; and sulfonic acids such as methanesulfonic acid, p-toluenesulfonic acid, and trifluoromethylsulfonic acid, and the amount of the acid used is in the range typically of 1.0-fold mol to 10-fold mol per 1 mol of the compound represented by the general formula (11).

The inert solvent used in this reaction may be any solvent that does not significantly inhibit the progress of this reaction, and examples thereof include linear or cyclic saturated hydrocarbons such as pentane, hexane, and cyclohexane; aromatic hydrocarbons such as benzene, toluene, and xylene; halogenated hydrocarbons such as methylene chloride, chloroform, and carbon tetrachloride; halogenated aromatic hydrocarbons such as chlorobenzene and dichlorobenzene; linear or cyclic ether-based inert solvents such as diethyl ether, methyl tertiary-butyl ether, dioxane, and tetrahydrofuran; nitriles such as acetonitrile and propionitrile; esters such as methyl acetate; ketones such as acetone and methyl ethyl ketone; aprotic polar solvents such as N,N-dimethylformamide, N,N-dimethylacetamide, dimethylsulfoxide, and 1,3-dimethyl-2-imidazolidinone; alcohols such as methanol, ethanol, propanol, butanol, and 2-propanol. These inert solvents can be used singly or in combination of two or more. The amount of the inert solvent used may be suitably selected from the range typically of 0.1 to 100 L per 1 mol of the compound represented by the general formula (11).

Since this reaction is an equimolar reaction, each compound can be used equimolarly, but also any of the compounds can be used in excess. The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

Production Method of Step [b]

A compound represented by the general formula (7) can be produced by reacting a compound represented by the general formula (9) with methyl bromoacetate represented by the general formula (8) in the presence of a base and an inert solvent.

Examples of the base used in this reaction include hydroxides such as lithium hydroxide, sodium hydroxide, potassium hydroxide, and calcium hydroxide; alkoxides such as sodium methoxide, sodium ethoxide, sodium tertiary-butoxide, and potassium tertiary-butoxide; and alkali metal hydrides such as sodium hydride and potassium hydride, and the amount of the base used is in the range typically of 1-fold mol to 10-fold mol based on the compound represented by the general formula (9).

The inert solvent used in this reaction may be any solvent that does not significantly inhibit the progress of this reaction, and examples thereof include linear or cyclic saturated hydrocarbons such as pentane, hexane, and cyclohexane; aromatic hydrocarbons such as benzene, toluene, and xylene; halogenated aromatic hydrocarbons such as chlorobenzene and dichlorobenzene; linear or cyclic ether-based inert solvents such as diethyl ether, methyl tertiary-butyl ether, dioxane, and tetrahydrofuran; nitriles such as acetonitrile and propionitrile; aprotic polar solvents such as N,N-dimethylformamide, N,N-dimethylacetamide, dimethylsulfoxide, and 1,3-dimethyl-2-imidazolidinone. These inert solvents can be used singly or in combination of two or more. The amount of the inert solvent used may be suitably selected from the range typically of 0.1 to 100 L per 1 mol of the compound represented by the general formula (9).

Since this reaction is an equimolar reaction, each compound can be used equimolarly, but also any of the compounds can be used in excess. The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

Production Method of Step [c]

A compound represented by the general formula (6) can be produced by reacting a compound represented by the general formula (7) in the presence of concentrated hydrochloric acid and an inert solvent.

The inert solvent used in this reaction may be any solvent that does not significantly inhibit the progress of this reaction, and examples thereof include linear or cyclic saturated hydrocarbons such as pentane, hexane, and cyclohexane; aromatic hydrocarbons such as benzene, toluene, and xylene; halogenated hydrocarbons such as methylene chloride, chloroform, and carbon tetrachloride; halogenated aromatic hydrocarbons such as chlorobenzene and dichlorobenzene; linear or cyclic ether-based inert solvents such as diethyl ether, methyl tertiary-butyl ether, dioxane, tetrahydrofuran, and 2-methyltetrahydrofuran; nitriles such as acetonitrile and propionitrile; esters such as methyl acetate; ketones such as acetone and methyl ethyl ketone; aprotic polar solvents such as N,N-dimethylformamide, N,N-dimethylacetamide, dimethylsulfoxide, and 1,3-dimethyl-2-imidazolidinone; alcohols such as methanol, ethanol, propanol, butanol, and 2-propanol; and water. These inert solvents can be used singly or in combination of two or more. The amount used may be suitably selected from the range typically of 0.1 to 100 L per 1 mol of the compound represented by the general formula (7).

The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

Production Method of Step [d]

A compound represented by the general formula (4) can be produced by condensing a compound represented by the general formula (6) with monoethyl malonate represented by the general formula (5) by an amidation method commonly used in organic synthesis.

Production Method of Step [e]

A compound represented by the general formula (3) can be produced by carrying out a cyclization reaction of a compound represented by the general formula (4) in the presence of a base and an inert solvent.

Examples of the base used in this reaction include hydroxides such as lithium hydroxide, sodium hydroxide, potassium hydroxide, and calcium hydroxide; alkoxides such as sodium methoxide, sodium ethoxide, sodium tertiary-butoxide, and potassium tertiary-butoxide; alkali metal hydrides such as sodium hydride and potassium hydride; carbonates such as lithium carbonate, lithium hydrogen carbonate, sodium carbonate, sodium hydrogen carbonate, potassium carbonate, potassium hydrogen carbonate, calcium carbonate, and magnesium carbonate; acetates such as lithium acetate, sodium acetate, and potassium acetate; and organic bases such as pyridine, picoline, lutidine, triethylamine, tributylamine, and diisopropylethylamine, and the amount of the base used is in the range typically of 1-fold mol to 10-fold mol based on the compound represented by the general formula (4).

The inert solvent used in this reaction may be any solvent that does not significantly inhibit the progress of this reaction, and examples thereof include linear or cyclic saturated hydrocarbons such as pentane, hexane, and cyclohexane; aromatic hydrocarbons such as benzene, toluene, and xylene; halogenated aromatic hydrocarbons such as chlorobenzene and dichlorobenzene; linear or cyclic ether-based inert solvents such as diethyl ether, methyl tertiary-butyl ether, dioxane, and tetrahydrofuran; nitriles such as acetonitrile and propionitrile; aprotic polar solvents such as N,N-dimethylformamide, N,N-dimethylacetamide, dimethylsulfoxide, 1,3-dimethyl-2-imidazolidinone; and alcohols such as methanol, ethanol, propanol, butanol, and 2-propanol. These inert solvents can be used singly or in combination of two or more. The amount of the inert solvent used may be suitably selected from the range typically of 0.1 to 100 L per 1 mol of the compound represented by the general formula (4).

The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

Production Method of Step [f]

The compound represented by the general formula (1a) of the present invention can be produced by reacting a compound represented by the general formula (3) with a compound represented by the general formula (2) in the presence of an inert solvent.

The inert solvent used in this reaction may be any solvent that does not significantly inhibit the progress of this reaction, and examples thereof include linear or cyclic saturated hydrocarbons such as pentane, hexane, and cyclohexane; aromatic hydrocarbons such as benzene, toluene, and xylene; halogenated hydrocarbons such as methylene chloride, chloroform, and carbon tetrachloride; halogenated aromatic hydrocarbons such as chlorobenzene and dichlorobenzene; linear or cyclic ether-based inert solvents such as diethyl ether, methyl tertiary-butyl ether, dioxane, and tetrahydrofuran; nitriles such as acetonitrile and propionitrile; esters such as methyl acetate; ketones such as acetone and methyl ethyl ketone; aprotic polar solvents such as N,N-dimethylformamide, N,N-dimethylacetamide, dimethylsulfoxide, 1,3-dimethyl-2-imidazolidinone; and alcohols such as methanol, ethanol, propanol, butanol, and 2-propanol. These inert solvents can be used singly or in combination of two or more. The amount of the inert solvent used may be suitably selected from the range typically of 0.1 to 100 L per 1 mol of the compound represented by the general formula (3).

Since this reaction is an equimolar reaction, each compound can be used equimolarly, but also any of the compounds can be used in excess. The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

Production Method 2

[Formula 5]

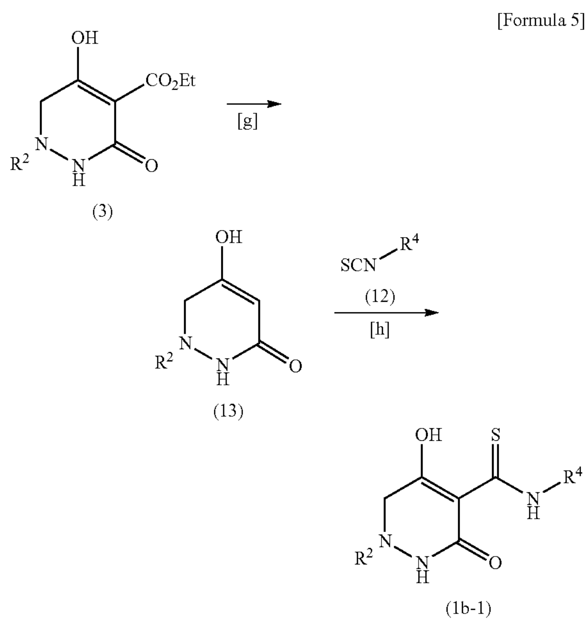

(3)

(13)

(1b-1)

wherein $R^2$, and $R^4$ are as defined above.

The compound represented by general formula (1b-1) of the present invention can be produced from a compound represented by the general formula (3) by steps [g] and [h] described below.

Step [g]

A step of producing a compound represented by general formula (13) by decarboxylating a compound represented by the general formula (3).

Step [h]

A step of producing a compound represented by the general formula (1b-1) of the present invention by reacting a compound represented by the general formula (13) with a compound represented by general formula (12).

Production Method of Step [g]

A compound represented by the general formula (13) can be produced by reacting a compound represented by the general formula (3) under heating conditions in the presence of an inert solvent.

The inert solvent used in this reaction may be any solvent that does not significantly inhibit the progress of this reaction, and examples thereof include linear or cyclic saturated hydrocarbons such as pentane, hexane, and cyclohexane; aromatic hydrocarbons such as benzene, toluene, and xylene; halogenated aromatic hydrocarbons such as chlorobenzene and dichlorobenzene; linear or cyclic ether-based inert solvents such as diethyl ether, methyl tertiary-butyl ether, dioxane, and tetrahydrofuran; nitriles such as acetonitrile and propionitrile; aprotic polar solvents such as N,N-dimethylformamide, N,N-dimethylacetamide, dimethylsulfoxide, and 1,3-dimethyl-2-imidazolidinone; alcohols such as methanol, ethanol, propanol, butanol, and 2-propanol; and water. These inert solvents can be used singly or in combination of two or more. The amount of the inert solvent used may be suitably selected from a range typically of 0.1 to 100 L per 1 mol of the compound represented by the general formula (13).

The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

Production Method of Step [h]

A compound represented by the general formula (1b-1) of the present invention can be produced by reacting a compound represented by the general formula (13) with a compound represented by the general formula (12) in the presence of a base and an inert solvent.

Examples of the base that can be used in this reaction include hydroxides such as lithium hydroxide, sodium hydroxide, potassium hydroxide, and calcium hydroxide; alkoxides such as sodium methoxide, sodium ethoxide, sodium tertiary-butoxide, potassium tertiary-butoxide; sodium hydride, alkali metal hydrides such as sodium hydride and potassium hydride; carbonates such as lithium carbonate, lithium hydrogen carbonate, sodium carbonate, sodium hydrogen carbonate, potassium carbonate, potassium hydrogen carbonate, calcium carbonate, magnesium carbonate, and cesium carbonate; acetates such as lithium acetate, sodium acetate, and potassium acetate; and organic bases such as pyridine, picoline, lutidine, triethylamine, tributylamine, and diisopropylethylamine, and the amount of the base used is in the range typically of 1-fold mol to 10-fold mol based on the compound represented by the general formula (13).

The inert solvent used in this reaction may be any solvent that does not significantly inhibit the progress of the reaction, and examples thereof include linear or cyclic saturated hydrocarbons such as pentane, hexane, and cyclohexane; aromatic hydrocarbons such as benzene, toluene, and xylene; halogenated aromatic hydrocarbons such as chlorobenzene and dichlorobenzene; linear or cyclic ether-based inert solvents such as diethyl ether, methyl tertiary-butyl ether, dioxane, and tetrahydrofuran; nitriles such as acetonitrile and propionitrile; aprotic polar solvents such as N,N-dimethylformamide, N,N-dimethylacetamide, dimethylsulfoxide, and 1,3-dimethyl-2-imidazolidinone; and alcohols such as methanol, ethanol, propanol, butanol, and 2-propanol. These inert solvents can be used singly or in combination of two or more. The amount used may be suitably selected from the range typically of 0.1 to 100 L per 1 mol of the compound represented by the general formula (13).

Since this reaction is an equimolar reaction, each compound can be used equimolarly, but also any of the compounds can be used in excess. The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

Production Method 3

[Formula 6]

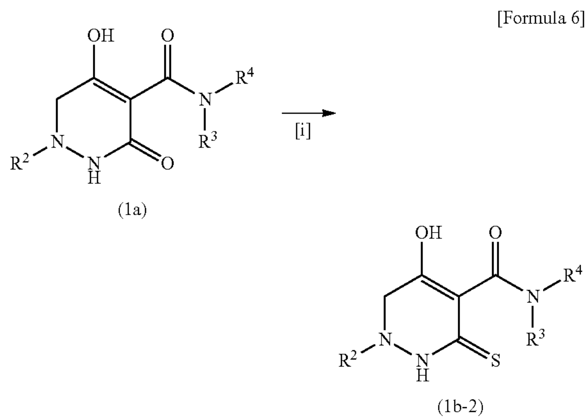

(1a)
(1b-2)

wherein $R^2$, $R^3$, and $R^4$ are as defined above.

The compound represented by general formula (1b-2) of the present invention can be produced from a compound represented by the general formula (1a) by step [i] described below.

Step [i]

A step of producing a compound represented by the general formula (1b-2) by reacting a compound represented by the general formula (1a) with a sulfurizing agent.

Examples of the sulfurizing agent that can be used in this reaction include a Lawesson's reagent and diphosphorus pentasulfide, and the amount used is in the range typically of 1.0-fold mol to 10-fold mol based on the amount of the compound represented by the general formula (1a).

This reaction may or may not use a solvent. The solvent used in this reaction may be any solvent that does not significantly inhibit the progress of this reaction, and examples thereof include linear or cyclic saturated hydrocarbons such as pentane, hexane, and cyclohexane; aromatic hydrocarbons such as benzene, toluene, and xylene; halogenated aromatic hydrocarbons such as chlorobenzene and dichlorobenzene; linear or cyclic ether-based inert solvents such as diethyl ether, methyl tertiary-butyl ether, dioxane, and tetrahydrofuran; nitriles such as acetonitrile and propionitrile; aprotic polar solvents such as N,N-dimethylformamide, N,N-dimethylacetamide, dimethylsulfoxide, 1,3-dimethyl-2-imidazolidinone; and alcohols such as methanol, ethanol, propanol, butanol, and 2-propanol. These inert solvents can be used singly or in combination of two or more. The amount of the inert solvent used may be suitably selected from the range typically of 0.1 to 100 L per 1 mol of the compound represented by the general formula (1a).

The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

The salt of the compound represented by the general formula (1a), (1b-1), or (1b-2) can be produced by reacting a compound represented by the general formula (1a), (1b-1), or (1b-2) with an inorganic or organic base in the presence of an inert solvent.

Examples of the inorganic or organic base used in this reaction include hydroxides such as lithium hydroxide, sodium hydroxide, potassium hydroxide, and calcium hydroxide; alkoxides such as sodium methoxide, sodium ethoxide, sodium tertiary-butoxide, and potassium tertiary-butoxide; carbonates such as lithium carbonate, lithium hydrogen carbonate, sodium carbonate, sodium hydrogen carbonate, potassium carbonate, potassium hydrogen carbonate, calcium carbonate, and magnesium carbonate; acetates such as lithium acetate, sodium acetate, and potassium acetate; and organic bases such as pyridine, picoline, lutidine, triethylamine, tributylamine, and diisopropylethylamine, and the amount of the base used is in the range typically of 1-fold mol to 10-fold mol based on the compound represented by the general formula (1a), (1b-1) or (1b-2).

The inert solvent used in this reaction may be any solvent that does not significantly inhibit the progress of this reaction, and examples thereof include linear or cyclic saturated hydrocarbons such as pentane, hexane, and cyclohexane; aromatic hydrocarbons such as benzene, toluene, and xylene; halogenated aromatic hydrocarbons such as chlorobenzene and dichlorobenzene; linear or cyclic ether-based inert solvents such as diethyl ether, methyl tertiary-butyl ether, dioxane, and tetrahydrofuran; nitriles such as acetonitrile and propionitrile; aprotic polar solvents such as N,N-dimethylformamide, N,N-dimethylacetamide, dimethylsulfoxide, 1,3-dimethyl-2-imidazolidinone; and alcohols such as methanol, ethanol, propanol, butanol, and 2-propanol. These inert solvents can be used singly or in combination of two or more. The amount of the inert solvent used may be suitably selected from the range typically of 0.1 to 100 L per 1 mol of the compound represented by the general formula (1a), (1b-1), or (1b-2).

The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

Production Method 1 of Production Intermediate

[Formula 7]

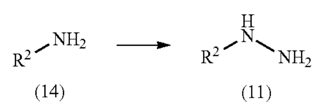

(14) (11)

wherein $R^2$ is as defined above.

A production intermediate of a compound represented by the general formula (11) of the present invention can be produced from a compound represented by general formula (14).

Production Method

A compound represented by the general formula (11) can be produced by reacting a compound represented by the general formula (14) with sodium nitrite in concentrated hydrochloric acid, and then reducing with a reducing agent.

Examples of the reducing agent used in this reaction include sodium sulfite and tin chloride. The amount of the reducing agent used is in the range typically of 1.0-fold mol to 10-fold mol based on the compound represented by the general formula (14).

The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

Production Method 2 of Intermediate

[Formula 8]

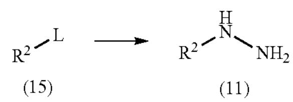

(15) (11)

wherein $R^2$ is as defined above, and L represents a leaving group such as a halogen atom, a mesyl group, a tosyl group, or a trifluorosulfonyl group. A production intermediate of a compound represented by the general formula (11) of the present invention can also be produced from a compound represented by general formula (15) by the method described below.

Production Method

A compound represented by the general formula (11) can be produced by reacting a compound represented by the general formula (15) with hydrazine monohydrate in the presence of an inert solvent.

The inert solvent used in this reaction may be any solvent that does not significantly inhibit the progress of this reaction, and examples thereof include linear or cyclic saturated hydrocarbons such as pentane, hexane, and cyclohexane; aromatic hydrocarbons such as benzene, toluene, and xylene; halogenated aromatic hydrocarbons such as chlorobenzene and dichlorobenzene; linear or cyclic ether-based inert solvents such as diethyl ether, methyl tertiary-butyl ether, dioxane, and tetrahydrofuran; and alcohols such as methanol, ethanol, propanol, butanol, and 2-propanol. These inert solvents can be used singly or in combination of two or more. The amount used may be suitably selected from the range typically of 0.1 to 100 L per 1 mol of the compound represented by the general formula (15).

Since this reaction is an equimolar reaction, each compound can be used equimolarly, but also any compound can be used in excess. The reaction temperature in this reaction may be in the range typically from about 0° C. to the boiling point of the solvent used. The reaction time varies depending on the reaction scale, reaction temperature, or the like, and is not constant, and may be appropriately selected from the range typically of a few minutes to 48 hours. After the reaction is completed, a target compound can be isolated by a routine method from the reaction system containing the target compound, and the target compound may be produced via purification as necessary by recrystallization, column chromatography, or the like.

Hereinafter, representative examples of the compound represented by the general formula (1) of the present invention are illustrated in Table 1 and Table 2, but the present invention is not limited to these.

In the following tables, "Me" represents a methyl group, "Et" represents an ethyl group, "n-Pr" represents a normal-propyl group, "i-Pr" represents an isopropyl group, "n-Bu" represents a normal-butyl group, "t-Bu" represents a tertiary-butyl group, "n-Pen" represents a normal-pentyl group, "c-Pen" represents a cyclopentyl group, "Ph" represents a phenyl group, and "Bn" represents a benzyl group. In the structural formula, a closed circle indicates a bonding position. Physical property indicates melting point (° C.), or $H^1$—NMR. The $H^1$—NMR data are shown in Table 6.

[Formula 9]

(1a)

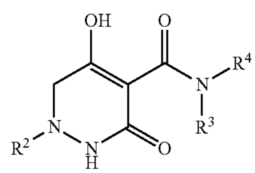

TABLE 1

| Compound No. | $R^2$ | $R^4$ | Physical property value |
|---|---|---|---|
| 1-1 | 2-$CF_3$-Ph | 4-F-Ph | 204-206 |
| 1-2 | 3-$CF_3$-Ph | 4-F-Ph | |
| 1-3 | 4-Cl-Ph | 4-F-Ph | |
| 1-4 | 4-CN-Ph | 4-F-Ph | 208-212 |
| 1-5 | 4-$CF_3$-Ph | 2-F-Ph | |
| 1-6 | 4-$CF_3$-Ph | 3-F-Ph | |
| 1-7 | 4-$CF_3$-Ph | 4-F-Ph | 196-197 |
| 1-8* | 4-$CF_3$-Ph | 4-F-Ph | |
| 1-9 | 4-$CF_3$-Ph | 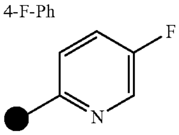 | 198-203 |
| 1-10 | 4-$OCH_3$-Ph | 4-F-Ph | |
| 1-11 | 4-$OCF_3$-Ph | 4-F-Ph | 155-159 |
| 1-12 | 4-$SCH_3$-Ph | 4-F-Ph | |
| 1-13 | 4-$SCH_2CH_3$-Ph | 4-F-Ph | |
| 1-14 | 4-$SCF_3$-Ph | 4-F-Ph | 159-164 |
| 1-15 | 2-F,4-$CF_3$-Ph | 4-F-Ph | |
| 1-16 | 3,4-Cl-Ph | 4-F-Ph | 225-227 |
| 1-17 | 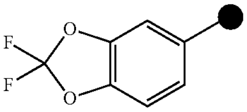 | 4-F-Ph | |
| 1-18 | 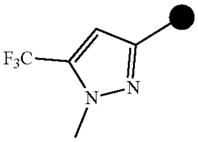 | 4-F-Ph | 156-157 |
| 1-19 | 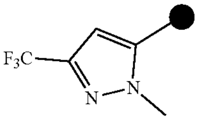 | 4-F-Ph | |
| 1-20 | 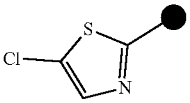 | 4-F-Ph | |

TABLE 1-continued
| Compound No. | $R^2$ | $R^4$ | Physical property value |
|---|---|---|---|
| 1-21 | 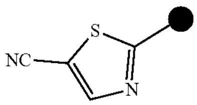 | 4-F-Ph | 232-234 |
| 1-22 | 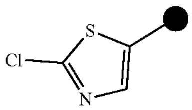 | 4-F-Ph | |
| 1-23 | 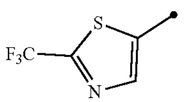 | 4-F-Ph | 142-147 |
| 1-24 | 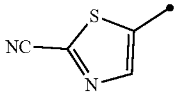 | 4-F-Ph | |
| 1-25 | 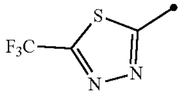 | 4-F-Ph | |
| 1-26 | 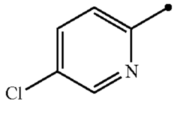 | 4-F-Ph | 197-201 |
| 1-27 | 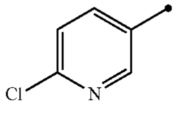 | 4-F-Ph | 204-213 |
| 1-28 | 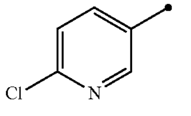 | 4-CN-Ph | 231-233 |
| 1-29 | 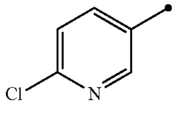 | 3,4-$F_2$-Ph | 204-210 |
| 1-30 | 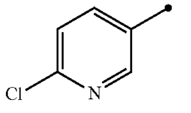 | 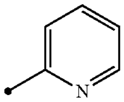 | 210-218 |
| 1-31 | 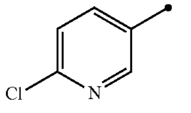 | 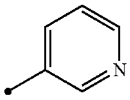 | |
| 1-32 | 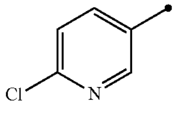 | 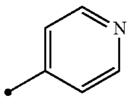 | |
| 1-33 | 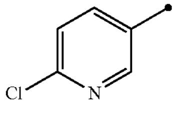 | 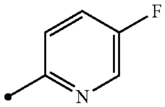 | 225-232 |

TABLE 1-continued
| Compound No. | $R^2$ | $R^4$ | Physical property value |
|---|---|---|---|
| 1-34 | 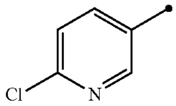 | 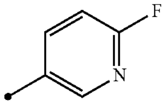 | |
| 1-35 | 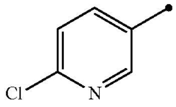 | 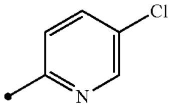 | 233-235 |
| 1-36 | 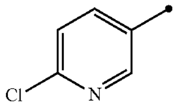 | 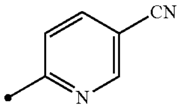 | 233-237 |
| 1-37 | 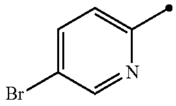 | 4-F-Ph | 196-200 |
| 1-38 | 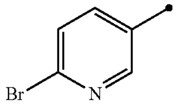 | 4-F-Ph | 206-210 |
| 1-39 | 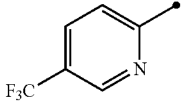 | 4-F-Ph | 187-192 |
| 1-40 | 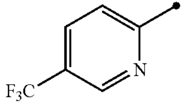 | 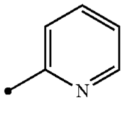 | 251-255 |
| 1-41 | 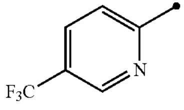 | 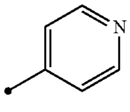 | |
| 1-42 | 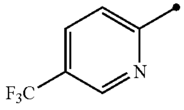 | 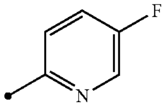 | 217-222 |
| 1-43 | 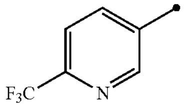 | 4-F-Ph | 203-208 |
| 1-44 | 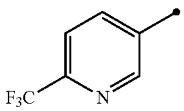 | 4-CN-Ph | 206-208 |
| 1-45 | 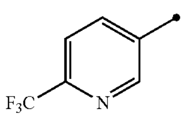 | 3,4-$F_2$-Ph | 203-205 |
| 1-46 | 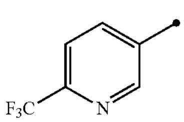 | 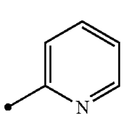 | 125-130 |

TABLE 1-continued
| Compound No. | $R^2$ | $R^4$ | Physical property value |
|---|---|---|---|
| 1-47 | 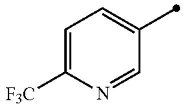 | 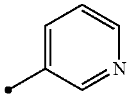 | 207-212 |
| 1-48 | 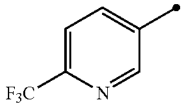 | 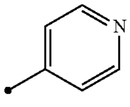 | 237-242 |
| 1-49 | 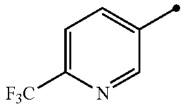 | 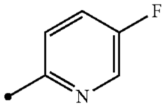 | 220-225 |
| 1-50 | 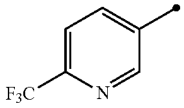 | 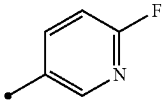 | 214-218 |
| 1-51 | 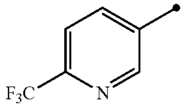 | 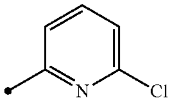 | 218-221 |
| 1-52 | 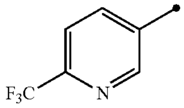 | 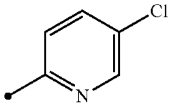 | 224-229 |
| 1-53 | 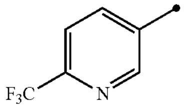 | 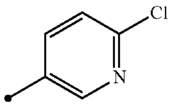 | 226-231 |
| 1-54 | 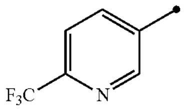 | 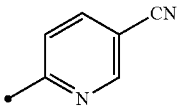 | 207-208 |
| 1-55 | 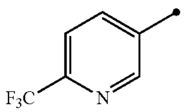 | 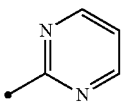 | 202-207 |
| 1-56 | 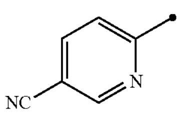 | 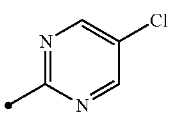 | 204-209 |
| 1-57 | 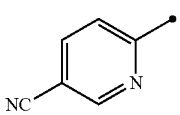 | 4-F-Ph | 199 |
| 1-58 | 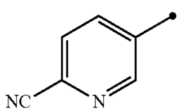 | 4-F-Ph | 227-229 |

TABLE 1-continued
| Compound No. | $R^2$ | $R^4$ | Physical property value |
|---|---|---|---|
| 1-59 | 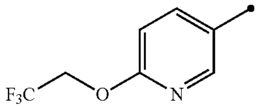 | 4-F-Ph | 250-255 |
| 1-60 | 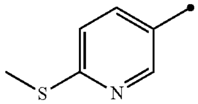 | 4-F-Ph | |
| 1-61 | 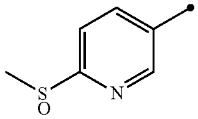 | 4-F-Ph | |
| 1-62 | 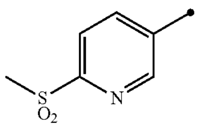 | 4-F-Ph | 211-215 |
| 1-63 | 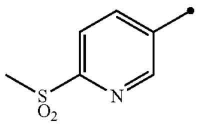 | 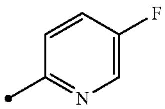 | 217-222 |
| 1-64 | 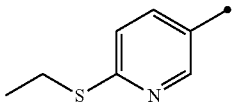 | 4-F-Ph | |
| 1-65 | 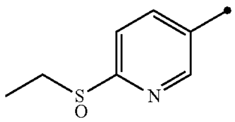 | 4-F-Ph | |
| 1-66 | 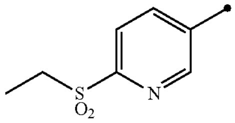 | 4-F-Ph | 217-221 |
| 1-67 | 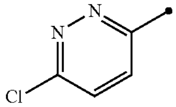 | 4-F-Ph | 216-221 |
| 1-68 | 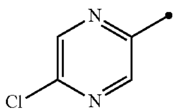 | 4-F-Ph | 220-228 |
| 1-69 | 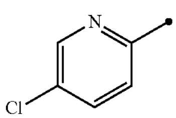 | 4-F-Ph | 212-216 |
| 1-70 | 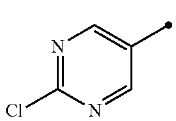 | 4-F-Ph | 204-212 |

TABLE 1-continued
| Compound No. | $R^2$ | $R^4$ | Physical property value |
|---|---|---|---|
| 1-71 | 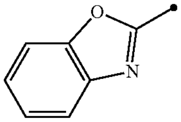 | 4-F-Ph | |
| 1-72 | 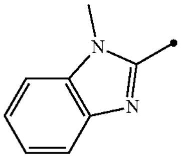 | 4-F-Ph | |
| 1-73 | 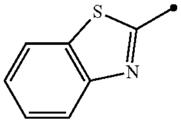 | 4-F-Ph | 120-125 |
| 1-74 | 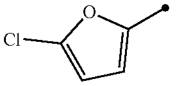 | 4-F-Ph | |
| 1-75 | 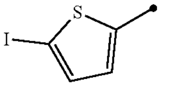 | 4-F-Ph | |
| 1-76 | 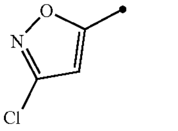 | 4-F-Ph | |
| 1-77 | 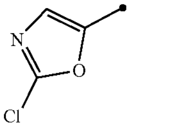 | 4-F-Ph | |
| 1-78 | 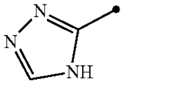 | 4-F-Ph | |
| 1-79 | 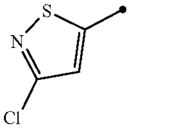 | 4-F-Ph | |
| 1-80 | 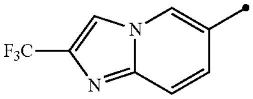 | 4-F-Ph | |
| 1-81 | 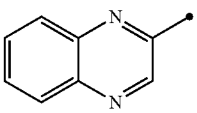 | 4-F-Ph | |
| 1-82 | 4-$CF_3$-Ph | Ph | |
| 1-83 | 4-$CF_3$-Ph | Bn | |
| 1-84 | 4-$CF_3$-Ph | Et | |
| 1-85 | 4-$CF_3$-Ph | 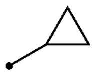 | |

TABLE 1-continued
| Compound No. | $R^2$ | $R^4$ | Physical property value |
|---|---|---|---|
| 1-86 | 4-$CF_3$-Ph | 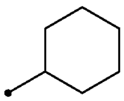 | |
| 1-87 | 4-$CF_3$-Ph | 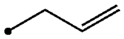 | |
| 1-88 | 4-$CF_3$-Ph | 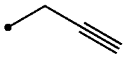 | |
| 1-89 | 4-$CF_3$-Ph | $CH_2CHF_2$ | 109-112 |
| 1-90 | 4-$CF_3$-Ph | $CH_2CF_3$ | |
| 1-91 | 4-$CF_3$-Ph | $CH_2CH_2OCH_3$ | |
| 1-92 | 4-$CF_3$-Ph | $CH_2CH_2SCH_3$ | |
| 1-93 | 4-$CF_3$-Ph | $CH_2CN$ | |
| 1-94 | 4-$CF_3$-Ph | 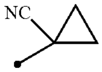 | |
| 1-95 | 4-$CF_3$-Ph | $SO_2CH_3$ | |
| 1-96 | 4-$CF_3$-Ph | $SO_2NHCH_3$ | |
| 1-97 | 4-$CF_3$-Ph | 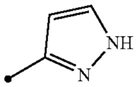 | |
| 1-98 | 4-$CF_3$-Ph | 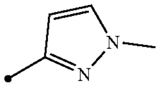 | |
| 1-99 | 4-$CF_3$-Ph | 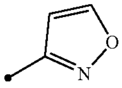 | |
| 1-100 | 4-$CF_3$-Ph | 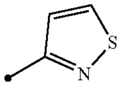 | |
| 1-101 | 4-$CF_3$-Ph | 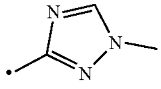 | |
| 1-102 | 4-$CF_3$-Ph | 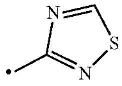 | |
| 1-103 | 4-$CF_3$-Ph | 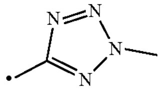 | |
| 1-104 | 4-$CF_3$-Ph | 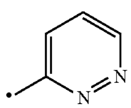 | |
| 1-105 | 4-$CF_3$-Ph | 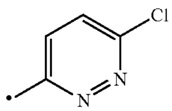 | |
| 1-106 | 4-$CF_3$-Ph | 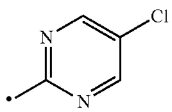 | |

TABLE 1-continued
| Compound No. | $R^2$ | $R^4$ | Physical property value |
|---|---|---|---|
| 1-107 | 4-$CF_3$-Ph | 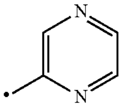 | |
| 1-108 | 4-$CF_3$-Ph | 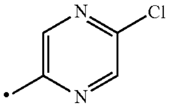 | |
| 1-109 | 4-$CF_3$-Ph | 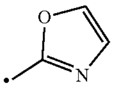 | |
| 1-110 | 4-$CF_3$-Ph | 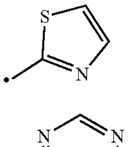 | |
| 1-111 | 4-$CF_3$-Ph | 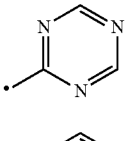 | |
| 1-112 | 4-$CF_3$-Ph | 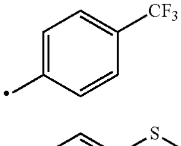 | |
| 1-113 | 4-$CF_3$-Ph | 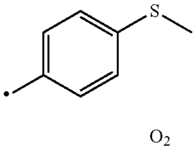 | |
| 1-114 | 4-$CF_3$-Ph | 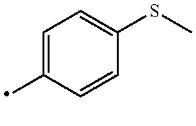 | |
| 1-115 | 4-$CF_3$-Ph | 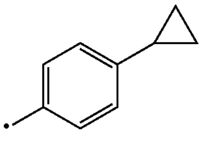 | |
| 1-116 | 4-$CF_3$-Ph | 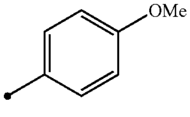 | |
| 1-117 | 4-$CF_3$-Ph | 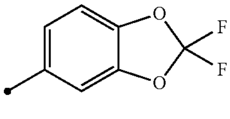 | |
| 1-118 | 4-$CF_3$-Ph | 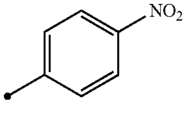 | |
| 1-119 | 4-$CF_3$-Ph | 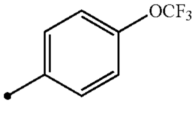 | |

TABLE 1-continued
| Compound No. | $R^2$ | $R^4$ | Physical property value |
|---|---|---|---|
| 1-120 | 4-$CF_3$-Ph | 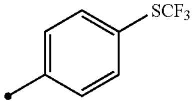 | |
| 1-121 | 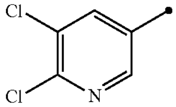 | 4-F-Ph | 207-210 |
| 1-122** | 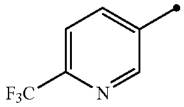 | 4-F-Ph | >300 |
| 1-123 | 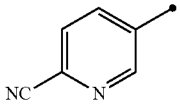 | 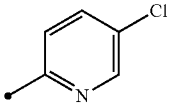 | 227-229 |
| 1-124 | 4-$SO_2CF_3$-Ph | 4-F-Ph | 216-220 |
| 1-125 | 4-$CO_2$Et-Ph | 4-F-Ph | 212-214 |
| 1-126 | 4-$CO_2$Et-Ph | 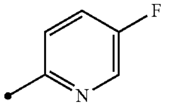 | 217-220 |
| 1-127 | 3-$CF_3$-4-CN-Ph | 4-F-Ph | 148-152 |
| 1-128 | 3-$CF_3$-4-CN-Ph | 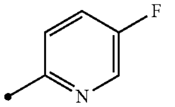 | 189-192 |
| 1-129 | 3-CN-4-Me-Ph | 4-F-Ph | 170-172 |
| 1-130 | 3,4-CN-Ph | 4-F-Ph | 152-158 |
| 1-131 | 2,3,5,6-F-4-$SCF_3$-Ph | 4-F-Ph | 155-160 |
| 1-132 | 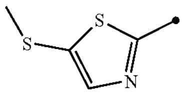 | 4-F-Ph | 178-179 |
| 1-133 | 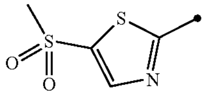 | 4-F-Ph | 236-237 |
| 1-134 | 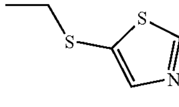 | 4-F-Ph | 182-183 |
| 1-135 | 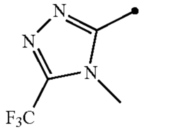 | 4-F-Ph | 121-122 |
| 1-136 | 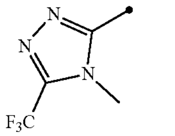 | 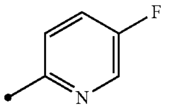 | 117-118 |

TABLE 1-continued
| Compound No. | $R^2$ | $R^4$ | Physical property value |
|---|---|---|---|
| 1-137 | 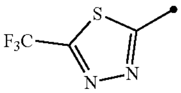 | 4-F-Ph | 98-100 |
| 1-138 | 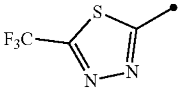 | 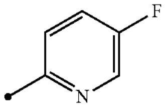 | 132-136 |
| 1-139 | 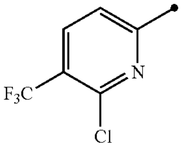 | 4-F-Ph | 199-201 |
| 1-140 | 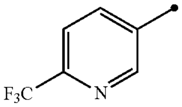 | 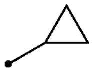 | 135-137 |
| 1-141 | 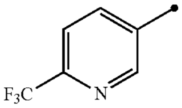 | 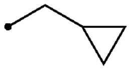 | 162-164 |
| 1-142 | 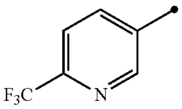 | 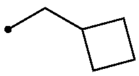 | 152-154 |
| 1-143 | 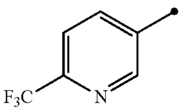 | 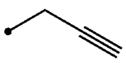 | 204-206 |
| 1-144 | 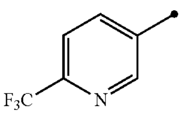 | $CH_2CF_3$ | 192-193 |
| 1-145 | 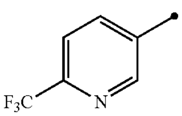 | $CH_2CHF_2$ | 177-178 |
| 1-146 | 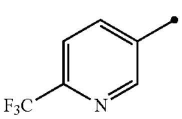 | 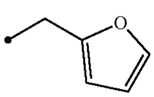 | 147-149 |
| 1-147 | 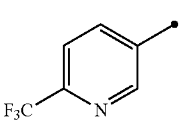 | 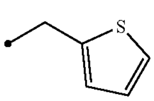 | 172-174 |
| 1-148 | 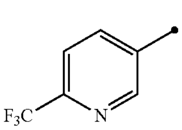 | 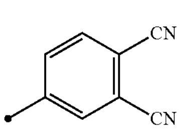 | 261-262 |

TABLE 1-continued
| Compound No. | $R^2$ | $R^4$ | Physical property value |
| --- | --- | --- | --- |
| 1-149 | 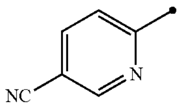 | 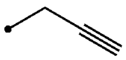 | 94-97 |
| 1-150 | 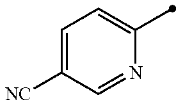 | 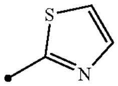 | 264-269 |
| 1-151 | 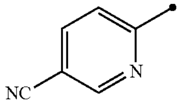 | 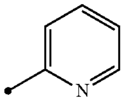 | 210-213 |
| 1-152 | 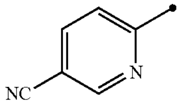 | 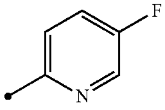 | 200-203 |
| 1-153 | 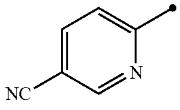 | 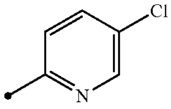 | 224-228 |
| 1-154 | 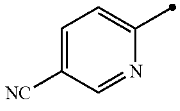 | 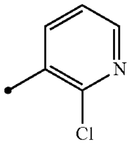 | 219-225 |
| 1-155 | 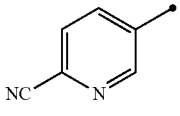 | 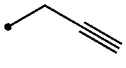 | 217-218 |
| 1-156 | 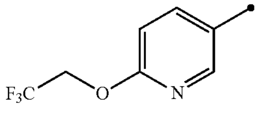 | 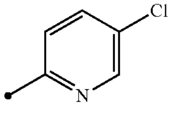 | 210-213 |
| 1-157 | 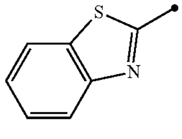 | 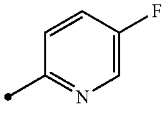 | 213-217 |
| 1-158 | 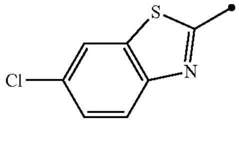 | 4-F-Ph | 238-240 |
| 1-159 | 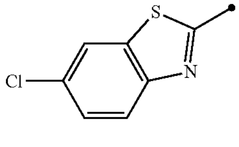 | 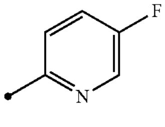 | 245-247 |
| 1-160 | 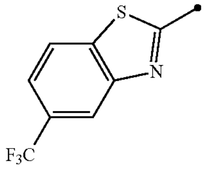 | 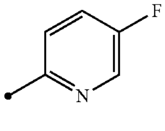 | 261-263 |

TABLE 1-continued
| Compound No. | $R^2$ | $R^4$ | Physical property value |
|---|---|---|---|
| 1-161 | 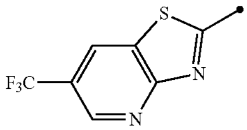 | 4-F-Ph | 290-293 |
| 1-162 | 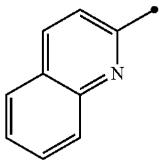 | 4-F-Ph | 215-219 |
| 1-163 | 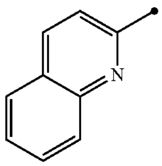 | 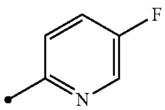 | 242-245 |
| 1-164 | 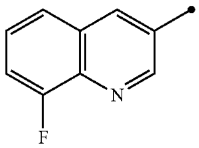 | 4-F-Ph | 232-236 |
| 1-165 | 2-$CF_3$-Ph | 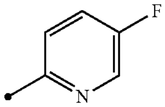 | 216-218 |
| 1-166 | 2-$CF_3$-Ph | 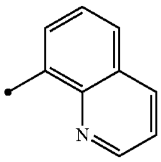 | 224-226 |
| 1-167 | 3-$CF_3$-Ph | 4-F-Ph | 155-157 |
| 1-168 | 3-$CF_3$-Ph | 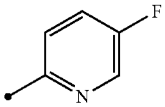 | 179-181 |
| 1-169 | 3-$CF_3$-Ph | 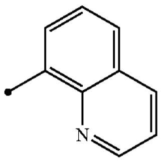 | 202-203 |
| 1-170 | 4-$CF_3$-Ph | Me | 214-217 |
| 1-172 | 4-$CF_3$-Ph | 4-CN-Ph | 206-209 |
| 1-173 | 4-$CF_3$-Ph | 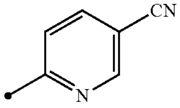 | 203-205 |

TABLE 1-continued
| Compound No. | $R^2$ | $R^4$ | Physical property value |
|---|---|---|---|
| 1-174 | 4-$CF_3$-Ph | 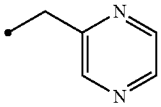 | 149-155 |
| 1-175 | 4-$CF_3$-Ph | 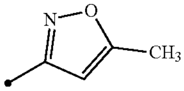 | 242 |
| 1-176 | 3-F-4-$CF_3$-Ph | 4-F-Ph | 97-104 |
| 1-177 | 3,5-$(CF_3)_2$-Ph | Me | 198-200 |
| 1-178 | 3,5-$(CF_3)_2$-Ph | Et | 152-154 |
| 1-179 | 3,5-$(CF_3)_2$-Ph | 4-F-Ph | 188-189 |
| 1-180 | 3-F-Ph | 4-F-Ph | 119-121 |
| 1-181 | 3,4-$Cl_2$-Ph | 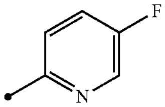 | 223-225 |
| 1-182 | 4-Me-Ph | 4-F-Ph | 180-183 |
| 1-183 | 4-CN-Ph | 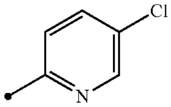 | 222-227 |
| 1-184 | 3-OMe-4-CN-Ph | 4-F-Ph | 149-157 |
| 1-185 | 3-OMe-4-CN-Ph | 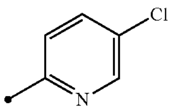 | 210-218 |
| 1-186 | 3,4-$(CN)_2$-Ph | 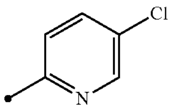 | 196-200 |
| 1-187 | 3-CN-4-Cl-Ph | 4-F-Ph | 149-155 |
| 1-188 | 3-Me-4-CN-Ph | 4-F-Ph | 177-183 |
| 1-189 | 3-Me-4-CN-Ph | 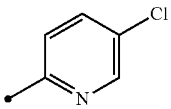 | 206-210 |
| 1-190 | 3-OMe-4-CN-Ph | Me | 204-206 |
| 1-191 | 3-Cl-4-CN-Ph | Me | 215-217 |
| 1-192 | 3-Cl-4-CN-Ph | 4-F-Ph | 202-205 |
| 1-193 | 3-Cl-4-CN-Ph | 4-Me-Ph | 195-197 |
| 1-194 | 3-Cl-4-CN-Ph | 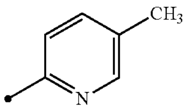 | 250 |
| 1-195 | 3-$CF_3$-4-CN-Ph | Me | 226-228 |
| 1-196 | 3-$CF_3$-4-CN-Ph | 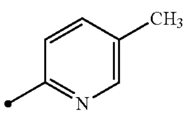 | 230 |

TABLE 1-continued
| Compound No. | $R^2$ | $R^4$ | Physical property value |
| --- | --- | --- | --- |
| 1-197 | 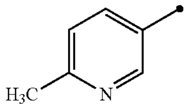 | 4-F-Ph | 124-130 |
| 1-198 | 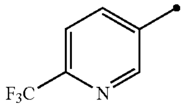 | n-Pr | 180-184 |
| 1-199 | 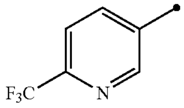 | i-Pr | 190-193 |
| 1-200 | 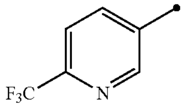 | t-Bu | 194-196 |
| 1-201 | 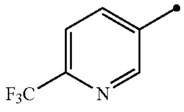 | CH2-t-Bu | 165-170 |
| 1-202 | 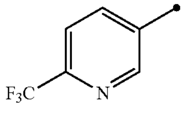 | c-Pen | 165-170 |
| 1-203 | 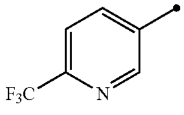 | 3-Me-4-F-Ph | 200-205 |
| 1-204 | 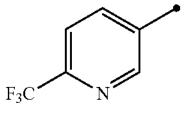 | 4-Me-Ph | 206-209 |
| 1-205 | 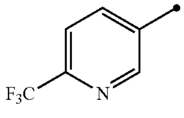 | Et | 177-180 |
| 1-206 | 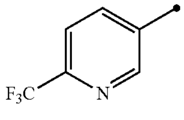 | Me | 250-251 |
| 1-207 | 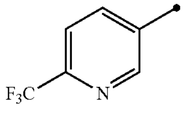 | 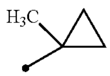 | 190-192 |
| 1-208 | 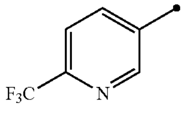 | 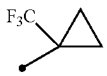 | 150-153 |

TABLE 1-continued
| Compound No. | $R^2$ | $R^4$ | Physical property value |
|---|---|---|---|
| 1-209 | 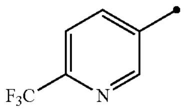 | 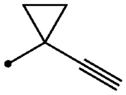 | 136-139 |
| 1-210 | 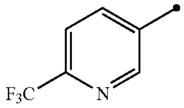 | 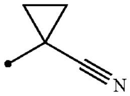 | 105-110 |
| 1-211 | 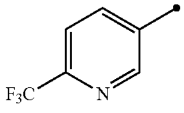 | 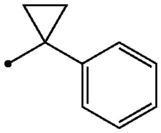 | 201-204 |
| 1-212 | 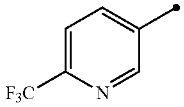 | 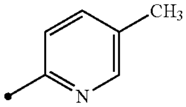 | 217-219 |
| 1-213 | 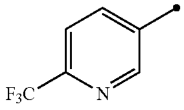 | 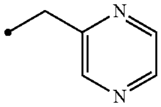 | 199-202 |
| 1-214 | 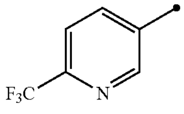 | 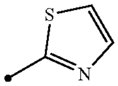 | 260-262 |
| 1-215 | 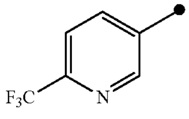 | n-Bu | 192-194 |
| 1-216 | 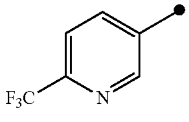 | $CH_2CH_2OCH_3$ | 136-139 |
| 1-217 | 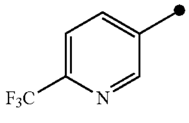 | $CH_2CH_2SCH_3$ | 170-172 |
| 1-218 | 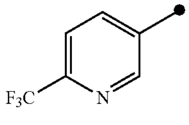 | 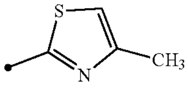 | 256-260 |
| 1-219 | 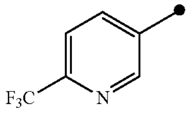 | 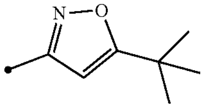 | 271-273 |
| 1-220 | 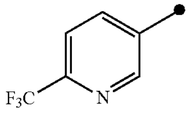 | 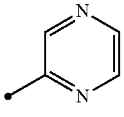 | 240 |

TABLE 1-continued
| Compound No. | $R^2$ | $R^4$ | Physical property value |
|---|---|---|---|
| 1-221 | 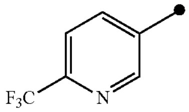 | 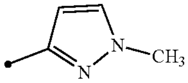 | 250-252 |
| 1-222 | 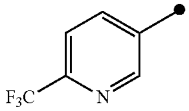 | 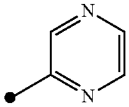 | 212-214 |
| 1-223 | 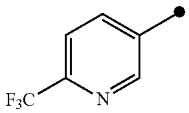 | 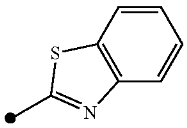 | 239-244 |
| 1-224 | 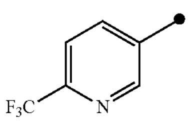 | 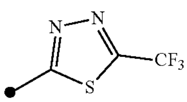 | 245-250 |
| 1-225 | 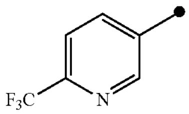 | 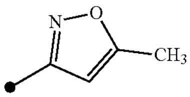 | 208-212 |
| 1-226 | 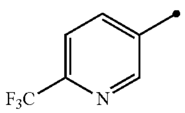 | 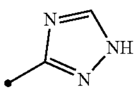 | NMR |
| 1-227 | 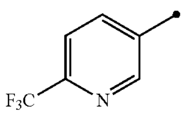 | 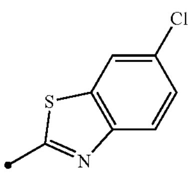 | NMR |
| 1-228 | 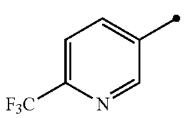 | 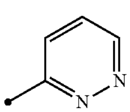 | NMR |
| 1-229 | 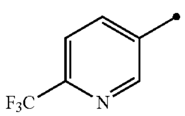 | 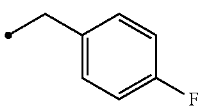 | 208-209 |
| 1-230 | 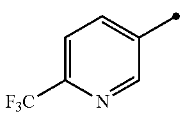 | Bn | 197-199 |
| 1-231 | 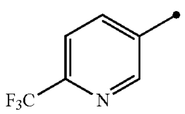 | 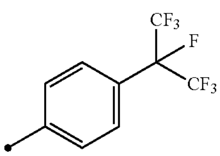 | 177-178 |

TABLE 1-continued
| Compound No. | $R^2$ | $R^4$ | Physical property value |
|---|---|---|---|
| 1-232 | 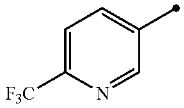 | 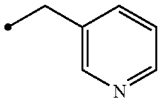 | 223-225 |
| 1-233 | 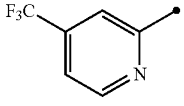 | 4-F-Ph | 173-175 |
| 1-234 | 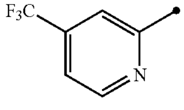 | 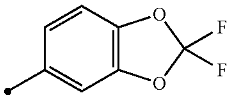 | 165-167 |
| 1-235 | 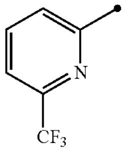 | 4-F-Ph | 200-202 |
| 1-236 | 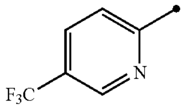 | Me | 207-209 |
| 1-237 | 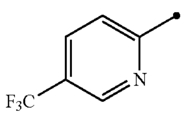 | Et | 157-159 |
| 1-238 | 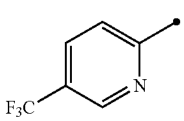 | 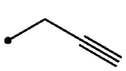 | 140-143 |
| 1-239 | 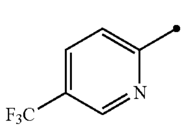 | 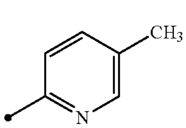 | 233 |
| 1-240 | 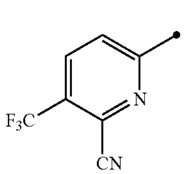 | 4-F-Ph | 156-157 |
| 1-241 | 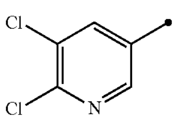 | 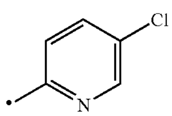 | 222-226 |
| 1-242 | 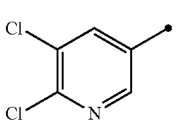 | 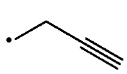 | 231-235 |
| 1-243 | 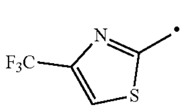 | 4-F-Ph | 157-160 |

TABLE 1-continued
| Compound No. | $R^2$ | $R^4$ | Physical property value |
|---|---|---|---|
| 1-244 | 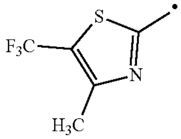 | 4-F-Ph | 168-169 |
| 1-245 | 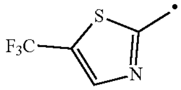 | 4-F-Ph | 223-224 |
| 1-246 | 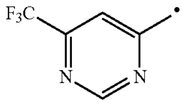 | 4-F-Ph | 218-219 |
| 1-247 . | 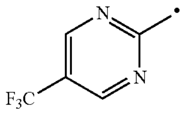 | 4-F-Ph | 195-196 |
| 1-248 | 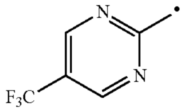 | 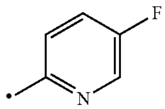 | 229-230 |
| 1-249 | 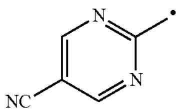 | 4-F-Ph | 278-279 |
| 1-250 | 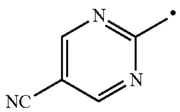 | 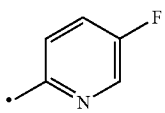 | 255-256 |
| 1-251 | 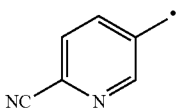 | Me | 240 |
| 1-252 | 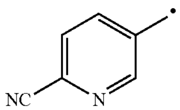 | $CH_2CH_2OCH_3$ | 204-206 |
| 1-253 | 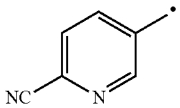 | $CH_2CH_2SCH_3$ | 157-162 |
| 1-254 | 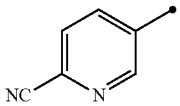 | $CH_2CH(OCH_3)_2$ | 108-111 |
| 1-255 | 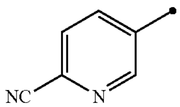 | $CH_2CN$ | 150-152 |
| 1-256 | 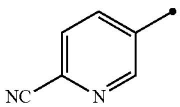 | 3-Me-Ph | 195-200 |

TABLE 1-continued
| Compound No. | $R^2$ | $R^4$ | Physical property value |
|---|---|---|---|
| 1-257 | 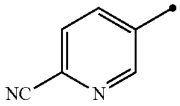 | 4-Me-Ph | 199-203 |
| 1-258 | 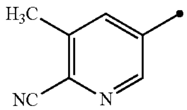 | 4-F-Ph | 206-209 |
| 1-259 | 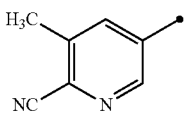 | Me | 250-252 |
| 1-260 | 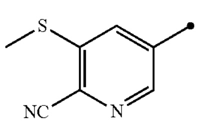 | 4-F-Ph | 188-190 |
| 1-261 | 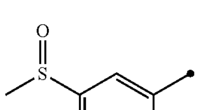 | 4-F-Ph | 225-227 |
| 1-262 | 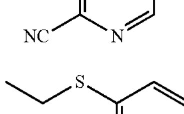 | 4-F-Ph | 168-170 |
| 1-263 | 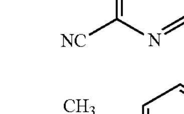 | 4-F-Ph | 185-188 |
| 1-264 | 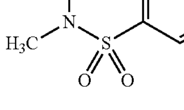 | 4-F-Ph | 240-243 |
| 1-265 | 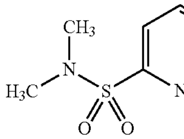 | 4-F-Ph | 223-226 |
| 1-275 | 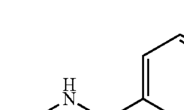 | 4-SMe-Ph | 220-221 |
| 1-276 | 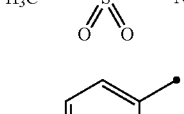 | 4-OEt-Ph | 193-195 |

TABLE 1-continued
| Compound No. | $R^2$ | $R^4$ | Physical property value |
|---|---|---|---|
| 1-277 | 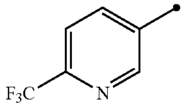 | 4-i-Pr-Ph | 212-214 |
| 1-278 | 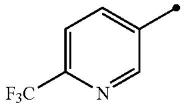 | 4-n-Pen-Ph | 177-179 |
| 1-279 | 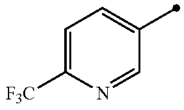 | 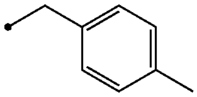 | 213-216 |
| 1-280 | 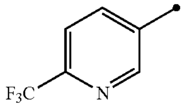 | 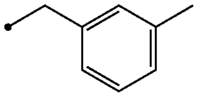 | 189-191 |
| 1-281 | 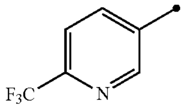 | 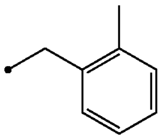 | 132-134 |
| 1-282 | 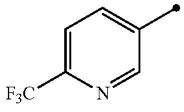 | 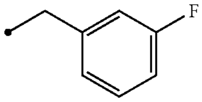 | 192-195 |
| 1-283 | 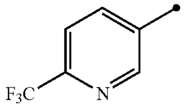 | 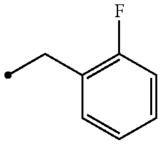 | 176-177 |
| 1-284 | 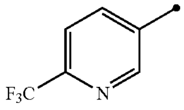 | 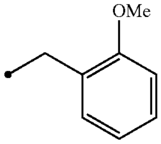 | NMR |
| 1-285 | 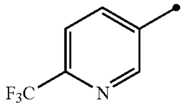 | 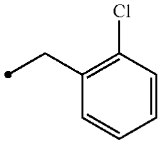 | 177-179 |
| 1-286 | 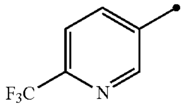 | 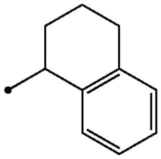 | 132-135 |
| 1-287 | 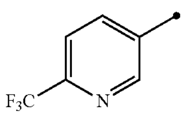 | 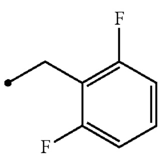 | 196-200 |

TABLE 1-continued
| Compound No. | $R^2$ | $R^4$ | Physical property value |
|---|---|---|---|
| 1-288 | 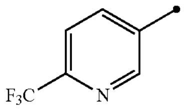 | 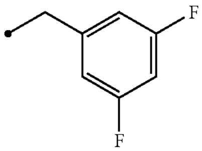 | 177-180 |
| 1-289 | 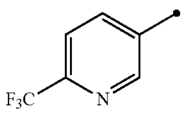 | 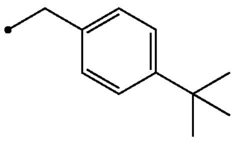 | 131-133 |
| 1-290 | 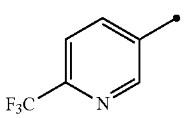 | 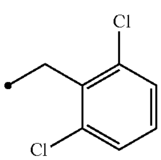 | 176-180 |
| 1-291 | 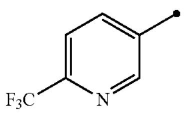 | 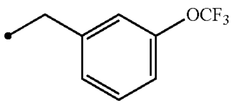 | 135-137 |
| 1-292 | 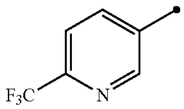 | 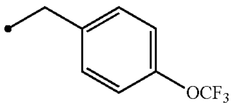 | 181-184 |
| 1-293 | 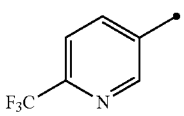 | 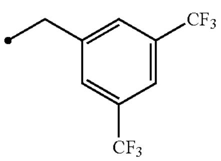 | 197-200 |
| 1-294 | 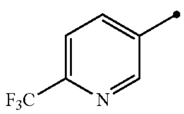 | 4-Cl-Ph | 201-202 |
| 1-295 | 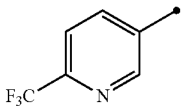 | 4-$OCF_3$-Ph | 184-185 |
| 1-296 | 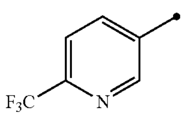 | 4-OH-Ph | 183-184 |
| 1-297 | 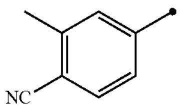 | Me | 186-187 |
| 1-298 | 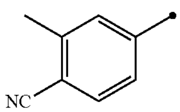 | 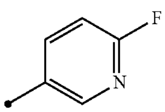 | 213-214 |

TABLE 1-continued
| Compound No. | $R^2$ | $R^4$ | Physical property value |
|---|---|---|---|
| 1-299 | 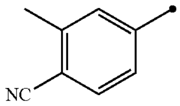 | 3,4-$F_2$-Ph | 189-190 |
| 1-300 | 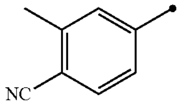 | 3-Me-4-F-Ph | 178-179 |
| 1-301 | 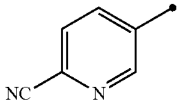 | 4-CN-Ph | 222-225 |
| 1-302 | 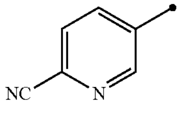 | 3,4-$F_2$-Ph | 216-220 |
| 1-303 | 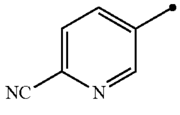 | 3-Me-4-F-Ph | 210-213 |
| 1-304 | 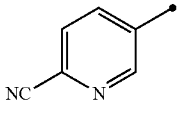 | 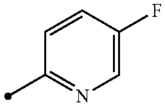 | 217-220 |
| 1-305 | 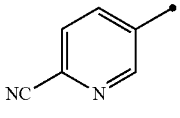 | 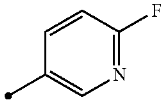 | 187-190 |
| 1-306 | 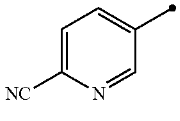 | 3-F-4-Me-Ph | 212-215 |
| 1-307 | 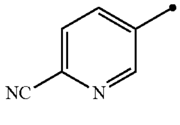 | 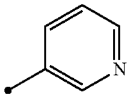 | 225-227 |
| 1-308 | 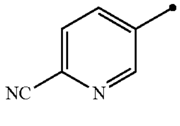 | 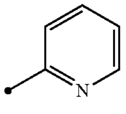 | 200-203 |
| 1-309 | 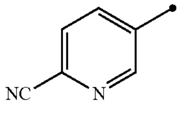 | 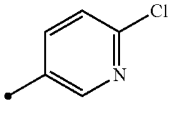 | 218-220 |
| 1-310 | 3-Me-4-CN-Ph | 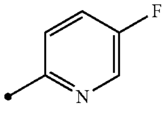 | 207-208 |
| 1-311 | 3-Me-4-CN-Ph | 4-CN-Ph | 196-197 |
| 1-312 | 3-Me-4-CN-Ph | 4-Me-Ph | 190-191 |

TABLE 1-continued
| Compound No. | $R^2$ | $R^4$ | Physical property value |
|---|---|---|---|
| 1-313 | 3-Me-4-CN-Ph | 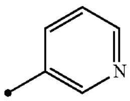 | 218-219 |
| 1-314 | 3-Me-4-CN-Ph | 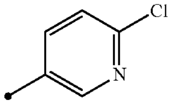 | 246-247 |
| 1-315 | 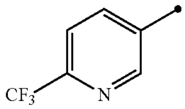 | 3-F-4-Me-Ph | 202-203 |
| 1-316 | 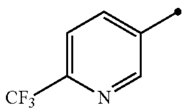 | 4-$CO_2$Me-Ph | 242-243 |
| 1-317 | 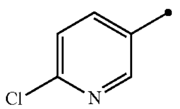 | 3-Me-4-F-Ph | 230-233 |
| 1-318 | 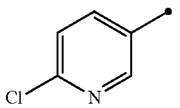 | 4-Me-Ph | 235-238 |
In Table 1, $R^3$ in the general formula (1a) represents a hydrogen atom.
**Sodium salt
[Formula 10]
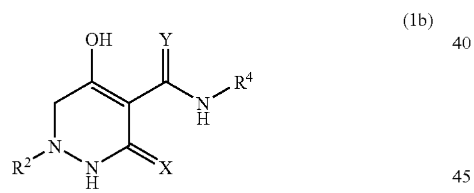
(1b)
TABLE 2
| Compound No. | X | Y | $R^2$ | $R^4$ | Physical property value |
|---|---|---|---|---|---|
| 2-1 | S | O | 4-$CF^3$—Ph | 4-F—Ph | |
| 2-2 | O | S | 4-$CF^3$—Ph | 4-F—Ph | |
| 2-3 | O | S | 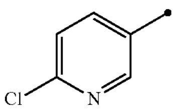 | 4-F—Ph | 230-233 |
| 2-4 | O | S | 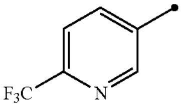 | 4-F—Ph | 180-183 |

TABLE 2-continued
| Compound No. | X | Y | $R^2$ | $R^4$ | Physical property value |
|---|---|---|---|---|---|
| 2-5 | S | O | 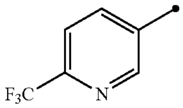 | 4-F—Ph | 182-184 |
| 2-6 | O | S | 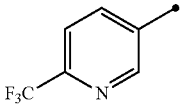 | 4-CN—Ph | 213-217 |
| 2-7 | O | S | 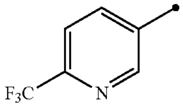 | 4-Me—Ph | 193-197 |
| 2-8 | O | S | 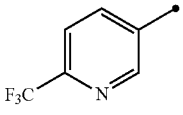 | Ph | 198-202 |
| 2-9 | O | S | 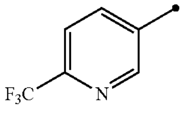 | 3-F—Ph | 195-198 |
| 2-10 | O | S | 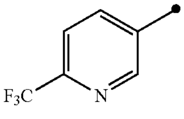 | 4-Cl—Ph | 156-160 |
| 2-11 | O | S | 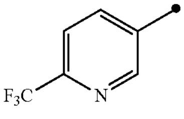 | 4-OMe—Ph | 167-173 |
| 2-12 | O | S | 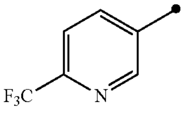 | 4-$NO_2$—Ph | 198-202 |
| 2-13 | O | S | 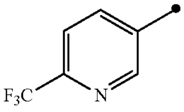 | 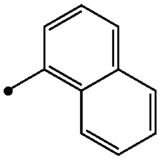 | 102-107 |
| 2-14 | O | S | 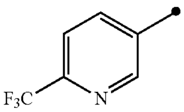 | 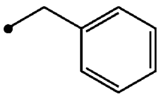 | 148-157 |
| 2-15 | O | S | 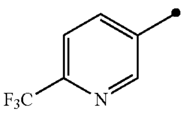 | 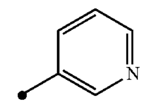 | 160-165 |
| 2-16 | O | S | 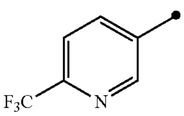 | c-Pr | 189-192 |

TABLE 2-continued
| Compound No. | X | Y | $R^2$ | $R^4$ | Physical property value |
|---|---|---|---|---|---|
| 2-17 | O | S | 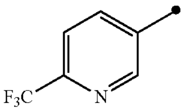 | $CH_2CH{=}CH_2$ | 92-98 |
| 2-18 | O | S | 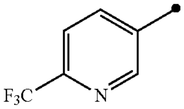 | 3,4-$F_2$—Ph | 134-143 |
| 2-19 | O | S | 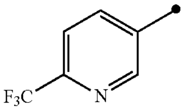 | 4-$CF_3$—Ph | 168-175 |
| 2-20 | O | S | 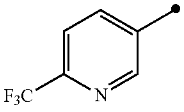 | 2-F—Ph | 75-87 |
[Formula 11]
(1a)
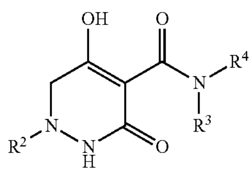
TABLE 3
| Compound No. | $R^2$ | $R^3$ | $R^4$ | Physical property value |
|---|---|---|---|---|
| 3-1 | 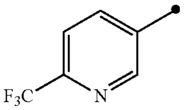 | Me | n-Pr | 185-188 |
| 3-2 | 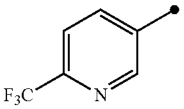 | Me | 4-F—Ph | 152-155 |
[Formula 12]
(13)
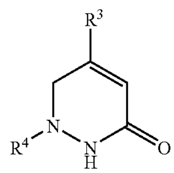
TABLE 4
| Compound No. | $R^2$ | Physical property value |
|---|---|---|
| 4-1 | 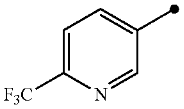 | 122-124 |
| 4-2 | 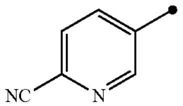 | 164-166 |
| 4-3 | 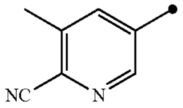 | 217-218 |
| 4-4 | 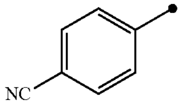 | NMR |
| 4-5 | 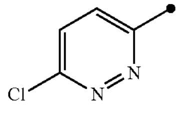 | NMR |
| 4-6 | 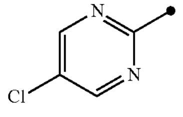 | NMR |
| 4-7 | 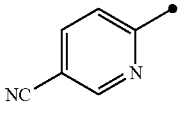 | NMR |

TABLE 4-continued
| Compound No. | $R^2$ | Physical property value |
|---|---|---|
| 4-8 | 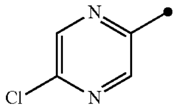 | NMR |
| 4-9 | 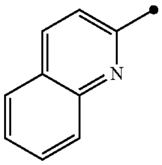 | NMR |
| 4-10 | 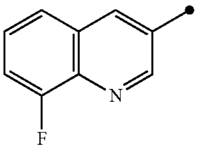 | NMR |
| 4-11 | 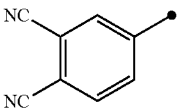 | NMR |
| 4-12 | 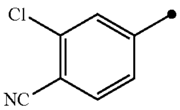 | NMR |
| 4-13 | 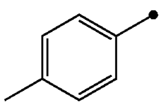 | NMR |
| 4-14 | 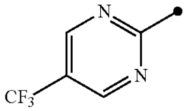 | NMR |
| 4-15 | 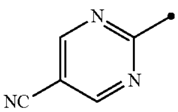 | NMR |
| 4-16 | 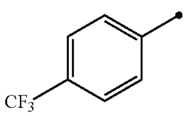 | 140-145 |
| 4-17 | 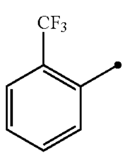 | NMR |
| 4-18 | 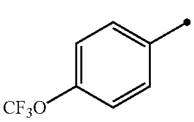 | NMR |
TABLE 4-continued
| Compound No. | $R^2$ | Physical property value |
|---|---|---|
| 4-19 | 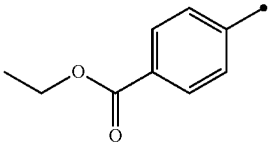 | NMR |
| 4-20 | 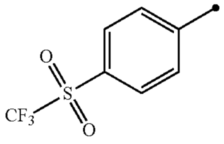 | NMR |
| 4-21 | 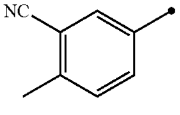 | 200 |
| 4-22 | 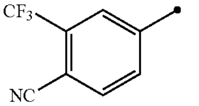 | NMR |
| 4-23 | 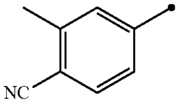 | 198-199 |
| 4-24 | 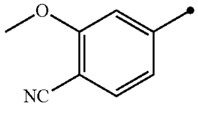 | NMR |
| 4-25 | 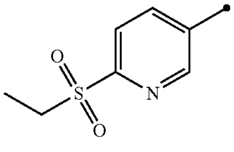 | NMR |
| 4-26 | 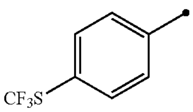 | NMR |
| 4-27 | 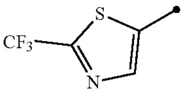 | NMR |
| 4-28 | 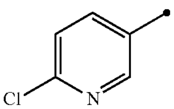 | NMR |
| 4-29 | 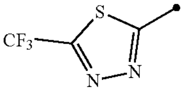 | NMR |
| 4-30 | 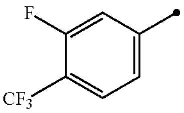 | NMR |

TABLE 4-continued
| Compound No. | $R^2$ | Physical property value |
|---|---|---|
| 4-31 | 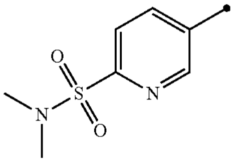 | NMR |
| 4-32 | 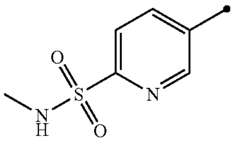 | NMR |
| 4-33 | 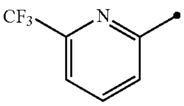 | NMR |
| 4-34 | 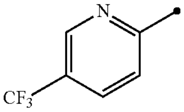 | NMR |
| 4-35 | 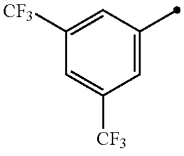 | NMR |
| 4-36 | 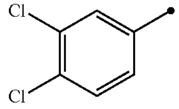 | NMR |
[Formula 13]
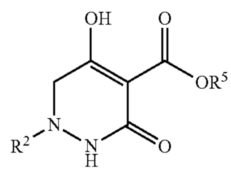
(3a)
TABLE 5
| Compound No. | $R^2$ | $R^5$ | Physical property value |
|---|---|---|---|
| 5-1 | 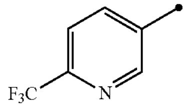 | Et | 175-181 |
| 5-2 | 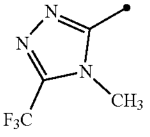 | Et | NMR |
| 5-3 | 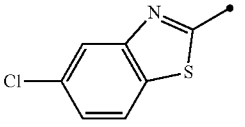 | Et | 171-174 |
| 5-4 | 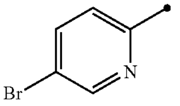 | Et | 174-185 |
| 5-5 | 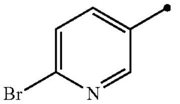 | Et | 172-180 |
| 5-6 | 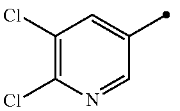 | Et | NMR |
| 5-7 | 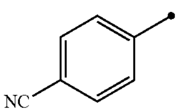 | Et | 165-171 |
| 5-8 | 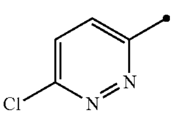 | Et | 180-182 |
| 5-9 | 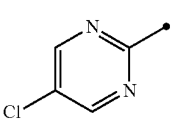 | Et | 155-159 |
| 5-10 | 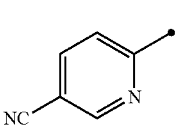 | Et | 178-186 |
| 5-11 | 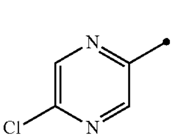 | Et | 177-182 |
| 5-12 | 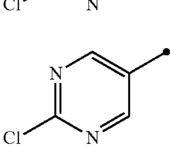 | Et | NMR |
| 5-13 | 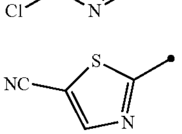 | Et | 168-170 |

TABLE 5-continued
| Compound No. | $R^2$ | $R^5$ | Physical property value |
|---|---|---|---|
| 5-14 | 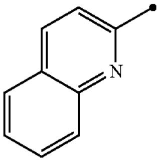 | Et | 166-172 |
| 5-15 | 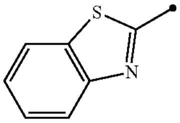 | Et | 178-182 |
| 5-16 | 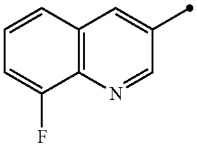 | Et | 184-188 |
| 5-17 | 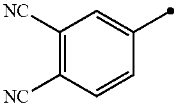 | Et | 176-182 |
| 5-18 | 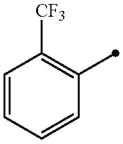 | Et | 130-135 |
| 5-19 | 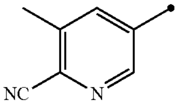 | Et | 178-182 |
| 5-20 | 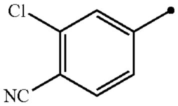 | Et | 201-204 |
| 5-21 | 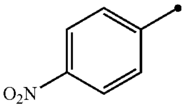 | Et | NMR |
| 5-22 | 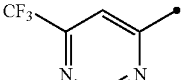 | Et | 161-162 |
| 5-23 | 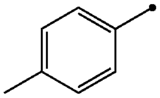 | Et | 161-166 |
| 5-24 | 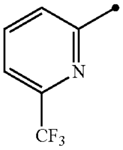 | Et | 176-179 |
TABLE 5-continued
| Compound No. | $R^2$ | $R^5$ | Physical property value |
|---|---|---|---|
| 5-25 | 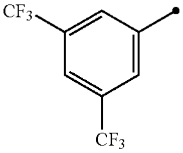 | Et | 120-125 |
| 5-26 | 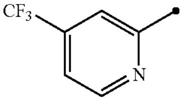 | Et | 158-173 |
| 5-27 | 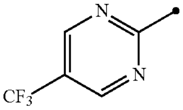 | Et | 147-148 |
| 5-28 | 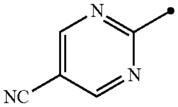 | Et | 169-170 |
| 5-29 | 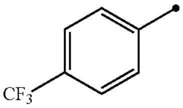 | Et | 148-150 |
| 5-30 | 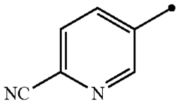 | Et | 171-173 |
| 5-31 | 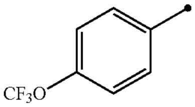 | Et | 156-160 |
| 5-32 | 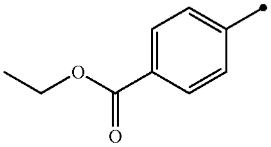 | Et | 152-156 |
| 5-33 | 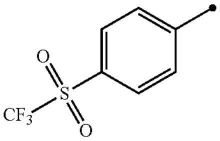 | Et | 170-175 |
| 5-34 | 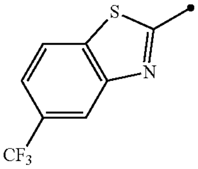 | Et | 168-170 |
| 5-35 | 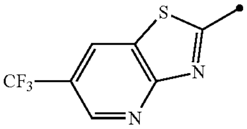 | Et | 197-199 |

TABLE 5-continued
| Compound No. | $R^2$ | $R^5$ | Physical property value |
|---|---|---|---|
| 5-36 | 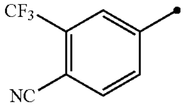 | Et | 192-197 |
| 5-37 | 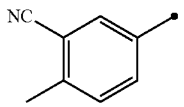 | Et | 160-165 |
| 5-38 | 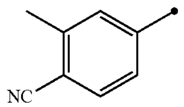 | Et | 180-185 |
| 5-39 | 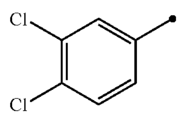 | Et | 168-171 |
| 5-40 | 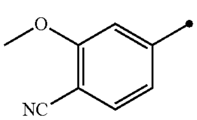 | Et | 167-171 |
| 5-41 | 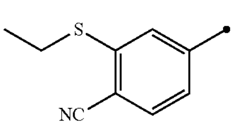 | Et | 170-172 |
| 5-42 | 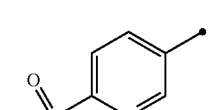 | Et | 167-171 |
| 5-43 | 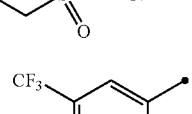 | Et | NMR |
| 5-44 | 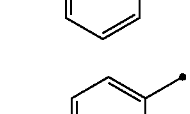 | Et | 181-187 |
| 5-45 | 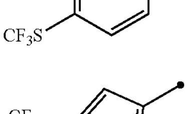 | Et | NMR |
| 5-46 | 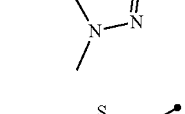 | Et | 157-160 |
| 5-47 | 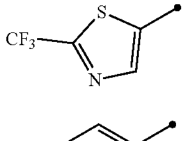 | Et | NMR |
TABLE 5-continued
| Compound No. | $R^2$ | $R^5$ | Physical property value |
|---|---|---|---|
| 5-48 | 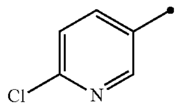 | Et | 165-173 |
| 5-49 | 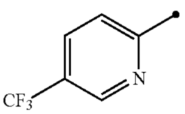 | Et | NMR |
| 5-50 | 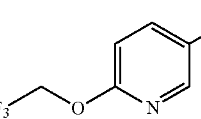 | Et | NMR |
| 5-51 | 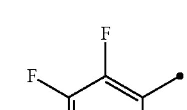 | Et | NMR |
| 5-52 | 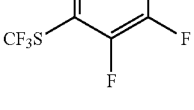 | Et | 125-126 |
| 5-53 | 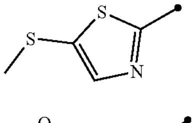 | Et | 148-149 |
| 5-54 | 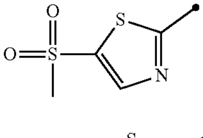 | Et | 102-103 |
| 5-55 | 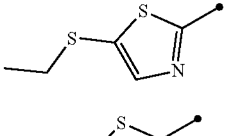 | Et | NMR |
| 5-56 | 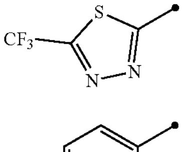 | Et | NMR |
| 5-57 | 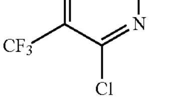 | Et | 138-142 |
| 5-58 | 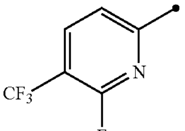 | Et | NMR |

TABLE 5-continued

| Compound No. | $R^2$ | $R^5$ | Physical property value |
|---|---|---|---|
| 5-59 | 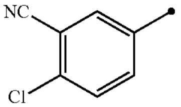 | Et | NMR |
| 5-60 | 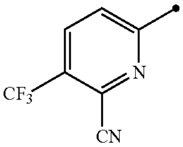 | Et | NMR |
| 5-61 | 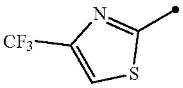 | Et | NMR |
| 5-62 | 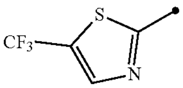 | Et | NMR |
| 5-63 | 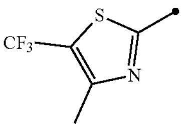 | Et | NMR |
| 5-64 | 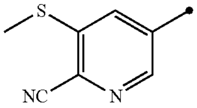 | Et | NMR |

TABLE 5-continued

| Compound No. | $R^2$ | $R^5$ | Physical property value |
|---|---|---|---|
| 5-65 | 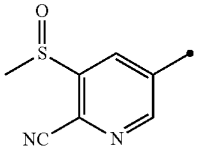 | Et | NMR |
| 5-66 | 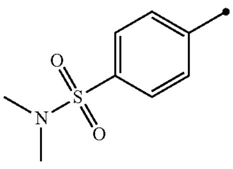 | Et | NMR |
| 5-67 | 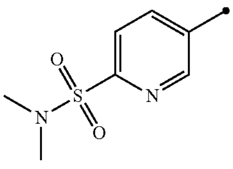 | Et | NMR |
| 5-68 | 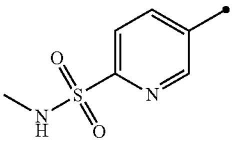 | Et | 180-184 |

TABLE 6

| Compound No. | $^1$H-NMR data |
|---|---|
| 1-226 | δ (DMSO-$d_6$/TMS, ppm) 13.2 (br, 1H), 10.4 (br, 1H), 8.60 (m, 1H), 8.29 (s, 1H), 7.81-7.75 (m, 1H), 7.68-7.62 (m, 1H), 5.36 (s, 2H), 4.43 (br, 1H) |
| 1-227 | δ (DMSO-$d_6$/TMS, ppm) 12.8 (br, 1H), 8.64 (d, 1H), 8.14 (d, 1H), 7.84 (m, 1H), 7.76-7.71 (m, 2H), 7.47 (dd, 1H), 4.62 (br, 2H) |
| 1-228 | δ (DMSO-$d_6$/TMS, ppm) 12.1 (s, 1H), 9.02 (m, 1H), 8.65 (d, 1H), 8.23 (dd, 1H), 7.85 (m, 1H), 7.75-7.72 (m, 2H), 4.76 (s, 2H) |
| 1-284 | δ (DMSO-$d_6$/TMS, ppm) 10.93 (br, 1H), 8.57 (br, 1H), 7.81 (d, 1H), 7.28-6.88 (m, 6H), 4.69-4.41 (m, 2H), 4.42-4.41 (m, 2H), 3.82 (s, 3H) |
| 4-4 | δ ($CDCl_3$/TMS, ppm) 7.68 (br, 1H), 7.65 (d, 2H), 7.07 (d, 2H), 4.31 (s, 2H), 3.31 (s, 2H) |
| 4-5 | δ (CDCl3/TMS, ppm) 7.49 (d, 2H), 7.39 (d, 2H), 4.77 (s, 2H), 3.33 (s, 2H) |
| 4-6 | δ ($CDCl_3$/TMS, ppm) 8.43 (s, 2H), 8.29 (br, 1H), 4.65 (s, 2H), 3.40 (s, 2H) |
| 4-7 | δ ($CDCl_3$/TMS, ppm) 8.53 (dd, 1H), 8.25 (br, 1H), 7.90 (dd, 1H), 7.16 (dd, 2H), 4.72 (s, 2H), 3.35 (s, 2H) |
| 4-8 | δ ($CDCl_3$/TMS, ppm) 8.3 (s, 1H), 8.20 (s, 1H), 8.11 (br, 1H), 4.58 (s, 2H), 3.33 (s, 2H) |
| 4-9 | δ (CDCl3/TMS, ppm) 8.15 (d, 1H), 7.82 (br, 1H), 7.75 (d, 1H), 7.66 (dd, 1H), 7.43 (dd, 1H), 7.32(d, 1H), 4.76 (s, 2H), 3.29 (s, 2H) |
| 4-10 | δ ($CDCl_3$/TMS, ppm) 8.83 (d, 1H, J = 2.8 Hz), 7.72 (br, 1H), 7.64-7.63 (m, 1H), 7.53-7.50 (m, 2H), 7.34-7.29 (m, 1H), 4.41 (s, 2H), 3.35 (s, 2H) |
| 4-11 | δ ($CDCl_3$/TMS, ppm) 7.77 (d, 1H), 7.70 (br, 1H), 7.39 (d, 1H), 7.28 (d, 1H), 4.33 (s, 2H), 3.36 (s, 2H) |
| 4-12 | δ ($CDCl_3$/TMS, ppm) 7.64 (d, 1H), 7.61 (br, 1H), 7.13 (d, 1H), 6.94 (d, 1H), 4.29 (s, 2H), 3.34 (s, 2H) |
| 4-13 | δ ($CDCl_3$/TMS, ppm) 7.66 (br, 1H), 7.14 (d, 2H), 6.88 (d, 2H), 4.20 (s, 2H), 3.25 (s, 2H), 2.29 (s, 3H) |

TABLE 6-continued

| Compound No. | $^1$H-NMR data |
|---|---|
| 4-14 | δ ($CDCl_3$/TMS, ppm) 8.70 (s, 2H), 8.47 (br, 1H), 4.75 (s, 2H), 3.47 (s, 2H) |
| 4-15 | δ ($CDCl_3$/TMS, ppm) 8.70 (s, 2H), 8.39 (br, 1H), 4.76 (s, 2H), 3.50 (s, 2H) |
| 4-17 | δ ($CDCl_3$/TMS, ppm) 7.71 (br, 1H), 7.56 (t, 1H), 7.49 (br, 1H), 7.31 (t, 1H), 7.23 (d, 1H), 4.10 (s, 2H), 3.52 (s, 2H) |
| 4-18 | δ ($CDCl_3$/TMS, ppm) 7.60 (br, 1H), 7.21 (d, 2H), 7.00 (d, 2H), 4.33 (s, 2H), 3.29 (s,2H) |
| 4-19 | δ ($CDCl_3$/TMS, ppm) 8.03 (d, 2H), 7.83 (br, 1H), 7.02 (d, 2H), 4.36 (q, 2H), 4.30 (s, 2H), 3.28 (s, 2H), 1.38 (t, 3H) |
| 4-20 | δ ($CDCl_3$/TMS, ppm) 7.99 (d, 2H), 7.73 (br, 1H), 7.20 (d, 2H), 4.38 (s, 2H), 3.38 (s, 2H) |
| 4-22 | δ ($CDCl_3$/TMS, ppm) 7.80 (d, 1H), 7.67 (br, 1H), 7.35 (d, 1H), 7.21 (d, 1H), 4.35 (s, 2H), 3.36 (s, 2H) |
| 4-24 | δ ($CDCl_3$/TMS, ppm) 7.55 (br, 1H), 7.52 (d, 1H), 6.57 (d, 1H), 6.54 (dd, 1H), 4.29 (s, 2H), 3.93 (s, 3H), 3.33 (s, 2H) |
| 4-25 | δ ($CDCl_3$/TMS, ppm) 8.48 (d, 1H), 8.05 (d, 1H), 7.86 (br, 1H), 7.48 (dd, 1H), 4.35 (s, 2H), 3.37 (q, 2H), 3.36(s. 2H), 1.37 (t, 3H) |
| 4-26 | δ ($CDCl_3$/TMS, ppm) 7.85 (br, 1H), 7.63 (d, 2H), 7.03 (d, 2H), 4.28 (s, 2H), 3.31 (s, 2H) |
| 4-27 | δ ($CDCl_3$/TMS, ppm) 7.23 (s, 1H), 4.16 (s, 2H), 3.48 (s, 2H) |
| 4-28 | δ ($CDCl_3$/TMS, ppm) 8.16 (dd, 1H), 7.71 (br, 1H), 7.34-7.29 (m, 2H), 4.24 (s, 2H), 3.32 (s, 2H) |
| 4-29 | δ ($CDCl_3$/TMS, ppm) 4.66 (s, 2H), 3.51 (s, 2H) |
| 4-30 | δ ($CDCl_3$/TMS, ppm) 7.55 (t, 1H), 7.47(dd, 1H), 6.82 (m, 1H), 4.27 (s, 2H), 3.31 (s, 2H) |
| 4-31 | δ ($CDCl_3$/TMS, ppm) 8.45 (d, 1H), 7.92 (d, 1H), 7.63 (br, 1H), 7.46 (dd, 1H), 4.33 (s, 2H), 3.36 (s, 2H), 2.93 (s, 6H) |
| 4-32 | δ ($CDCl_3$/TMS, ppm) 8.47 (d, 1H), 7.99 (d, 1H), 7.46 (dd, 1H), 4.34 (s, 2H), 3.36 (s, 2H), 2.75 (d, 3H) |
| 4-33 | δ ($CDCl_3$/TMS, ppm) 8.07 (br, 1H), 7.85 (t, 1H), 7.29-7.28 (m, 2H), 4.69 (s, 2H), 3.31 (s, 2H) |
| 4-34 | δ ($CDCl_3$/TMS, ppm) 8.90 (br, 1H), 8.50 (s, 1H), 7.88 (dd, 1H), 7.17 (d,1H), 4.72 (s, 2H), 3.31 (s, 2H) |
| 4-35 | δ ($CDCl_3$/TMS, ppm) 7.98 (br, 1H), 7.52 (s, 1H), 7.40 (s, 2H), 4.33 (s, 2H), 3.34 (s, 2H) |
| 4-36 | δ ($CDCl_3$/TMS, ppm) 8.06 (br, 1H), 7.39 (d, 1H), 7.10 (d, 1H), 6.83 (dd, 1H), 4.21 (s, 2H), 3.29 (s, 2H) |
| 5-2 | δ ($CDCl_3$/TMS, ppm) 13.89 (s, 1H), 4.40 (2H, s), 4.35 (q, 2H), 1.56 (s, 3H), 1.32 (t, 3H) |
| 5-6 | δ ($CDCl_3$/TMS, ppm) 13.98-13.95 (m, 1H), 8.10 (d, 1H), 7.53-7.52 (m, 1H), 7.08 (s, 1H), 4.45-4.37 (m, 4H), 1.39 (t, 3H) |
| 5-12 | δ ($CDCl_3$/TMS, ppm) 13.95 (s, 1H), 8.45-8.44 (m, 2H), 7.72 (s, 1H), 4.44 (s, 2H), 4.38 (q, 2H), 1.41-1.37 (m, 3H) |
| 5-21 | δ ($CDCl_3$/TMS, ppm) 13.96 (s, 1H), 8.22-8.19 (m, 2H), 7.26 (s, 1H), 7.16-7.13 (m, 2H), 4.57 (s, 2H), 4.37 (q, 2H), 1.38 (t, 3H) |
| 5-43 | δ ($CDCl_3$/TMS, ppm) 13.9 (br, 1H), 7.52-7.6 (m, 2H), 7.31-7.22 (m, 2H), 4.49 (s,2H), 4.38 (q, 2H), 1.37 (t, 3H) |
| 5-45 | δ ($CDCl_3$/TMS, ppm) 13.98 (bs, 1H), 6.25 (s, 1H), 4.47 (s, 2H), 4.36 (q, 2H), 3.83 (s, 3H), 1.38 (t, 3H) |
| 5-47 | δ ($CDCl_3$/TMS, ppm) 13.92-13.89 (m, 1H), 8.19 (d, 1H), 7.60-7.56 (m, 1H), 7.21-7.18 (m, 1H), 7.10-7.07 (m, 1H), 4.87 (s, 2H), 4.34 (q, 2H), 1.38-1.34 (m, 3H) |
| 5-49 | δ ($CDCl_3$/TMS, ppm) 13.95(s, 1H), 8.50(dd, 1H), 7.82(dd, 1H), 7.41 (br, 1H), 7.21 (d, 1H), 4.97 (s, 2H), 4.35 (q, 2H), 1.36 (t, 3H) |
| 5-50 | δ ($CDCl_3$/TMS, ppm) 13.86 (s, 1H), 7.39 (dd, 1H), 7.41 (dd, 1H), 7.01 (br, 1H), 6.83 (dd, 1H), 4.71 (s, 2H), 4.38 (q, 2H), 1.39 (t, 3H). |
| 5-51 | δ ($CDCl_3$/TMS, ppm) 14.02 (s, 1H), 7.17 (s, 1H), 4.36 (s, 2H), 4.34-4.29 (m, 2H), 2.36 (s, 2H), 1.40 (t, 3H) |
| 5-55 | δ ($CDCl_3$/TMS, ppm) 14.23-14.12 (m, 1H), 8.33 (s, 1H), 4.89 (s, 2H), 4.39 (q, 2H), 1.39 (t, 3H) |
| 5-56 | δ (DMSO-$d_6$/TMS, ppm) 8.09 (d, 1H), 8.00 (d, 1H), 4.33 (q, 2H), 4.20 (s, 2H), 1.33 (t, 3H) |
| 5-58 | δ ($CDCl_3$/TMS, ppm) 13.9 (br, 1H), 7.78-7.57 (m, 2H), 6.82-6.69 (m, 2H), 4.45 (s, 2H), 4.36 (q, 2H), 1.38 (t, 3H) |
| 5-59 | δ ($CDCl_3$/TMS, ppm) 14.0 (br, 1H), 7.42 (d, 1H), 7.34 (d, 1H), 7.22 (dd, 1H), 4.45 (s, 2H), 4.37 (q, 2H), 1.39 (t, 3H) |
| 5-60 | δ ($CDCl_3$/TMS, ppm) 8.25 (d, 1H), 7.37 (d, 1H), 4.68 (s, 2H), 4.15 (q, 2H), 1.19 (t, 3H) |
| 5-61 | δ (DMSO-$d_6$/TMS, ppm) 14.07 (bs, 1H), 9.44 (bs, 1H), 7.24 (s, 1H), 4.80 (s, 2H), 4.38 (q, 2H), 1.38 (t, 3H) . |
| 5-62 | δ (DMSO-$d_6$/TMS, ppm) 14.12 (bs, 1H), 9.60 (bs, 1H), 7.61 (q, 1H), 4.80 (s, 2H), 4.38 (q, 2H), 1.39 (t, 3H) |
| 5-63 | δ ($CDCl_3$/TMS, ppm) 14.09 (bs, 1H), 9.53 (bs, 1H), 4.76 (s, 2H), 4.38 (q, 2H), 2.38 (q, 3H), 1.39 (t, 3H) |

TABLE 6-continued

| Compound No. | $^1$H-NMR data |
|---|---|
| 5-64 | δ (DMSO-$d_6$/TMS, ppm) 8.25(d, 1H), 7.37(d, 1H), 4.68 (s, 2H), 4.15 (q, 2H), 1.19 (t, 3H) |
| 5-65 | δ (DMSO-$d_6$/TMS, ppm) 10.90 (br, 1H), 8.65(d, 1H), 7.84 (d, 1H), 4.75 (s, 2H), 4.15 (q, 2H), 1.20 (t, 3H) |
| 5-66 | δ (DMSO-$d_6$/TMS, ppm) 9.12 (br, 1H), 7.65 (d, 1H), 6.90 (d, 1H), 4.37 (s, 2H), 4.26 (q, 2H), 2.65 (s, 6H), 1.27 (t, 3H) |
| 5-67 | δ (DMSO-$d_6$/TMS, ppm) 10.02 (br, 1H), 8.59 (d, 1H), 8.10 (d, 1H), 7.20 (q, 1H), 4.87 (s, 2H), 4.13 (q, 2H), 1.18 (t, 3H) |

The agricultural and horticultural insecticidal agent comprising the compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, other pests such as nematodes, etc.

Examples of the above pests or nematodes include the following.

Examples of the species of the order Lepidoptera include *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura*, a species of the family Tortricidae (*Eucosma aporema*), *Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina* sp., *Carposina niponensis, Conogethes punctiferalis, Synanthedon* sp., *Lyonetia clerkella, Papilio helenus, Colias erate poliographus, Phalera flavescens*, the species of the family Pieridae such as *Pieris rapae crucivora* and *Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis*.

Examples of the species of the order Hemiptera include *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai,*

*Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatellus, Eurydema pulchrum, Cletus trigonus, Clovia punctata, Empoasca sp., Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii.*

Examples of the species of the order Coleoptera include *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis.*

Examples of the species of the order Diptera include *Culex pipiens pallens, Pegomya hyoscyami, Liriomyza huidobrensis, Musca domestica, Chlorops oryzae, Hydrellia sasakii, Agromyza oryzae, Hydrellia griseola, Ophiomyia phaseoli, Dacus cucurbitae, Drosophila suzukii, Rhacochlaena japonica, Muscina stabulans*, the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella.*

Examples of the species of the order Hymenoptera include *Pristomyrmex pungens*, the species of the family *Bethylidae, Monomorium pharaonis, Pheidole noda, Athalia rosae, Dryocosmus kuriphilus, Formica fusca japonica*, the species of the subfamily Vespinae, *Athalia infumata infumata, Arge pagana, Athalia japonica, Acromyrmex* spp., *Solenopsis* spp., *Arge mali* and *Ochetellus glaber.*

Examples of the species of the order Orthoptera include *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma.*

Examples of the species of the order Thysanoptera include *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Franklinella occidentalis, Thrips palmi, Frankliniella lilivora* and *Liothrips vaneeckei.*

Examples of the species of the order Acari include *Leptotrombidium akamushi, Tetranychus ludeni, Dermacentor variabilis, Tetranychus truncatus, Ornithonyssus bacoti, Demodex canis, Tetranychus viennensis, Tetranychus kanzawai*, the species of the family Ixodidae such as *Rhipicephalus sanguineus, Cheyletus malaccensis, Tyrophagus putrescentiae, Dermatophagoides farinae, Latrodectus hasseltii, Dermacentor taiwanensis, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.

Examples of the species of the order Isoptera include *Reticulitermes miyatakei, Incisitermes minor, Coptotermes formosanus, Hodotermopsis japonica, Reticulitermes* sp., *Reticulitermes flaviceps amamianus, Glyptotermes kushime-*

*nsis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus.*

Examples of the species of the order Blattodea include *Periplaneta fuliginosa, Blattella germanica, Blatta orientalis, Periplaneta brunnea, Blattella lituricollis, Periplaneta japonica* and *Periplaneta americana.*

Examples of the species of the order Siphonaptera include *Pulex irritans, Ctenocephalides felis* and *Ceratophyllus gallinae.*

Examples of the species of the phylum Nematoda include *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans.*

Examples of the species of the phylum Mollusca include such as *Pomacea canaliculata, Achatina fulica, Meghimatium bilineatum, Lehmannina valentiana, Limax flavus* and *Acusta despecta sieboldiana.*

In addition, the agricultural and horticultural insecticide of the present invention has a strong insecticidal effect on *Tuta absoluta* as well.

Further, mites and ticks parasitic on animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanensis; Dermanyssus gallinae*; the species of the genus *Ornithonyssus* such as *Ornithonyssus sylviarum* and *Ornithonyssus* bursa; the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai*; the species of the family Cheyletidae such as *Cheyletiella yasguri, Cheyletiella parasitivorax* and *Cheyletiella blakei*; the species of the superfamily Sarcoptoidea such as *Psoroptes cuniculi, Chorioptes bovis, Otodectes cynotis, Sarcoptes scabiei* and *Notoedres cati*; and the species of the family Demodicidae such as *Demodex canis.*

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Monopsyllus anisus.*

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum*. In addition, examples of endoparasites include nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis; trematodes* such as *Schistosoma japonicum* and *Fasciola hepatica*; and protozoa such as coccidia, *Plasmodium*, intestinal *Sarcocystis, Toxoplasma* and *Cryptosporidium.*

The agricultural and horticultural insecticidal and acaricidal agent comprising the compound represented by the general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticidal agent is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticidal agent utilizes so-called penetration and translocation. That is, nursery soil, soil in transplanting holes, plant foot, irrigation water, cultivation water in hydroponics, or the like is treated with the agricultural and horticultural insecticidal and acaricidal agent to allow crops, ornamental flowering plants, etc. to absorb the compound of the present invention through the roots via soil or otherwise.

Examples of useful plants to which the agricultural and horticultural insecticidal agent of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., *chrysanthemum*, rose, carnation, orchid, tulip, lily, etc.), garden trees (e.g., ginkgo trees, cherry trees, Japanese *aucuba*, etc.) and forest trees (e.g., *Abies sachalinensis, Picea jezoensis*, pine, yellow cedar, Japanese cedar, hinoki cypress, *eucalyptus*, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticidal agent of the present invention can be applied to these plants as well.

Further, exemplary toxins expressed in genetically modified plants include insecticidal proteins of *Bacillus cereus* or *Bacillus popilliae; Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, CrylFa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticidal agent of the present invention can be used in combination or used systematically.

In order to control target pests, the agricultural and horticultural insecticidal agent of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticidal agent of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of an agrochemical and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticidal agent of the present invention is commonly used as a formulation convenient for application, which is prepared by the usual method for preparing agrochemical formulations.

That is, the compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticidal agent or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and THF; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated aliphatic hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticidal agent of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticidal agent).

The application rate of the agricultural and horticultural insecticidal agent of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural and horticultural insecticidal agent of the present invention can be used after mixed with other agricultural and horticultural insecticidal agent, acaricides, nematicides, microbicides, biopesticides and/or the like. Further, the agricultural and horticultural insecticidal and acaricidal agent can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), fenobucarb (BPMC), Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, acynonapyr, azinphos-methyl, acequinocyl, acetamiprid, acetoprole, acephate, abamectin, afidopyropen, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isocycloseram, isofenphos, isoprocarb (MIPC), epsilon-metofluthrin, epsilon-momfluorothrin, ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxazosulfyl, oxamyl, oxydemeton-methyl, oxydeprofos (ESP), oxibendazole, oxfendazole, potassium oleate, sodium oleate, cadusafos, kappa-bifenthrin, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, chloroprallethrin, kelthane (dicofol), salithion, cyhalodiamide, cyanophos (CYAP), diafenthiuron, diamidafos, cyantraniliprole, theta-cypermethrin, dienochlor, cyetpyrafen, cyenopyrafen, dioxabenzofos, diofenolan, sigma-cypermethrin, cyclaniliprole, dichlofenthion (ECP), cycloprothrin, dichlorvos (DDVP), dicloromezotiaz, disulfoton, dinotefuran, cyhalodiamide, cyhalothrin, cyphenothrin, cyfluthrin, diflubenzuron, cyflumetofen, diflovidazin, cyproflanilide, cyhexatin, cypermethrin, dimethylvinphos, dimethoate, dimpropyridaz, dimefluthrin, silafluofen, cyromazine, spidoxamat, spinetoram, spinosad, spirodiclofen, spirotetramat, spiropidion, spiromesifen, sulfluramid, sulprofos, sulfoxaflor, zeta-cypermethrin, diazinon, tau-fluvalinate, dazomet, thiacloprid, thiamethoxam, tioxazafen, thiodicarb, thiocyclam, thiosultap, thiosultap-sodium, thionazin, thiometon, deet, dieldrin, tetrachlorantraniliprole, tyclopyrazoflor, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, doramectin, tralopyril, tralomethrin, transfluthrin, triazamate, triazuron, trichlamide, trichlorphon (DEP), triflumezopyrium, triflumuron, tolfenpyrad, naled (BRP), nicofluprole, nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, pyflubumide, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pyriminostrobin, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fenmezoditiaz, fosthiazate, formetanate, butathiofos, buprofezin, furathiocarb, prallethrin, fluacrypyrim, fluazaindolizine, fluazinam, fluazuron, fluensulfone, fluxametamide, fluchlordiniliprole, flucycloxuron, flucythrinate, fluvalinate, flupyradifurone, flufiprole, flupyradifurone, flupyrazofos, flupyrimin, flufenerim, flufenoxystrobin, flufenoxuron, flufenzine, flufenprox, fluproxyfen, flubrocythrinate, fluhexafon, flubendiamide, flupentiofenox, flumethrin, flurimfen, prothiofos, protrifenbute, flonicamid, propaphos, propargite (BPPS), profenofos, broflanilide, profluthrin, propoxur (PHC), flometoquin, alpha-bromadiolone, bromopropylate, beta-cyfluthrin, hexaflumuron, hexythiazox, heptafluthrin, heptenophos, permethrin, benclothiaz, bendiocarb, benzpyrimoxan, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, momfluorothrin, lambda-cyhalothrin, ryanodine, lufenuron, rescalure, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Exemplary agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isofetamid, isoflucypram, isoprothiolane, ipconazole, ipfentrifluconazole, ipflufenoquin, iprodione, iprovalicarb, iprobenfos, imazalil, iminoctadine, metam, iminoctadine-albesilate, iminoctadine-triacetate, imibenconazole, inpyrfluxam, uniconazole, uniconazole-P, echlomezole, edifenphos, etaconazole, ethaboxam, ethirimol, etem, ethoxyquin, etridiazole, enestroburin, enoxastrobin, epoxiconazole, oxadixyl, oxathiapiprolin, oxycarboxin, copper-8-quinolinolate, oxytetracycline, copper-oxinate, oxpoconazole, oxpoconazole-fumarate, oxolinic acid, octhilinone, ofurace, orysastrobin, carbam (metam-sodium), kasugamycin, carbamorph, carpropamid, carbendazim, carboxin, carvone, quinazamid, quinacetol, quinoxyfen, quinofumelin, chinomethionat (quinomethionate), captafol, captan, kiralaxyl, quinconazole, quintozene, guazatine, cufraneb, cuprobam, coumoxystrobin, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chloroinconazide, chlorodinitronaphthalene, chlorothalonil, chloroneb, salicylanilide, zarilamid, cyazofamid, diethyl pyrocarbonate, diethofencarb, cyclafuramid, diclocymet, dichlozoline, diclobutrazol, cyclobutrifluram, dichlofluanid, cycloheximide, dichlobentiazox, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipymetitrone, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thifluzamide, thicyofen, thioquinox, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, triclopyricarb, tricyclazole, triticonazole, tridemorph, tributyltin oxide, triflumizole, trifloxystrobin, triforine, tolylfluanid, tolclofos-methyl, tolprocarb, natamycin, nabam, nitrostyrene, nitrothal-isopropyl, nuarimol, copper nonylphenol sulfonate, halacrinate, validamycin, valifenalate, harpin protein, picarbutrazox, bixafen, picoxystrobin, picobenzamide, pydiflumetofen, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyraziflumid, pyrazophos, pyrapropoyne, pyrametostrobin, pyriofenone, pyridinitril, pydiflumetofen, pyrisoxazole, pyridachlometyl, pyrifenox, pyribencarb, pyriminostrobin, pyrimethanil, pyroxychlor, pyroxyfur, pyroquilon, vinclozolin, ferbam, famoxadone, fenapanil, fenamidone, fenaminosulf, fenaminstrobin, fenarimol, fenitropan, fenoxanil, ferimzone, ferbam, fentin, fenpiclonil, fenpicoxamid, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluindapyr, fluoxastrobin, fluoxapiprolin, fluoxytioconazole, fluotrimazole, fluopicolide, Fluopimomide, fluopyram, fluoroimide, furcarbanil, fluxapyroxad, fluquinconazole, furconazole, furconazole-cis, fludioxonil, flusilazole, flusulfamide, flutianil, flutolanil, flutriafol, flufenoxadiazam, flufenoxystrobin, furfural, flubeneteram, furmecyclox, flumetylsulforim, flumetover, flumorph, proquinazid, prochloraz, procymidone, prothiocarb, prothioconazole, pronitridine, propamocarb, propiconazole, propineb, furophanate, probenazole, bromuconazole, florylpicoxamid, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, benzovindiflupyr, bentaluron, benthiazole, benthiavalicarb, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, mandestrobin, myclozolin, myclobutanil, mildiomycin, milneb, mecarbinzid, methasulfocarb, metazoxolon, metam, metam-sodium, metalaxyl, metalaxyl-M, metarylpicoxamid, metiram, methyl isothiocyanate, meptyldinocap, metyltetraprole, metconazole, metsulfovax, methfuroxam, metominostrobin, metrafenone, mepanipyrim, mefenoxam, mefentrifluconazole, meptyldinocap, mepronil, mebenil, iodomethane, rabenzazole, methyl bromide, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, iofensulfuron, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epyrifenacil, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, clacyfos, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, chloranocryl, chloramben, cloransulam, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorphthalim, chlorflurazole, chlorflurenol, chlorprocarb, chlorpropham, chlormequat, chloreturon, chloroxynil, chloroxuron, chlorotoluron, chloropon, saflufenacil, cyanazine, cyanatryn, di-allate, diuron, diethamquat, dioxopyritrione, dicamba, cycluron, cycloate, cycloxydim, diclosulam, cyclosulfamuron, cyclopyranil, cyclopyrimorate, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, cypyrafluone, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimesulfazet, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, tiafenacil, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetflupyrolimet, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, triafamone, tri-allate, trietazine, tricamba, triclopyr, tridiphane, tritac, tritosulfuron, tripyrasulfone, trifludimoxazin, triflusulfuron, triflusulfuron-methyl, trifluralin, trifloxysulfuron, tripropindan, tribenuron, tribenuron-methyl, trifop, trifopsime, trimeturon, tolpyralate, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, halauxifen, haloxyfop, haloxyfop-P, haloxyfop-methyl, halosafen, halosulfuron, halosulfuron-methyl, bilanafos, bixlozone, picloram, picolinafen, bicyclopyrone, bispyribac, bispyribac-sodium, pydanon, pinoxaden, bipyrazone, bifenox, piperophos, hymexazol, pyraclonil, pyrasulfotole, pyrazoxyfen, pyrazosulfuron, pyrazosulfuron-ethyl, pyrazolate, bilanafos, pyraflufen, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenquinotrione, fenthiaprop, fenteracol, fentrazamide, fenpyrazone, phenmedipham, phenmedipham-ethyl, butachlor, butafenacil, butamifos, buthiuron, buthidazole, butylate, buturon, butenachlor, butroxydim, butralin, butroxydim, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, florpyrauxifen, hexachloroacetone, hexazinone, pethoxamid, benazolin, penoxsulam, pebulate, beflubutamid, beflubutamid-M, vernolate, perfluidone, bencarbazone, benquitrione, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, lancotrione, linuron, rimisoxafen, rimsulfuron, lenacil, rhodethanil, calcium peroxide and methyl bromide.

Exemplary biopesticides used for the same purposes as above include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as Monacrosporium phymatophagum, Steinernema carpocapsae, Steinernema kushidai and Pasteuria *penetrans*; microbial pesticides used as a microbicide, such as *Trichoderma* lignorum, *Agrobacterium* radiobactor, avirulent *Erwinia carotovora* and *Bacillus subtilis*; and biopesticides used as a herbicide, such as *Xanthomonas campestris*. Such a combined use of the agricultural and horticultural insecticidal and acaricidal agent of the present invention with the foregoing biopesticide as a mixture can be expected to provide the same effect as above.

Other examples of the biopesticides include natural predators such as Encarsia *formosa, Aphidius colemani*, Aphidoletes aphidimyza, Diglyphus isaea, Dacnusa *sibirica, Phytoseiulus persimilis, Amblyseius cucumeris* and Orius sauteri; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

EXAMPLES

Hereinafter, the representative examples are exemplified, but the present invention is not limited to these examples.

Production Example 1

Production of N-(4-fluorophenyl)-5-hydroxy-3-oxo-1-(4-trifluoromethylphenyl)-1,2,3,6-tetrahydropyridazine-4-carboxamide (Compound No. 1-7)

[Formula 14]

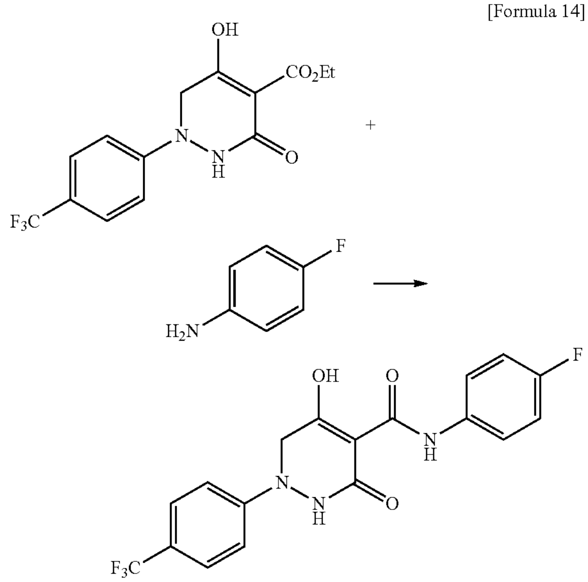

Ethyl 5-hydroxy-3-oxo-1-(4-trifluoromethylphenyl)-1,2,3,6-tetrahydropyridazine-4-carboxylate (0.15 g, 0.45 mmol) was mixed with toluene (5 ml). To the mixture, 4-fluoroaniline (0.06 g, 0.54 mmol) was added dropwise, and the mixture was stirred with a Dean-Stark apparatus under heating reflux while removing ethanol for 2 hours. The solution after the reaction was allowed to cool, and then concentrated under reduced pressure. The obtained crude reaction product was purified by silica gel column chromatography to give the title compound (0.05 g).

Yield: 28%

Physical property: melting point 65-70° C.

Production Example 2

Production of N-(4-fluorophenyl)-1-(6-chloropyridin-3-yl)-5-hydroxy-3-oxo-1,2,3,6-tetrahydropyridazine-4-carbothioamide (Compound No. 2-3)

[Formula 15]

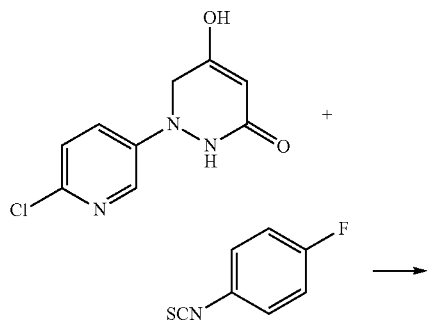

-continued

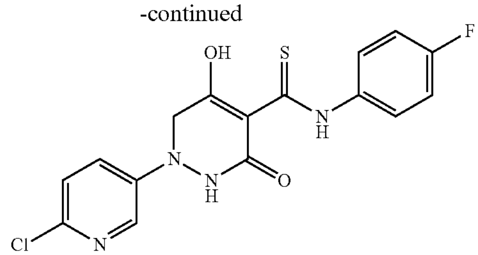

1-(6-Chloropyridin-3-yl)-5-hydroxy-1,6-dihydro-pyridazin-3(2H)-one (0.10 g, 0.44 mmol) was dissolved in dimethylformamide (3.0 mL). Cesium carbonate (0.17 g, 0.53 mmol) was added thereto, then 4-fluorophenyl isothiocyanate (0.11 g, 0.71 mmol) was slowly added dropwise, and the mixture was stirred at room temperature for 2 hours. To the solution after the reaction, 1 N hydrochloric acid (10 mL) was slowly added, and ethyl acetate (10 mL) was added to separate the mixture into solutions. The aqueous layer was extracted twice with ethyl acetate (10 mL), and the organic layers were combined and washed once with saturated saline (10 mL), and then dried over anhydrous sodium sulfate. The solution was concentrated under reduced pressure, and the obtained crude product was purified by silica gel column chromatography to give the title compound (0.02 g).

Yield: 12%

Physical property: melting point 230-233° C.

Production Example 3

Production of N-(4-fluorophenyl)-1-(6-trifluoromethylpyridin-3-yl)-5-hydroxy-3-thioxo-1,2,3,6-tetrahydropyridazine-4-carboxamide (Compound No. 2-5)

[Formula 16]

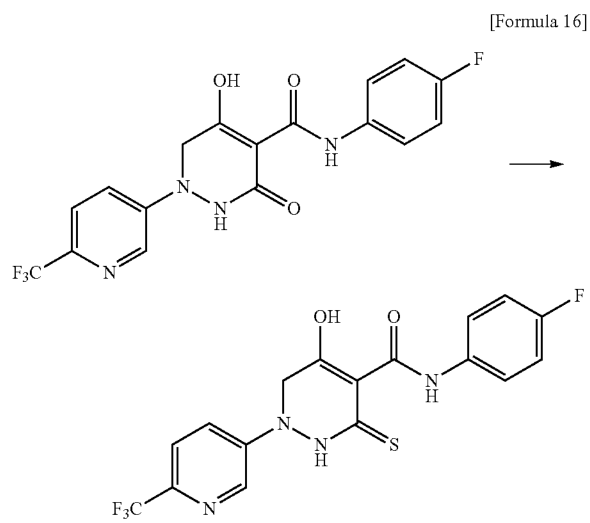

To a solution of N-(4-fluorophenyl)-5-hydroxy-3-oxo-1-(4-trifluoromethylpyridin-3-yl)-1,2,3,6-tetrahydropyridazine-4-carboxamide (0.10 g, 0.25 mmol) in toluene (10 mL), a Lawesson's reagent (0.056 g, 0.14 mmol) was added, and the mixture was stirred under heating reflux for 2 hours. After the reaction was completed, the reaction solution was concentrated with a rotary evaporator. The obtained residue was dissolved in ethyl acetate, and purified by silica gel chromatography. The obtained crystal was washed with normal hexane/methyl tertiary-butyl and filtered to give the title compound (0.055 g, 0.13 mmol).

Yield: 52%

Physical property: melting point: 182-184° C.

Reference Example 1

Production of 1-diphenylmethylene-2-(4-trifluoromethylphenyl) hydrazine

[Formula 17]

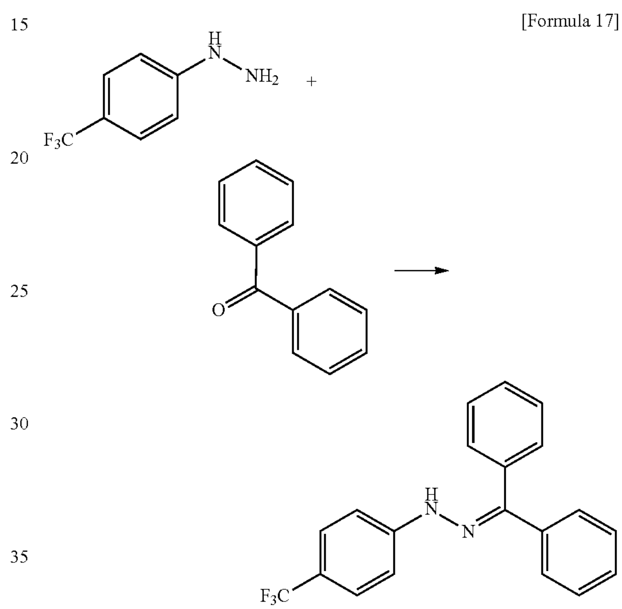

4-Trifluoromethylphenylhydrazine (5.28 g, 30.0 mmol) was dissolved in ethanol (50 mL), and benzophenone (5.28 g, 29 mmol) and acetic acid (5.40 g, 90 mmol) were added thereto, and the mixture was stirred under heating reflux for 2 hours. The solution after the reaction was allowed to cool, and then concentrated under reduced pressure. The obtained crude reaction product was purified by silica gel column chromatography to give the title compound (9.4 g).

Yield: 92%

Reference Example 2

Production of methyl 2-{2-diphenylmethylene-1-(4-trifluoromethylphenyl)hydrazinyl}acetate

[Formula 18]

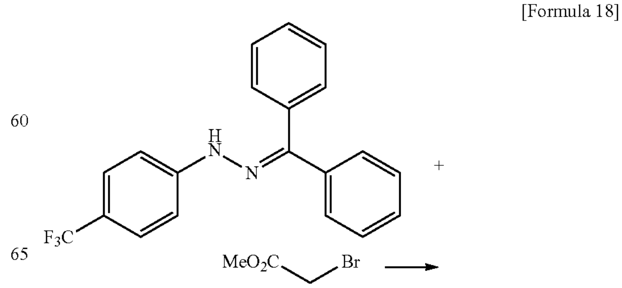

-continued

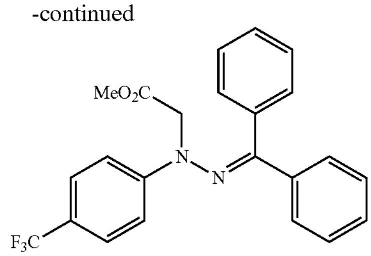

A solution of 60% sodium hydride (1.2 g, 30.0 mmol) was suspended in dimethylacetamide (20 mL), and a solution of 1-diphenylmethylene-2-(4-trifluoromethylphenyl)hydrazine (8.51 g, 25.0 mmol) in dimethylacetamide (10 mL) was slowly added dropwise under ice-cooling, and the mixture was stirred for 10 minutes. Methyl bromoacetate (4.97 g, 32.5 mmol) was slowly added dropwise thereto, and the mixture was warmed to room temperature and stirred for 2 hours. The solution after the reaction was slowly poured into ice water (30 mL), and the aqueous layer was extracted three times with ethyl acetate (30 mL). The obtained organic layers were combined and washed once with a saturated saline (30 mL), and dried over anhydrous sodium sulfate. The solution was concentrated under reduced pressure, and the obtained crude reaction product was purified by silica gel column chromatography to give the title compound (7.0 g).

Yield: 68%

Reference Example 3

Production of methyl 2-{1-(4-trifluoromethylphenyl)hydrazinyl}acetate

[Formula 19]

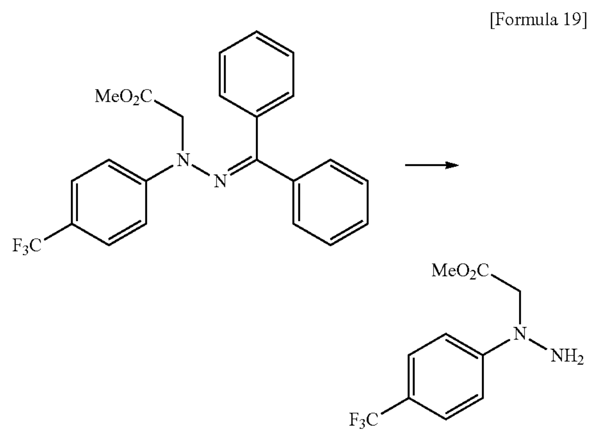

Methyl 2-{2-diphenylmethylene-1-(4-trifluoromethylphenyl)hydrazinyl}acetate (6.58 g, 15.7 mmol) was dissolved in a mixed solution of ethanol (50 mL) and 2-methyltetrahydrofuran (10 mL), and concentrated hydrochloric acid (10 mL) was added dropwise thereto, and the mixture was stirred at room temperature for 3 hours. The solution after the reaction was concentrated under reduced pressure, then water (50 mL) was added, and potassium carbonate was added to make the mixture weakly basic. The aqueous layer was extracted three times with ethyl acetate (50 mL), and the obtained organic layers were combined and washed once with saturated saline (50 mL), and then dried over anhydrous sodium sulfate. The solution was concentrated under reduced pressure, and the obtained crude reaction product was purified by silica gel column chromatography to give the title compound (3.65 g).

Yield: 94%

Reference Example 4

Production of ethyl 3-{2-(2-methoxy-2-oxoethyl)-2-(4-trifluoromethylphenyl)hydrazinyl}-3-oxopropionate

[Formula 20]

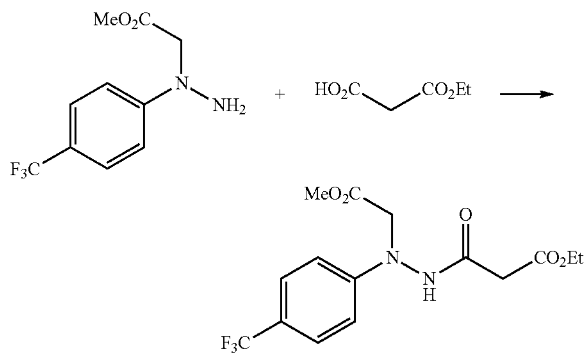

Methyl 2-{1-(4-trifluoromethylphenyl)hydrazinyl}acetate (3.65 g, 14.7 mmol) was mixed with chloroform (20 mL), and monoethyl malonate (3.88 g, 29.4 mmol), 1-ethyl-3-(3-dimethylaminopropyl)carbodiimide hydrochloride (5.64 g, 29.4 mmol), and 4-dimethylaminopyridine (3.59 g, 29.4 mmol) were sequentially added, and the mixture was stirred at room temperature for 2 hours. To the solution after the reaction, water (50 mL) and chloroform (50 mL) were added to separate the mixture into solutions. The obtained organic layer was washed once with 10% hydrochloric acid (50 mL), and washed once with saturated saline (50 mL), and then dried over anhydrous sodium sulfate. The solution was concentrated under reduced pressure, and the obtained crude reaction product was purified by silica gel column chromatography to give the title compound (3.9 g).

Yield: 73%

Reference Example 5

Production of ethyl 5-hydroxy-3-oxo-1-(4-trifluoromethylphenyl)-1,2,3,6-tetrahydropyridazine-4-carboxylate (Compound No. 5-29)

[Formula 21]

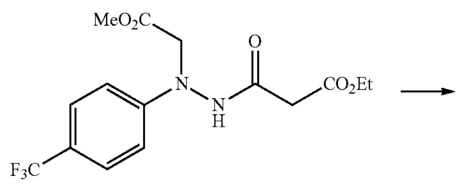

-continued

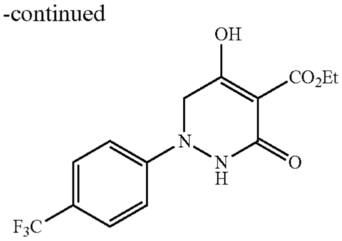

Ethyl 3-{2-(2-methoxy-2-oxoethyl)-2-(4-trifluoromethylphenyl)hydrazinyl}-3-oxopropionate (1.1 g, 3.0 mmol) was dissolved in super-dehydrated ethanol (10 mL) under the argon atmosphere, and a solution of 20% sodium ethoxide in ethanol (2.04 g, 6.0 mmol) was slowly added dropwise thereto, and the mixture was stirred at 60° C. for 1 hour. The solution after the reaction was allowed to cool, and then concentrated under reduced pressure. To the obtained crude reaction product, water (30 mL) and ethyl acetate (20 mL) were added to separate the mixture into solutions. To the aqueous layer, 10% hydrochloric acid was added to make it acidic. The aqueous layer was extracted three times with ethyl acetate (30 mL), and the organic layers were combined and washed once with saturated saline (30 mL), and then dried over anhydrous sodium sulfate. The solution was concentrated under reduced pressure, then the precipitated crystal was washed with a mixed solution of normal hexane and ethyl acetate to give the title compound (0.35 g).

Yield: 35%

Reference Example 6

Production of 5-hydrazinyl-2-trifluoromethylpyridine

[Formula 22]

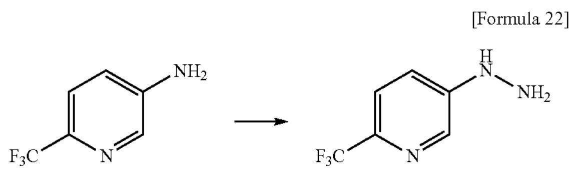 [SMILES: Nc1ccc(C(F)(F)F)nc1 ; NNc1ccc(C(F)(F)F)nc1]

5-Amino-2-trifluoromethylpyridine (9.73 g, 60.0 mmol) was dissolved in concentrated hydrochloric acid (80 mL). An aqueous solution of sodium nitrite (4.55 g, 66.0 mmol) dissolved in water (20 mL) was slowly added dropwise thereto under ice-cooling for 30 minutes while adjusting the temperature of the reaction solution not to exceed 10° C. After the dropwise addition was completed, the mixture was stirred at the same temperature for 30 minutes. In a separately prepared reaction vessel, tin(II) chloride (22.75 g, 120.0 mmol) was dissolved in concentrated hydrochloric acid (20 mL). The solution of the diazonium salt prepared as above was slowly added dropwise thereto under ice-cooling for 30 minutes while adjusting the temperature of the reaction solution not to exceed 10° C. After the dropwise addition was completed, the mixture was warmed to room temperature and stirred for 2 hours. To the solution after the reaction, an aqueous sodium hydroxide solution was added under ice-cooling to make it basic, and then celite filtration was carried out. To the obtained filtrate, ethyl acetate (200 mL) was added to separate the mixture into solutions. The aqueous layer was extracted twice with ethyl acetate (100 mL), and the organic layers were combined and washed once with saturated saline (100 mL), and then dried over anhydrous sodium sulfate. The solution was concentrated under reduced pressure, and the obtained crude reaction product was purified by silica gel column chromatography to give the title compound (7.0 g).

Yield: 66%

Reference Example 7

Production of 2-hydrazinyl-5-trifluoromethylpyridine

[Formula 23]

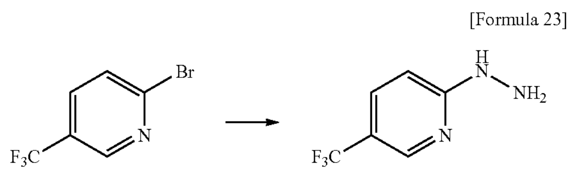 [SMILES: FC(F)(F)c1ccc(Br)nc1 ; NNc1ccc(C(F)(F)F)cn1]

2-Bromo-5-trifluoromethylpyridine (4.52 g, 20.0 mmol) was dissolved in ethanol (30 mL), and hydrazine monohydrate (8.0 g, 160.0 mmol) was slowly added dropwise thereto, and the mixture was stirred under heating reflux for 3 hours. The solution after the reaction was allowed to cool, and then water (10 mL) was added, and the mixture was concentrated under reduced pressure. To the obtained concentrate, water (20 mL) and ethyl acetate (30 mL) were added to separate the mixture into solutions. The aqueous layer was extracted twice with ethyl acetate (30 mL), and the organic layers were combined and washed once with saturated saline (30 mL), and then dried over anhydrous sodium sulfate. The solution was concentrated under reduced pressure, and the obtained crude reaction product was purified by silica gel column chromatography to give the title compound (3.50 g).

Yield: 99%

Reference Example 8

Production of 1-(6-chloropyridin-3-yl)-5-hydroxy-1,6-dihydropyridazin-3(2H)-one (Compound No. 4-28)

[Formula 24]

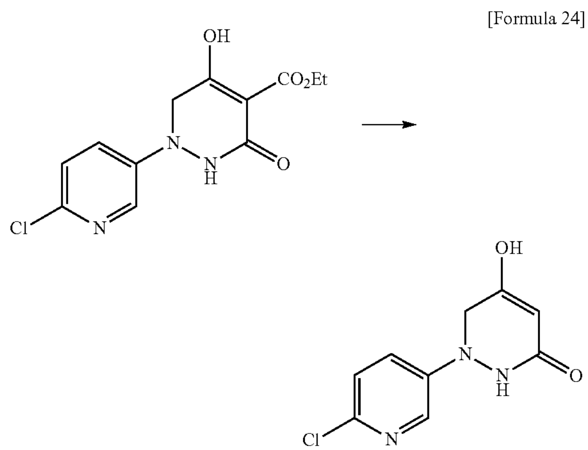

Ethyl 1-(6-chloropyridin-3-yl)-5-hydroxy-3-oxo-1,2,3,6-tetrahydropyridazine-4-carboxylate (1.0 g, 3.4 mmol) was suspended in a mixed solution of acetonitrile (10 mL) and water (1 mL), and the mixture was stirred under heating reflux for 2 hours. The solution after the reaction was allowed to cool, and then concentrated under reduced pressure. The obtained crude reaction product was purified by silica gel column chromatography to give the title compound (0.58 g).

Yield: 76%

Hereinafter, formulation examples are shown, but the present invention is not limited thereto. In the formulation examples, "part" means part by weight.

Formulation Example 1

Compound of the present invention 10 parts
Xylene 70 parts
N-methylpyrrolidone 10 parts
Mixture of polyoxyethylene nonylphenyl ether and calcium alkylbenzene sulfonate 10 parts The above ingredients are uniformly mixed for dissolution to give an emulsifiable concentrate formulation.

Formulation Example 2

Compound of the present invention 3 parts
Clay powder 82 parts
Diatomite powder 15 parts The above ingredients are uniformly mixed and then pulverized to give a dust formulation.

Formulation Example 3

Compound of the present invention 5 parts
Mixture of bentonite powder and clay powder 90 parts
Calcium lignosulfonate 5 parts The above ingredients are uniformly mixed. After addition of an appropriate volume of water, the mixture is kneaded, granulated and dried to give a granular formulation.

Formulation Example 4

Compound of the present invention 20 parts
Kaolin and synthetic high-dispersion silicic acid 75 parts
Mixture of polyoxyethylene nonylphenyl ether and calcium alkylbenzene sulfonate 5 parts The above ingredients are uniformly mixed and then pulverized to give a wettable powder formulation.

Hereinafter, biological test examples are shown, but the present invention is not limited thereto.

Test Example 1

Insecticidal Test on Diamondback moth (*Plutella xylostella*)

Adults of diamondback moth were released onto Chinese cabbage seedlings and allowed to lay eggs thereon. At 2 days after the release of the adults, the Chinese cabbage seedlings with laid eggs were dipped for about 30 seconds in agrochemical dispersions diluted to 500 ppm, each of which contained a different compound represented by the general formula (1) of the present invention as an active ingredient. After air-dried, the seedlings were kept in a thermostatic chamber at 25° C. At 6 days after the dip treatment, the number of hatched larvae per plot was counted, the mortality rate was calculated according to the formula shown below, and the insecticidal efficacy was evaluated according to the criteria shown below. This test was conducted in triplicate using 10 adults of diamondback moth per plot.

$$\text{Corrected mortality rate (\%)} = (\text{Number of hatched larvae in a non-treatment plot} - \text{Number of hatched larvae in a treatment plot}) / (\text{Number of hatched larvae in a non-treatment plot}) \times 100 \quad \text{[Expression 1]}$$

Criteria:

A: the mortality rate is 100%.

B: the mortality rate is 90 to 99%.

C: the mortality rate is 80 to 89%.

D: the mortality rate is 50 to 79%.

E: the mortality rate is 0 to 49%.

As a result, among the compounds represented by the general formula (1) of the present invention, compounds Nos. 1-4, 1-7, 1-9, 1-11, 1-14, 1-16, 1-18, 1-21, 1-23, 1-26, 1-27, 1-28, 1-29, 1-30, 1-33, 1-35, 1-36, 1-37, 1-38, 1-39, 1-40, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-62, 1-63, 1-67, 1-68, 1-69, 1-70, 1-73, 1-121, 1-122, 1-123, 1-124, 1-127, 1-128, 1-129, 1-130, 1-131, 1-132, 1-133, 1-134, 1-137, 1-138, 1-139, 1-140, 1-143, 1-144, 1-146, 1-147, 1-148, 1-149, 1-151, 1-152, 1-153, 1-154, 1-157, 1-158, 1-159, 1-160, 1-162, 1-163, 1-164, 1-167, 1-168, 1-170, 1-172, 1-173, 1-175, 1-176, 1-179, 1-182, 1-183, 1-184, 1-186,1-187, 1-188, 1-189, 1-191, 1-192, 1-193, 1-194, 1-195, 1-196, 1-197, 1-198, 1-199, 1-202, 1-203, 1-204, 1-205, 1-206, 1-212, 1-215, 1-216, 1-218, 1-221, 1-222, 1-227, 1-229, 1-230, 1-233, 1-235, 1-236, 1-237, 1-238, 1-239, 1-240, 1-241, 1-242, 1-243, 1-244, 1-245, 1-246, 1-247, 1-248, 1-249, 1-250, 1-256, 1-257, 1-258, 1-260, 1-261, 1-263, 1-264, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-310, 1-311, 1-312, 1-314, 1-315, 1-316, 1-317, 1-318, 2-3, 2-4, 2-5, 2-6, 2-7, 2-8, 2-9, 2-10, 2-11, 2-12, 2-14, 2-16, 2-18, 2-19, 2-20 and 3-2 exhibited excellent activity of criteria A against diamondback moth.

Test Example 2

Insecticidal Test on Small Brown Planthopper (*Laodelphax striatella*)

The compounds represented by the general formula (1) of the present invention or salts thereof were separately dispersed in water and diluted to 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of small brown planthopper, and then the glass test tubes were capped with cotton plugs. At 8 days after the inoculation, the numbers of surviving larvae and dead larvae were counted, the corrected mortality rate was calculated according to the formula shown below, and the insecticidal efficacy was evaluated according to the criteria of Test Example 1.

$$\text{Corrected mortality rate (\%)} = (\text{Survival rate in a non-treatment plot} - \text{Survival rate in a treatment plot}) / (\text{Survival rate in a non-treatment plot}) \times 100 \quad \text{[Expression 2]}$$

As a result, among the compounds represented by the general formula (1) of the present invention, compounds Nos. 1-4, 1-7, 1-9, 1-18, 1-11, 1-14, 1-21, 1-23, 1-26, 1-27, 1-28, 1-29, 1-30, 1-33, 1-35, 1-36, 1-37, 1-38, 1-39, 1-40, 1-42, 1-43, 1-44, 1-45, 1-46, 1-47, 1-48, 1-49, 1-50, 1-51, 1-52, 1-53, 1-54, 1-56, 1-57, 1-58, 1-62, 1-63, 1-66, 1-67, 1-68, 1-69, 1-70, 1-73, 1-89, 1-121, 1-122, 1-123, 1-124, 1-127, 1-128, 1-129, 1-130, 1-132, 1-133, 1-134, 1-137, 1-138, 1-139, 1-140, 1-143, 1-144, 1-145, 1-146, 1-147, 1-148, 1-151, 1-152, 1-153, 1-154, 1-155, 1-157, 1-158, 1-162, 1-163, 1-164, 1-167, 1-168, 1-170, 1-172, 1-173, 1-174, 1-175, 1-176, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-209, 1-211, 1-212, 1-213, 1-214, 1-215, 1-216, 1-217, 1-218, 1-220, 1-221, 1-222, 1-224, 1-225, 1-230, 1-232, 1-236, 1-237, 1-238, 1-239, 1-241, 1-242, 1-244, 1-245, 1-246, 1-247, 1-248, 1-249, 1-250, 1-251, 1-252, 1-254, 1-255, 1-256, 1-257, 1-258, 1-259, 1-260, 1-261, 1-263, 1-264, 1-265, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-308, 1-310, 1-311, 1-312, 1-313, 1-314, 1-315, 1-316, 1-317, 1-318, 2-3, 2-4, 2-5, 2-6, 2-7, 2-8, 2-9, 2-10, 2-11, 2-12, 2-14, 2-15, 2-16, 2-17, 2-18, 2-19, 2-20, 3-1 and 3-2 exhibited excellent activity of criteria A against small brown planthopper.

Test Example 3

Insecticidal Test on Western flower *thrips* (*Frankliniella occidentalis*) Female adults of western flower *thrips* were inoculated onto kidney bean leaf pieces fixed on agar medium, and allowed to lay eggs thereon for one day, then the female adults were removed. After 3 days, the hatched larvae on the leaf pieces were counted, and then the agrochemical dispersions diluted to 500 ppm, each of which contained the compound described in Tables 1 to 5 as an active ingredient were applied. The number of larvae of the species surviving at 4 days after the treatment was counted, and the mortality rate was calculated according to the formula shown below, and the insecticidal efficacy was evaluated according to the criteria of Test Example 1. This test was conducted in duplicate.

$$\text{Corrected mortality rate (\%)} = (\text{Survival rate in a non-treatment plot} - \text{Survival rate in a treatment plot}) / (\text{Survival rate in a non-treatment plot}) \times 100 \quad \text{[Expression 3]}$$

As a result, among the compounds represented by the general formula (1) of the present invention, compounds Nos. 1-4, 1-7, 1-9, 1-14, 1-18, 1-21, 1-23, 1-26, 1-27, 1-28, 1-29, 1-30, 1-33, 1-35, 1-37, 1-38, 1-39, 1-40, 1-42, 1-43, 1-44, 1-45, 1-46, 1-47, 1-48, 1-49, 1-50, 1-51, 1-52, 1-53, 1-54, 1-55, 1-57, 1-58, 1-59, 1-62, 1-63, 1-67, 1-68, 1-69, 1-70, 1-73, 1-89, 1-121, 1-122, 1-123, 1-124, 1-127, 1-128, 1-129, 1-130, 1-131, 1-132, 1-133, 1-134, 1-137, 1-138, 1-139, 1-140, 1-143, 1-144, 1-145, 1-146, 1-147, 1-148, 1-149, 1-150, 1-151, 1-152, 1-153, 1-154, 1-155, 1-157, 1-158, 1-159, 1-160, 1-167, 1-168, 1-170, 1-172, 1-173, 1-175, 1-176, 1-183, 1-184, 1-185, 1-186, 1-187, 1-188, 1-189, 1-191, 1-192, 1-193, 1-194, 1-195, 1-196, 1-197, 1-198, 1-199, 1-200, 1-203, 1-204, 1-205, 1-206, 1-207, 1-212, 1-214, 1-215, 1-216, 1-218, 1-221, 1-222, 1-227, 1-229, 1-230, 1-233, 1-235, 1-236, 1-237, 1-238, 1-239, 1-240, 1-241, 1-243, 1-244, 1-245, 1-246, 1-247, 1-248, 1-249, 1-250, 1-251, 1-254, 1-256, 1-257, 1-258, 1-259, 1-260, 1-263, 1-264, 1-275, 1-276, 1-277, 1-278, 1-279, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-310, 1-311, 1-312, 1-314, 1-315, 1-316, 2-3, 2-4, 2-5, 2-6, 2-7, 2-8, 2-9, 2-10, 2-11, 2-12, 2-16, 2-18, 2-19, 2-20 and 3-2 exhibited excellent activity of criteria A against western flower *thrips*.

INDUSTRIAL APPLICABILITY

The compounds or salts thereof of the present invention have an excellent effect as agricultural and horticultural insecticidal agents.

The invention claimed is:

1. A compound represented by general formula (1):

(1)

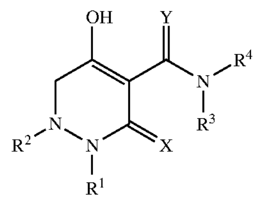

wherein, $R^1$ represents (a1) a hydrogen atom;

(a2) a $(C_1\text{-}C_6)$alkyl group;

(a3) a $(C_2\text{-}C_6)$alkenyl group;

(a4) a $(C_2\text{-}C_6)$alkynyl group;

(a5) a $(C_3\text{-}C_6)$cycloalkyl group;

(a6) a $(C_1\text{-}C_6)$alkoxy group;

(a7) a halo$(C_1\text{-}C_6)$alkyl group;

(a8) a $(C_1\text{-}C_6)$alkylcarbonyl group;

(a9) a $(C_1\text{-}C_6)$alkoxycarbonyl group;

(a10) a substituted $(C_1\text{-}C_6)$alkyl group having on the chain one to three substituents each independently selected from the group consisting of a cyano group, a $(C_1\text{-}C_6)$alkoxy group, and a $(C_3\text{-}C_6)$cycloalkyl group;

(a11) a thiazolylmethyl group;

(a12) a substituted thiazolylmethyl group having on the ring one to two substituents each independently selected from the group consisting of a halogen atom, a $(C_1\text{-}C_6)$alkyl group, and a $(C_1\text{-}C_6)$alkoxy group;

(a13) a benzyl group; or (a14) a substituted benzyl group having on the ring one to three substituents each independently selected from the group consisting of a halogen atom, a $(C_1\text{-}C_6)$alkyl group, and a $(C_1\text{-}C_6)$alkoxy group, $R^2$ represents (b1) an aryl group;

(b2) a substituted aryl group having on the ring one or more substituents each independently selected from substituent group A;

(b3) a 5- to 10-membered ring heterocyclic group; or (b4) a substituted 5- to 10-membered ring heterocyclic group having on the ring one or more substituents each independently selected from the substituent group A, provided that $R^2$ does not have a substitution with a $(C_1-C_6)$alkylsulfonyl group, a halo$(C_1-C_6)$alkylsulfonyl group, an N—$(C_1-C_6)$alkylaminosulfonyl group, an N,N-di$(C_1-C_6)$alkylaminosulfonyl group, and an $R^6$—$(R^7$—N=)O=S group (wherein $R^6$ represents a $(C_1-C_6)$alkyl group, a $(C_3-C_6)$cycloalkyl group, a halo$(C_1-C_6)$alkyl group, or a $(C_1-C_6)$alkoxy$(C_1-C_6)$alkyl group, and $R^7$ represents a hydrogen atom, a cyano group, a $(C_1-C_6)$alkyl group, a $(C_3-C_6)$cycloalkyl group, a halo$(C_1-C_6)$alkyl group, a $(C_2-C_6)$alkylcarbonyl group, or a halo$(C_2-C_6)$alkylcarbonyl group) at an adjacent atom to an atom attached to the tetrahydropyridazine ring, $R^3$ represents (c1) a hydrogen atom;

(c2) a $(C_1-C_6)$alkyl group;

(c3) a $(C_3-C_6)$cycloalkyl group;

(c4) a $(C_1-C_6)$alkoxy group; or (c5) a $(C_1-C_6)$alkylcarbonyl group, $R^4$ represents (d1) a $(C_1-C_6)$alkyl group;

(d2) a $(C_2-C_6)$alkenyl group;

(d3) a $(C_2-C_6)$alkynyl group;

(d4) a $(C_3-C_6)$cycloalkyl group;

(d5) a halo$(C_1-C_6)$alkyl group;

(d6) a halo$(C_2-C_6)$alkenyl group;

(d7) a halo$(C_2-C_6)$alkynyl group;

(d8) a substituted $(C_1-C_6)$alkyl group having one to three substituents each independently selected from substituent group B;

(d9) a substituted $(C_3-C_6)$cycloalkyl group having on the ring one to three substituents each independently selected from substituent group C;

(d10) a $(C_1-C_6)$alkylsulfonyl group;

(d11) an N—$(C_1-C_6)$alkylsulfamoyl group;

(d12) a phenyl group;

(d13) a substituted phenyl group having on the ring one to five substituents each independently selected from substituent group D;

(d14) a phenyl$(C_1-C_6)$alkyl group;

(d15) a substituted phenyl$(C_1-C_6)$alkyl group having on the ring one to five substituents each independently selected from the substituent group D;

(d16) a pyridyl group;

(d17) a substituted pyridyl group having on the ring one to four substituents each independently selected from the substituent group D;

(d18) a pyridazinyl group;

(d19) a substituted pyridazinyl group having on the ring one to three substituents each independently selected from the substituent group D;

(d20) a pyrimidinyl group;

(d21) a substituted pyrimidinyl group having on the ring one to three substituents each independently selected from the substituent group D;

(d22) a pyrazinyl group;

(d23) a substituted pyrazinyl group having on the ring one to three substituents each independently selected from the substituent group D;

(d24) a pyrazolyl group;

(d25) a substituted pyrazolyl group having on the ring one to three substituents each independently selected from the substituent group D;

(d26) an isoxazolyl group;

(d27) a substituted isoxazolyl group having on the ring one to two substituents each independently selected from the substituent group D;

(d28) an isothiazolyl group;

(d29) a substituted isothiazolyl group having on the ring one to two substituents each independently selected from the substituent group D;

(d30) an oxazolyl group;

(d31) a substituted oxazolyl group having on the ring one to two substituents each independently selected from the substituent group D;

(d32) a thiazolyl group;

(d33) a substituted thiazolyl group having on the ring one to two substituents each independently selected from the substituent group D;

(d34) a triazolyl group;

(d35) a substituted triazolyl group having on the ring one to two substituents each independently selected from the substituent group D;

(d36) a thiadiazolyl group;

(d37) a substituted thiadiazolyl group having on the ring one substituent each independently selected from the substituent group D;

(d38) a tetrazolyl group;

(d39) a substituted tetrazolyl group having on the ring one substituent each independently selected from the substituent group D;

(d40) a triazinyl group;

(d41) a substituted triazinyl group having on the ring one to two substituents each independently selected from the substituent group D;

(d42) a furyl$(C_1-C_6)$alkyl group;

(d43) a substituted furyl$(C_1-C_6)$alkyl group having on the ring one to three substituents each independently selected from the substituent group D;

(d44) a thienyl$(C_1-C_6)$alkyl group;

(d45) a substituted thienyl$(C_1-C_6)$alkyl group having on the ring one to three substituents each independently selected from the substituent group D;

(d46) a quinolinyl group;

(d47) a substituted quinolinyl group having on the ring one to six substituents each independently selected from the substituent group D;

(d48) a benzothiazolyl group;

(d49) a substituted benzothiazolyl group having on the ring one to four substituents each independently selected from the substituent group D;

(d50) a pyridyl$(C_1-C_6)$alkyl group;

(d51) a substituted pyridyl$(C_1-C_6)$alkyl group having on the ring one to four substituents each independently selected from the substituent group D;

(d52) a pyrazinyl$(C_1-C_6)$alkyl group;

(d53) a substituted pyrazinyl$(C_1-C_6)$alkyl group having on the ring one to three substituents each independently selected from the substituent group D;

(d54) a naphthyl group;

(d55) a substituted naphthyl group having on the ring one to seven substituents each independently selected from the substituent group D;

(d56) a tetrahydronaphthyl group; or (d57) a substituted tetrahydronaphthyl group having on the ring one to ten substituents each independently selected from the substituent group D, X and Y each independently represent an oxygen atom or a sulfur atom, the substituent group A consists of (e1) a halogen atom;

(e2) a cyano group;

(e3) a nitro group;

(e4) a hydroxyl group;

(e5) a carboxyl group;

(e6) a $(C_1-C_6)$alkyl group;

(e7) a $(C_2-C_6)$alkenyl group;

(e8) a $(C_2-C_6)$alkynyl group;

(e9) a $(C_1-C_6)$alkoxy group;

(e10) a $(C_3-C_6)$cycloalkyl group;

(e11) a $(C_1-C_6)$alkylthio group;

(e12) a $(C_1-C_6)$alkylsulfinyl group;

(e13) a $(C_1-C_6)$alkylsulfonyl group;

(e14) a halo$(C_1-C_6)$alkyl group;

(e15) a halo$(C_2-C_6)$alkenyl group;

(e16) a halo$(C_2-C_6)$alkynyl group;

(e17) a halo$(C_1-C_6)$alkoxy group;

(e18) a halo$(C_3-C_6)$cycloalkyl group;

(e19) a halo$(C_1-C_6)$alkylthio group;

(e20) a halo$(C_1-C_6)$alkylsulfinyl group;

(e21) a halo$(C_1-C_6)$alkylsulfonyl group;

(e22) a $(C_1-C_6)$alkylcarbonylamino group;

(e23) a halo$(C_1-C_6)$alkylcarbonylamino group;

(e24) a $(C_1-C_6)$alkylsulfonylamino group;

(e25) a halo$(C_1-C_6)$alkylsulfonylamino group;

(e26) an $SF_5$ group;

(e27) a $(C_1-C_6)$alkoxy$(C_1-C_6)$alkyl group;

(e28) an N—$(C_1-C_6)$alkylcarboxamide group;

(e29) an N-halo$(C_1-C_6)$alkylcarboxamide group;

(e30) an oxadiazolyl group;

(e31) a substituted oxadiazolyl group having on the ring one substituent each independently selected from the group consisting of a halogen atom, a cyano group, a $(C_1-C_6)$alkyl group, a $(C_1-C_6)$alkoxy group, a $(C_3-C_6)$cycloalkyl group, a $(C_1-C_6)$alkylthio group, a $(C_1-C_6)$alkylsulfinyl group, a $(C_1-C_6)$alkylsulfonyl group, a halo$(C_1-C_6)$alkyl group, and a halo$(C_1-C_6)$alkoxy group;

(e32) a $(C_1-C_6)$alkoxycarbonyl group;

(e33) a methylenedioxy group formed by two adjacent substituents, wherein the methylenedioxy group is optionally substituted with one to two substituents selected from the group consisting of a halogen atom, a phenyl group, and a $(C_1-C_6)$alkyl group;

(e34) an N—$(C_1-C_6)$alkylaminosulfonyl group;

(e35) an N,N-di$(C_1-C_6)$alkylaminosulfonyl group;

(e36) an $R^6$—$(R^7$—N=)O=S group, wherein $R^6$ represents a $(C_1-C_6)$alkyl group, a $(C_3-C_6)$cycloalkyl group, a halo$(C_1-C_6)$alkyl group, or a $(C_1-C_6)$alkoxy$(C_1-C_6)$alkyl group, and $R^7$ represents a hydrogen atom, a cyano group, a $(C_1-C_6)$alkyl group, a $(C_3-C_6)$cycloalkyl group, a halo$(C_1-C_6)$alkyl group, a $(C_2-C_6)$alkylcarbonyl group, or a halo$(C_2-C_6)$alkylcarbonyl group; and (e37) a substituted $(C_3-C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group, the substituent group B consists of (f1) a cyano group;

(f2) a $(C_3-C_6)$cycloalkyl group;

(f3) a $(C_1-C_6)$alkoxy group;

(f4) a $(C_1-C_6)$alkylthio group;

(f5) a $(C_1-C_6)$alkylsulfinyl group;

(f6) a $(C_1-C_6)$alkylsulfonyl group;

(f7) a halo$(C_3-C_6)$cycloalkyl group;

(f8) a halo$(C_1-C_6)$alkoxy group;

(f9) a halo$(C_1-C_6)$alkylthio group;

(f10) a halo$(C_1-C_6)$alkylsulfinyl group;

(f11) a halo$(C_1-C_6)$alkylsulfonyl group;

(f12) a carboxamide group; and (f13) a phenylcarbonyl group, the substituent group C consists of (g1) a cyano group;

(g2) a $(C_1-C_6)$alkyl group;

(g3) a $(C_3-C_6)$cycloalkyl group;

(g4) a $(C_1-C_6)$alkoxy group;

(g5) a $(C_1-C_6)$alkylthio group;

(g6) a $(C_1-C_6)$alkylsulfinyl group;

(g7) a $(C_1-C_6)$alkylsulfonyl group;

(g8) a halo$(C_3-C_6)$cycloalkyl group;

(g9) a halo$(C_1-C_6)$alkoxy group;

(g10) a halo$(C_1-C_6)$alkylthio group;

(g11) a halo$(C_1-C_6)$alkylsulfinyl group;

(g12) a halo$(C_1-C_6)$alkylsulfonyl group;

(g13) a halo$(C_1-C_6)$alkyl group;

(g14) a carboxamide group;

(g15) a $(C_2-C_6)$alkynyl group; and (g16) a phenyl group, the substituent group D consists of (h1) a halogen atom;

(h2) a cyano group;

(h3) a hydroxyl group;

(h4) a carboxyl group;

(h5) a $(C_1-C_6)$alkyl group;

(h6) a $(C_1-C_6)$alkoxy group;

(h7) a $(C_3-C_6)$cycloalkyl group;

(h8) a $(C_1-C_6)$alkylthio group;

(h9) a $(C_1-C_6)$alkylsulfinyl group;

(h10) a $(C_1-C_6)$alkylsulfonyl group;

(h11) a halo$(C_1-C_6)$alkyl group;

(h12) a halo$(C_1-C_6)$alkoxy group;

(h13) a halo$(C_3-C_6)$cycloalkyl group;

(h14) a halo$(C_1-C_6)$alkylthio group;

(h15) a halo$(C_1-C_6)$alkylsulfinyl group;

(h16) a halo$(C_1-C_6)$alkylsulfonyl group;

(h17) a $(C_1-C_6)$alkoxycarbonyl group;

(h18) an N—$(C_1-C_6)$alkylcarboxamide group;

(h19) an N-halo$(C_1-C_6)$alkylcarboxamide group;

(h20) a methylenedioxy group formed by two adjacent substituents, wherein the methylenedioxy group is optionally substituted with one to two substituents selected from the group consisting of a halogen atom, a phenyl group, and a $(C_1-C_6)$alkyl group;

(h21) a nitro group;

(h22) an amino group; and (h23) a benzyloxycarbonyl group, or a salt thereof.

2. The compound or a salt thereof according to claim 1, wherein $R^1$, $R^3$, $R^4$, X, Y, and the substituent groups A, B, C, and D are as defined in claim 1, and $R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b15) a furyl group;

(b16) a substituted furyl group having on the ring one to three substituents each independently selected from the substituent group A;

(b17) a thienyl group;

(b18) a substituted thienyl group having on the ring one to three substituents each independently selected from the substituent group A;

(b19) an isoxazolyl group;

(b20) a substituted isoxazolyl group having on the ring one to two substituents each independently selected from the substituent group A;

(b21) an oxazolyl group;

(b22) a substituted oxazolyl group having on the ring one to two substituents each independently selected from the substituent group A;

(b23) a pyrazolyl group;

(b24) a substituted pyrazolyl group having on the ring one to three substituents each independently selected from the substituent group A;

(b25) an imidazolyl group;

(b26) a substituted imidazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b31) an isothiazolyl group;

(b32) a substituted isothiazolyl group having on the ring one to two substituents each independently selected from the substituent group A;

(b33) a thiadiazolyl group;

(b34) a substituted thiadiazolyl group having on the ring one substituent each independently selected from the substituent group A;

(b35) an imidazopyridyl group;

(b36) a substituted imidazopyridyl group having on the ring one to five substituents each independently selected from the substituent group A;

(b37) a quinoxalinyl group;

(b38) a substituted quinoxalinyl group having on the ring one to five substituents each independently selected from the substituent group A;

(b39) a benzoxazolyl group;

(b40) a substituted benzoxazolyl group having on the ring one to four substituents each independently selected from the substituent group A;

(b41) a benzimidazolyl group;

(b42) a substituted benzimidazolyl group having on the ring one to five substituents each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group;

(b48) a substituted quinolinyl group having on the ring one to six substituents each independently selected from the substituent group A;

(b49) a naphthyl group;

(b50) a substituted naphthyl group having on the ring one to seven substituents each independently selected from the substituent group A;

(b51) a triazinyl group;

(b52) a substituted triazinyl group having on the ring one to two substituents each independently selected from the substituent group A;

(b53) a pyrrolyl group;

(b54) a substituted pyrrolyl group having on the ring one to four substituents each independently selected from the substituent group A;

(b55) a tetrazolyl group;

(b56) a substituted tetrazolyl group having on the ring one substituent each independently selected from the substituent group A;

(b57) an oxadiazonyl group;

(b58) a substituted oxadiazonyl group having on the ring one substituent each independently selected from the substituent group A;

(b59) a 2-oxopyridyl group;

(b60) a substituted 2-oxopyridyl group having on the ring one to four substituents each independently selected from the substituent group A;

(b61) a benzofuranyl group;

(b62) a substituted benzofuranyl group having on the ring one to five substituents each independently selected from the substituent group A;

(b63) a benzisoxazolyl group;

(b64) a substituted benzisoxazolyl group having on the ring one to four substituents each independently selected from the substituent group A;

(b65) a benzothienyl group;

(b66) a substituted benzothienyl group having on the ring one to five substituents each independently selected from the substituent group A;

(b67) a benzisothiazolyl group;

(b68) a substituted benzisothiazolyl group having on the ring one to four substituents each independently selected from the substituent group A;

(b69) an indolyl group;

(b70) a substituted indolyl group having on the ring one to six substituents each independently selected from the substituent group A;

(b71) an isoindolyl group;
(b72) a substituted isoindolyl group having on the ring one to six substituents each independently selected from the substituent group A;
(b73) an indazolyl group;
(b74) a substituted indazolyl group having on the ring one to five substituents each independently selected from the substituent group A;
(b75) a benzotriazolyl group;
(b76) a substituted benzotriazolyl group having on the ring one to four substituents each independently selected from the substituent group A;
(b77) a furopyridyl group;
(b78) a substituted furopyridyl group having on the ring one to four substituents each independently selected from the substituent group A;
(b79) a thienopyridyl group;
(b80) a substituted thienopyridyl group having on the ring one to four substituents each independently selected from the substituent group A;
(b81) an indolizinyl group;
(b82) a substituted indolizinyl group having on the ring one to six substituents each independently selected from the substituent group A;
(b83) a pyrrolopyridyl group;
(b84) a substituted pyrrolopyridyl group having on the ring one to five substituents each independently selected from the substituent group A;
(b85) a pyrrolopyrimidinyl group;
(b86) a substituted pyrrolopyrimidinyl group having on the ring one to five substituents each independently selected from the substituent group A;
(b87) an oxazolopyridyl group;
(b88) a substituted oxazolopyridyl group having on the ring one to three substituents each independently selected from the substituent group A;
(b89) an isoxazolopyridyl group;
(b90) a substituted isoxazolopyridyl group having on the ring one to three substituents each independently selected from the substituent group A;
(b91) an isothiazolopyridyl group;
(b92) a substituted isothiazolopyridyl group having on the ring one to three substituents each independently selected from the substituent group A;
(b93) an imidazopyrimidinyl group;
(b94) a substituted imidazopyrimidinyl group having on the ring one to five substituents each independently selected from the substituent group A;
(b95) a pyrazolopyridyl group;
(b96) a substituted pyrazolopyridyl group having on the ring one to five substituents each independently selected from the substituent group A;
(b97) a pyrazolopyrimidinyl group;
(b98) a substituted pyrazolopyrimidinyl group having on the ring one to five substituents each independently selected from the substituent group A;
(b99) a triazolopyridyl group;
(b100) a substituted triazolopyridyl group having on the ring one to four substituents each independently selected from the substituent group A;
(b101) a triazolopyrimidinyl group;
(b102) a substituted triazolopyrimidinyl group having on the ring one to four substituents each independently selected from the substituent group A;
(b103) an isoquinolinyl group;
(b104) a substituted isoquinolinyl group having on the ring one to six substituents each independently selected from the substituent group A;
(b105) a cinnolinyl group;
(b106) a substituted cinnolinyl group having on the ring one to five substituents each independently selected from the substituent group A;
(b107) a phthalazinyl group;
(b108) a substituted phthalazinyl group having on the ring one to five substituents each independently selected from the substituent group A;
(b109) a quinazolinyl group;
(b110) a substituted quinazolinyl group having on the ring one to five substituents each independently selected from the substituent group A;
(b111) a naphthyridinyl group; or
(b112) a substituted naphthyridinyl group having on the ring one to five substituents each independently selected from the substituent group A.

3. The compound or a salt thereof according to claim 1, wherein $R^1$ represents
(a1) a hydrogen atom;
(a2) a $(C_1\text{-}C_6)$alkyl group; or
(a4) a $(C_2\text{-}C_6)$alkynyl group, $R^2$ represents
(b5) a phenyl group;
(b6) a substituted phenyl group having on the ring one to five substituents each independently selected from the substituent group A;
(b7) a pyridyl group;
(b8) a substituted pyridyl group having on the ring one to four substituents each independently selected from the substituent group A;
(b9) a pyridazinyl group;
(b10) a substituted pyridazinyl group having on the ring one to three substituents each independently selected from the substituent group A;
(b11) a pyrimidinyl group;
(b12) a substituted pyrimidinyl group having on the ring one to three substituents each independently selected from the substituent group A;
(b13) a pyrazinyl group;
(b14) a substituted pyrazinyl group having on the ring one to three substituents each independently selected from the substituent group A;
(b15) a furyl group;
(b16) a substituted furyl group having on the ring one to three substituents each independently selected from the substituent group A;
(b17) a thienyl group;
(b18) a substituted thienyl group having on the ring one to three substituents each independently selected from the substituent group A;
(b19) an isoxazolyl group;
(b20) a substituted isoxazolyl group having on the ring one to two substituents each independently selected from the substituent group A;
(b21) an oxazolyl group;
(b22) a substituted oxazolyl group having on the ring one to two substituents each independently selected from the substituent group A;
(b23) a pyrazolyl group;
(b24) a substituted pyrazolyl group having on the ring one to three substituents each independently selected from the substituent group A;
(b25) an imidazolyl group;

(b26) a substituted imidazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b31) an isothiazolyl group;

(b32) a substituted isothiazolyl group having on the ring one to two substituents each independently selected from the substituent group A;

(b33) a thiadiazolyl group;

(b34) a substituted thiadiazolyl group having on the ring one substituent each independently selected from the substituent group A;

(b35) an imidazopyridyl group;

(b36) a substituted imidazopyridyl group having on the ring one to five substituents each independently selected from the substituent group A;

(b37) a quinoxalinyl group;

(b38) a substituted quinoxalinyl group having on the ring one to five substituents each independently selected from the substituent group A;

(b39) a benzoxazolyl group;

(b40) a substituted benzoxazolyl group having on the ring one to four substituents each independently selected from the substituent group A;

(b41) a benzimidazolyl group;

(b42) a substituted benzimidazolyl group having on the ring one to five substituents each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group; or (b48) a substituted quinolinyl group having on the ring one to six substituents each independently selected from the substituent group A, $R^3$ represents (c1) a hydrogen atom; or (c2) a $(C_1\text{-}C_6)$alkyl group, $R^4$ represents (d1) a $(C_1\text{-}C_6)$alkyl group;

(d2) a $(C_2\text{-}C_6)$alkenyl group;

(d3) a $(C_2\text{-}C_6)$alkynyl group;

(d4) a $(C_3\text{-}C_6)$cycloalkyl group;

(d5) a halo$(C_1\text{-}C_6)$alkyl group;

(d8) a substituted $(C_1\text{-}C_6)$alkyl group having one to three substituents each independently selected from the substituent group B;

(d9) a substituted $(C_3\text{-}C_6)$cycloalkyl group having on the ring one to three substituents each independently selected from the substituent group C;

(d10) a $(C_1\text{-}C_6)$alkylsulfonyl group;

(d11) an N—$(C_1\text{-}C_6)$alkylsulfamoyl group;

(d12) a phenyl group;

(d13) a substituted phenyl group having on the ring one to five substituents each independently selected from the substituent group D;

(d14) a phenyl$(C_1\text{-}C_6)$alkyl group;

(d15) a substituted phenyl$(C_1\text{-}C_6)$alkyl group having on the ring one to five substituents each independently selected from the substituent group D;

(d16) a pyridyl group;

(d17) a substituted pyridyl group having on the ring one to four substituents each independently selected from the substituent group D;

(d18) a pyridazinyl group;

(d19) a substituted pyridazinyl group having on the ring one to three substituents each independently selected from the substituent group D;

(d20) a pyrimidinyl group;

(d21) a substituted pyrimidinyl group having on the ring one to three substituents each independently selected from the substituent group D;

(d22) a pyrazinyl group;

(d23) a substituted pyrazinyl group having on the ring one to three substituents each independently selected from the substituent group D;

(d24) a pyrazolyl group;

(d25) a substituted pyrazolyl group having on the ring one to three substituents each independently selected from the substituent group D;

(d26) an isoxazolyl group;

(d27) a substituted isoxazolyl group having on the ring one to two substituents each independently selected from the substituent group D;

(d28) an isothiazolyl group;

(d29) a substituted isothiazolyl group having on the ring one to two substituents each independently selected from the substituent group D;

(d30) an oxazolyl group;

(d31) a substituted oxazolyl group having on the ring one to two substituents each independently selected from the substituent group D;

(d32) a thiazolyl group;

(d33) a substituted thiazolyl group having on the ring one to two substituents each independently selected from the substituent group D;

(d34) a triazolyl group;

(d35) a substituted triazolyl group having on the ring one to two substituents each independently selected from the substituent group D;

(d36) a thiadiazolyl group;

(d37) a substituted thiadiazolyl group having on the ring one substituent each independently selected from the substituent group D;

(d38) a tetrazolyl group;

(d39) a substituted tetrazolyl group having on the ring one substituent each independently selected from the substituent group D;

(d40) a triazinyl group;

(d41) a substituted triazinyl group having on the ring one to two substituents each independently selected from the substituent group D;

(d42) a furyl$(C_1\text{-}C_6)$alkyl group;

(d43) a substituted furyl$(C_1\text{-}C_6)$alkyl group having on the ring one to three substituents each independently selected from the substituent group D;

(d44) a thienyl$(C_1\text{-}C_6)$alkyl group;

(d45) a substituted thienyl$(C_1\text{-}C_6)$alkyl group having on the ring one to three substituents each independently selected from the substituent group D;

(d46) a quinolinyl group;

(d47) a substituted quinolinyl group having on the ring one to six substituents each independently selected from the substituent group D;

(d48) a benzothiazolyl group;

(d49) a substituted benzothiazolyl group having on the ring one to four substituents each independently selected from the substituent group D;

(d50) a pyridyl($C_1$-$C_6$)alkyl group;

(d51) a substituted pyridyl($C_1$-$C_6$)alkyl group having on the ring one to four substituents each independently selected from the substituent group D;

(d52) a pyrazinyl($C_1$-$C_6$)alkyl group;

(d53) a substituted pyrazinyl($C_1$-$C_6$)alkyl group having on the ring one to three substituents each independently selected from the substituent group D;

(d54) a naphthyl group;

(d55) a substituted naphthyl group having on the ring one to seven substituents each independently selected from the substituent group D;

(d56) a tetrahydronaphthyl group; or (d57) a substituted tetrahydronaphthyl group having on the ring one to ten substituents each independently selected from the substituent group D, the substituent group A consists of (e1) a halogen atom;

(e2) a cyano group;

(e4) a hydroxyl group;

(e5) a carboxyl group;

(e6) a ($C_1$-$C_6$)alkyl group;

(e9) a ($C_1$-$C_6$)alkoxy group;

(e10) a ($C_3$-$C_6$)cycloalkyl group;

(e11) a ($C_1$-$C_6$)alkylthio group;

(e12) a ($C_1$-$C_6$)alkylsulfinyl group;

(e13) a ($C_1$-$C_6$)alkylsulfonyl group;

(e14) a halo($C_1$-$C_6$)alkyl group;

(e17) a halo($C_1$-$C_6$)alkoxy group;

(e18) a halo($C_3$-$C_6$)cycloalkyl group;

(e19) a halo($C_1$-$C_6$)alkylthio group;

(e20) a halo($C_1$-$C_6$)alkylsulfinyl group;

(e21) a halo($C_1$-$C_6$)alkylsulfonyl group;

(e22) a ($C_1$-$C_6$)alkylcarbonylamino group;

(e24) a ($C_1$-$C_6$)alkylsulfonylamino group;

(e28) an N—($C_1$-$C_6$)alkylcarboxamide group;

(e30) an oxadiazolyl group;

(e31) a substituted oxadiazolyl group having on the ring one substituent each independently selected from the group consisting of a halogen atom, a cyano group, a ($C_1$-$C_6$)alkyl group, a ($C_1$-$C_6$)alkoxy group, a ($C_3$-$C_6$) cycloalkyl group, a ($C_1$-$C_6$)alkylthio group, a ($C_1$-$C_6$) alkylsulfinyl group, a ($C_1$-$C_6$)alkylsulfonyl group, a halo($C_1$-$C_6$)alkyl group, and a halo($C_1$-$C_6$)alkoxy group;

(e32) a ($C_1$-$C_6$)alkoxycarbonyl group;

(e33) a methylenedioxy group formed by two adjacent substituents, wherein the methylenedioxy group is optionally substituted with one or two substituents selected from the group consisting of a halogen atom, a phenyl group, and a ($C_1$-$C_6$)alkyl group;

(e34) an N—($C_1$-$C_6$)alkylaminosulfonyl group;

(e35) an N,N-di($C_1$-$C_6$)alkylaminosulfonyl group;

(e36) an $R^6$—($R^7$—N=)O=S group, wherein $R^6$ represents a ($C_1$-$C_6$)alkyl group, a ($C_3$-$C_6$)cycloalkyl group, a halo($C_1$-$C_6$)alkyl group, or a ($C_1$-$C_6$)alkoxy($C_1$-$C_6$) alkyl group, and $R^7$ represents a hydrogen atom, a cyano group, a ($C_1$-$C_6$)alkyl group, a ($C_3$-$C_6$)cycloalkyl group, a halo($C_1$-$C_6$)alkyl group, a ($C_2$-$C_6$)alkylcarbonyl group, or a halo($C_2$-$C_6$)alkylcarbonyl group; and (e37) a substituted ($C_3$-$C_6$)cycloalkyl group having on the ring one to three substituents each independently selected from the group consisting of a halogen atom, a cyano group, a ($C_1$-$C_6$)alkyl group, a ($C_1$-$C_6$)alkoxy group, and a ($C_1$-$C_6$)alkylcarbonyl group, the substituent group B consists of (f1) a cyano group;

(f2) a ($C_3$-$C_6$)cycloalkyl group;

(f3) a ($C_1$-$C_6$)alkoxy group;

(f4) a ($C_1$-$C_6$)alkylthio group;

(f5) a ($C_1$-$C_6$)alkylsulfinyl group;

(f6) a ($C_1$-$C_6$)alkylsulfonyl group;

(f7) a halo($C_3$-$C_6$)cycloalkyl group;

(f8) a halo($C_1$-$C_6$)alkoxy group;

(f9) a halo($C_1$-$C_6$)alkylthio group;

(f10) a halo($C_1$-$C_6$)alkylsulfinyl group; and (f11) a halo($C_1$-$C_6$)alkylsulfonyl group, the substituent group C consists of (g1) a cyano group;

(g2) a ($C_1$-$C_6$)alkyl group;

(g3) a ($C_3$-$C_6$)cycloalkyl group;

(g4) a ($C_1$-$C_6$)alkoxy group;

(g5) a ($C_1$-$C_6$)alkylthio group;

(g6) a ($C_1$-$C_6$)alkylsulfinyl group;

(g7) a ($C_1$-$C_6$)alkylsulfonyl group;

(g8) a halo($C_3$-$C_6$)cycloalkyl group;

(g9) a halo($C_1$-$C_6$)alkoxy group;

(g10) a halo($C_1$-$C_6$)alkylthio group;

(g11) a halo($C_1$-$C_6$)alkylsulfinyl group;

(g12) a halo($C_1$-$C_6$)alkylsulfonyl group;

(g13) a halo($C_1$-$C_6$)alkyl group;

(g15) a ($C_2$-$C_6$)alkynyl group; and (g16) a phenyl group, and the substituent group D consists of (h1) a halogen atom;

(h2) a cyano group;

(h3) a hydroxyl group;

(h4) a carboxyl group;

(h5) a ($C_1$-$C_6$)alkyl group;

(h6) a ($C_1$-$C_6$)alkoxy group;

(h7) a ($C_3$-$C_6$)cycloalkyl group;

(h8) a ($C_1$-$C_6$)alkylthio group;

(h9) a ($C_1$-$C_6$)alkylsulfinyl group;

(h10) a ($C_1$-$C_6$)alkylsulfonyl group;

(h11) a halo($C_1$-$C_6$)alkyl group;

(h12) a halo($C_1$-$C_6$)alkoxy group;

(h13) a halo($C_3$-$C_6$)cycloalkyl group;

(h14) a halo($C_1$-$C_6$)alkylthio group;

(h15) a halo($C_1$-$C_6$)alkylsulfinyl group;

(h16) a halo($C_1$-$C_6$)alkylsulfonyl group;

(h17) a ($C_1$-$C_6$)alkoxycarbonyl group;

(h18) an N—($C_1$-$C_6$)alkylcarboxamide group;

(h20) a methylenedioxy group formed by two adjacent substituents, wherein the methylenedioxy group is optionally substituted with one or two substituents selected from the group consisting of a halogen atom, a phenyl group, and a ($C_1$-$C_6$)alkyl group;

(h21) a nitro group;

(h22) an amino group; and (h23) a benzyloxycarbonyl group.

4. The compound or a salt thereof according to claim 1, wherein $R^1$ is (a1) a hydrogen atom;

$R^2$ represents (b5) a phenyl group;
(b6) a substituted phenyl group having on the ring one to five substituents each independently selected from the substituent group A;
(b7) a pyridyl group;
(b8) a substituted pyridyl group having on the ring one to four substituents each independently selected from the substituent group A;
(b9) a pyridazinyl group;
(b10) a substituted pyridazinyl group having on the ring one to three substituents each independently selected from the substituent group A;
(b11) a pyrimidinyl group;
(b12) a substituted pyrimidinyl group having on the ring one to three substituents each independently selected from the substituent group A;
(b13) a pyrazinyl group;
(b14) a substituted pyrazinyl group having on the ring one to three substituents each independently selected from the substituent group A;
(b23) a pyrazolyl group;
(b24) a substituted pyrazolyl group having on the ring one to three substituents each independently selected from the substituent group A;
(b27) a triazolyl group;
(b28) a substituted triazolyl group having on the ring one to two substituents each independently selected from the substituent group A;
(b29) a thiazolyl group;
(b30) a substituted thiazolyl group having on the ring one to two substituents each independently selected from the substituent group A;
(b33) a thiadiazolyl group;
(b34) a substituted thiadiazolyl group having on the ring one substituent each independently selected from the substituent group A;
(b43) a benzothiazolyl group;
(b44) a substituted benzothiazolyl group having on the ring one to four substituents each independently selected from the substituent group A;
(b45) a thiazolopyridyl group;
(b46) a substituted thiazolopyridyl group having on the ring one to four substituents each independently selected from the substituent group A;
(b47) a quinolinyl group; or
(b48) a substituted quinolinyl group having on the ring one to six substituents each independently selected from the substituent group A, $R^3$ represents
(c1) a hydrogen atom; or
(c2) a $(C_1\text{-}C_6)$alkyl group, $R^4$ represents
(d1) a $(C_1\text{-}C_6)$alkyl group;
(d2) a $(C_2\text{-}C_6)$alkenyl group;
(d3) a $(C_2\text{-}C_6)$alkynyl group;
(d4) a $(C_3\text{-}C_6)$cycloalkyl group;
(d5) a halo$(C_1\text{-}C_6)$alkyl group;
(d8) a substituted $(C_1\text{-}C_6)$alkyl group having one to three substituents each independently selected from the substituent group B;
(d9) a substituted $(C_3\text{-}C_6)$cycloalkyl group having on the ring one to three substituents each independently selected from the substituent group C;
(d12) a phenyl group;
(d13) a substituted phenyl group having on the ring one to five substituents each independently selected from the substituent group D;
(d14) a phenyl$(C_1\text{-}C_6)$alkyl group;
(d15) a substituted phenyl$(C_1\text{-}C_6)$alkyl group having on the ring one to five substituents each independently selected from the substituent group D;
(d16) a pyridyl group;
(d17) a substituted pyridyl group having on the ring one to four substituents each independently selected from the substituent group D;
(d18) a pyridazinyl group;
(d19) a substituted pyridazinyl group having on the ring one to three substituents each independently selected from the substituent group D;
(d20) a pyrimidinyl group;
(d21) a substituted pyrimidinyl group having on the ring one to three substituents each independently selected from the substituent group D;
(d22) a pyrazinyl group;
(d24) a pyrazolyl group;
(d25) a substituted pyrazolyl group having on the ring one to three substituents each independently selected from the substituent group D;
(d26) an isoxazolyl group;
(d27) a substituted isoxazolyl group having on the ring one to two substituents each independently selected from the substituent group D;
(d32) a thiazolyl group;
(d33) a substituted thiazolyl group having on the ring one to two substituents each independently selected from the substituent group D;
(d34) a triazolyl group;
(d35) a substituted triazolyl group having on the ring one to two substituents each independently selected from the substituent group D;
(d36) a thiadiazolyl group;
(d37) a substituted thiadiazolyl group having on the ring one substituent each independently selected from the substituent group D;
(d42) a furyl$(C_1\text{-}C_6)$alkyl group;
(d43) a substituted furyl$(C_1\text{-}C_6)$alkyl group having on the ring one to three substituents each independently selected from the substituent group D;
(d44) a thienyl$(C_1\text{-}C_6)$alkyl group;
(d45) a substituted thienyl$(C_1\text{-}C_6)$alkyl group having on the ring one to three substituents each independently selected from the substituent group D;
(d46) a quinolinyl group;
(d47) a substituted quinolinyl group having on the ring one to six substituents each independently selected from the substituent group D;
(d48) a benzothiazolyl group;
(d49) a substituted benzothiazolyl group having on the ring one to four substituents each independently selected from the substituent group D;
(d50) a pyridyl$(C_1\text{-}C_6)$alkyl group;
(d51) a substituted pyridyl$(C_1\text{-}C_6)$alkyl group having on the ring one to four substituents each independently selected from the substituent group D;
(d52) a pyrazinyl$(C_1\text{-}C_6)$alkyl group;
(d53) a substituted pyrazinyl$(C_1\text{-}C_6)$alkyl group having on the ring one to three substituents each independently selected from the substituent group D;
(d54) a naphthyl group;
(d55) a substituted naphthyl group having on the ring one to seven substituents each independently selected from the substituent group D;
(d56) a tetrahydronaphthyl group; or (d57) a substituted tetrahydronaphthyl group having on the ring one to ten substituents each independently selected from the substituent group D, the substituent group A consists of (e1) a halogen atom;

(e2) a cyano group;

(e6) a $(C_1-C_6)$alkyl group;

(e9) a $(C_1-C_6)$alkoxy group;

(e11) a $(C_1-C_6)$alkylthio group;

(e12) a $(C_1-C_6)$alkylsulfinyl group;

(e13) a $(C_1-C_6)$alkylsulfonyl group;

(e14) a halo$(C_1-C_6)$alkyl group;

(e17) a halo$(C_1-C_6)$alkoxy group;

(e19) a halo$(C_1-C_6)$alkylthio group;

(e21) a halo$(C_1-C_6)$alkylsulfonyl group;

(e32) a $(C_1-C_6)$alkoxycarbonyl group;

(e34) an N—$(C_1-C_6)$alkylaminosulfonyl group; and (e35) an N,N-di$(C_1-C_6)$alkylaminosulfonyl group;

the substituent group B consists of (f1) a cyano group;

(f2) a $(C_3-C_6)$cycloalkyl group;

(f3) a $(C_1-C_6)$alkoxy group; and (f4) a $(C_1-C_6)$alkylthio group;

the substituent group C consists of (g1) a cyano group;

(g2) a $(C_1-C_6)$alkyl group;

(g13) a halo$(C_1-C_6)$alkyl group;

(g15) a $(C_2-C_6)$alkynyl group; and (g16) a phenyl group, the substituent group D consists of (h1) a halogen atom;

(h2) a cyano group;

(h3) a hydroxyl group;

(h5) a $(C_1-C_6)$alkyl group;

(h6) a $(C_1-C_6)$alkoxy group;

(h8) a $(C_1-C_6)$alkylthio group;

(h11) a halo$(C_1-C_6)$alkyl group;

(h12) a halo$(C_1-C_6)$alkoxy group;

(h17) a $(C_1-C_6)$alkoxycarbonyl group;

(h20) a methylenedioxy group formed by two adjacent substituents, wherein the methylenedioxy group is optionally substituted with one or two substituents selected from the group consisting of a halogen atom, a phenyl group, and a $(C_1-C_6)$alkyl group; and (h21) a nitro group.

5. A compound represented by general formula (13A):

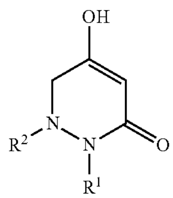

(13A)

wherein, $R^1$ represents (a1) a hydrogen atom;

(a2) a $(C_1-C_6)$alkyl group;

(a3) a $(C_2-C_6)$alkenyl group;

(a4) a $(C_2-C_6)$alkynyl group;

(a5) a $(C_3-C_6)$cycloalkyl group;

(a6) a $(C_1-C_6)$alkoxy group;

(a7) a halo$(C_1-C_6)$alkyl group;

(a8) a $(C_1-C_6)$alkylcarbonyl group;

(a9) a $(C_1-C_6)$alkoxycarbonyl group;

(a10) a substituted $(C_1-C_6)$alkyl group having on the chain one to three substituents each independently selected from the group consisting of a cyano group, a $(C_1-C_6)$alkoxy group, and a $(C_3-C_6)$cycloalkyl group;

(a11) a thiazolylmethyl group;

(a12) a substituted thiazolylmethyl group having on the ring one or two substituents each independently selected from the group consisting of a halogen atom, a $(C_1-C_6)$alkyl group, and a $(C_1-C_6)$alkoxy group;

(a13) a benzyl group; or (a14) a substituted benzyl group having on the ring one to three substituents each independently selected from the group consisting of a halogen atom, a $(C_1-C_6)$alkyl group, and a $(C_1-C_6)$alkoxy group, $R^2$ represents (b1) an aryl group;

(b2) a substituted aryl group having on the ring one or more substituents each independently selected from substituent group A;

(b3) a 5- to 10-membered ring heterocyclic group; or (b4) a substituted 5- to 10-membered ring heterocyclic group having on the ring one or more substituents each independently selected from the substituent group A, provided that $R^2$ does not have a substitution with a $(C_1-C_6)$alkylsulfonyl group, a halo$(C_1-C_6)$alkylsulfonyl group, an N—$(C_1-C_6)$alkylaminosulfonyl group, an N,N-di$(C_1-C_6)$alkylaminosulfonyl group, and an $R^6$—$(R^7$—N=)O=S group (wherein $R^6$ represents a $(C_1-C_6)$alkyl group, a $(C_3-C_6)$cycloalkyl group, a halo$(C_1-C_6)$alkyl group, or a $(C_1-C_6)$alkoxy$(C_1-C_6)$alkyl group, and $R^7$ represents a hydrogen atom, a cyano group, a $(C_1-C_6)$alkyl group, a $(C_3-C_6)$cycloalkyl group, a halo$(C_1-C_6)$alkyl group, a $(C_2-C_6)$alkylcarbonyl group, or a halo$(C_2-C_6)$alkylcarbonyl group) at an adjacent atom to an atom attached to the tetrahydropyridazine ring, the substituent group A consists of (e1) a halogen atom;

(e2) a cyano group;

(e3) a nitro group;

(e4) a hydroxyl group;

(e5) a carboxyl group;

(e6) a $(C_1-C_6)$alkyl group;

(e7) a $(C_2-C_6)$alkenyl group;

(e8) a $(C_2-C_6)$alkynyl group;

(e9) a $(C_1-C_6)$alkoxy group;

(e10) a $(C_3-C_6)$cycloalkyl group;

(e11) a $(C_1-C_6)$alkylthio group;

(e12) a $(C_1-C_6)$alkylsulfinyl group;

(e13) a $(C_1-C_6)$alkylsulfonyl group;

(e14) a halo$(C_1-C_6)$alkyl group;

(e15) a halo$(C_2-C_6)$alkenyl group;

(e16) a halo$(C_2-C_6)$alkynyl group;

(e17) a halo$(C_1-C_6)$alkoxy group;

(e18) a halo$(C_3-C_6)$cycloalkyl group;

(e19) a halo$(C_1-C_6)$alkylthio group;

(e20) a halo$(C_1-C_6)$alkylsulfinyl group;

(e21) a halo$(C_1-C_6)$alkylsulfonyl group;

(e22) a $(C_1-C_6)$alkylcarbonylamino group;

(e23) a halo$(C_1-C_6)$alkylcarbonylamino group;

(e24) a $(C_1-C_6)$alkylsulfonylamino group;

(e25) a halo$(C_1-C_6)$alkylsulfonylamino group;

(e26) an $SF_5$ group;

(e27) a $(C_1-C_6)$alkoxy$(C_1-C_6)$alkyl group;

(e28) an N—$(C_1-C_6)$alkylcarboxamide group;

(e29) an N-halo$(C_1-C_6)$alkylcarboxamide group;

(e30) an oxadiazolyl group;

(e31) a substituted oxadiazolyl group having on the ring one substituent each independently selected from the group consisting of a halogen atom, a cyano group, a $(C_1-C_6)$alkyl group, a $(C_1-C_6)$alkoxy group, a $(C_3-C_6)$ cycloalkyl group, a $(C_1-C_6)$alkylthio group, a $(C_1-C_6)$ alkylsulfinyl group, a $(C_1-C_6)$alkylsulfonyl group, a halo$(C_1-C_6)$alkyl group, and a halo$(C_1-C_6)$alkoxy group;

(e32) a $(C_1-C_6)$alkoxycarbonyl group;

(e33) a methylenedioxy group formed by two adjacent substituents, wherein the methylenedioxy group is optionally substituted with one or two substituents selected from the group consisting of a halogen atom, a phenyl group, and a $(C_1-C_6)$alkyl group;

(e34) an N—$(C_1-C_6)$alkylaminosulfonyl group;

(e35) an N,N-di$(C_1-C_6)$alkylaminosulfonyl group;

(e36) an $R^6$—($R^7$—N=)O=S group, wherein $R^6$ represents a $(C_1-C_6)$alkyl group, a $(C_3-C_6)$cycloalkyl group, a halo$(C_1-C_6)$alkyl group, or a $(C_1-C_6)$alkoxy$(C_1-C_6)$ alkyl group, and $R^7$ represents a hydrogen atom, a cyano group, a $(C_1-C_6)$alkyl group, a $(C_3-C_6)$cycloalkyl group, a halo$(C_1-C_6)$alkyl group, a $(C_2-C_6)$alkylcarbonyl group, or a halo$(C_2-C_6)$alkylcarbonyl group; and (e37) a substituted $(C_3-C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group, or a salt thereof.

6. The compound or a salt thereof according to claim 5, wherein $R^1$ and the substituent group A are as defined in claim 5, and $R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b15) a furyl group;

(b16) a substituted furyl group having on the ring one to three substituents each independently selected from the substituent group A;

(b17) a thienyl group;

(b18) a substituted thienyl group having on the ring one to three substituents each independently selected from the substituent group A;

(b19) an isoxazolyl group;

(b20) a substituted isoxazolyl group having on the ring one to two substituents each independently selected from the substituent group A;

(b21) an oxazolyl group;

(b22) a substituted oxazolyl group having on the ring one to two substituents each independently selected from the substituent group A;

(b23) a pyrazolyl group;

(b24) a substituted pyrazolyl group having on the ring one to three substituents each independently selected from the substituent group A;

(b25) an imidazolyl group;

(b26) a substituted imidazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b31) an isothiazolyl group;

(b32) a substituted isothiazolyl group having on the ring one to two substituents each independently selected from the substituent group A;

(b33) a thiadiazolyl group;

(b34) a substituted thiadiazolyl group having on the ring one substituent each independently selected from the substituent group A;

(b35) an imidazopyridyl group;

(b36) a substituted imidazopyridyl group having on the ring one to five substituents each independently selected from the substituent group A;

(b37) a quinoxalinyl group;

(b38) a substituted quinoxalinyl group having on the ring one to five substituents each independently selected from the substituent group A;

(b39) a benzoxazolyl group;

(b40) a substituted benzoxazolyl group having on the ring one to four substituents each independently selected from the substituent group A;

(b41) a benzimidazolyl group;

(b42) a substituted benzimidazolyl group having on the ring one to five substituents each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group;

(b48) a substituted quinolinyl group having on the ring one to six substituents each independently selected from the substituent group A;

(b49) a naphthyl group;

(b50) a substituted naphthyl group having on the ring one to seven substituents each independently selected from the substituent group A;

(b51) a triazinyl group;

(b52) a substituted triazinyl group having on the ring one to two substituents each independently selected from the substituent group A;

(b53) a pyrrolyl group;

(b54) a substituted pyrrolyl group having on the ring one to four substituents each independently selected from the substituent group A;

(b55) a tetrazolyl group;

(b56) a substituted tetrazolyl group having on the ring one substituent each independently selected from the substituent group A;

(b57) an oxadiazonyl group;

(b58) a substituted oxadiazonyl group having on the ring one substituent each independently selected from the substituent group A;

(b59) a 2-oxopyridyl group;

(b60) a substituted 2-oxopyridyl group having on the ring one to four substituents each independently selected from the substituent group A;

(b61) a benzofuranyl group;

(b62) a substituted benzofuranyl group having on the ring one to five substituents each independently selected from the substituent group A;

(b63) a benzisoxazolyl group;

(b64) a substituted benzisoxazolyl group having on the ring one to four substituents each independently selected from the substituent group A;

(b65) a benzothienyl group;

(b66) a substituted benzothienyl group having on the ring one to five substituents each independently selected from the substituent group A;

(b67) a benzisothiazolyl group;

(b68) a substituted benzisothiazolyl group having on the ring one to four substituents each independently selected from the substituent group A;

(b69) an indolyl group;

(b70) a substituted indolyl group having on the ring one to six substituents each independently selected from the substituent group A;

(b71) an isoindolyl group;

(b72) a substituted isoindolyl group having on the ring one to six substituents each independently selected from the substituent group A;

(b73) an indazolyl group;

(b74) a substituted indazolyl group having on the ring one to five substituents each independently selected from the substituent group A;

(b75) a benzotriazolyl group;

(b76) a substituted benzotriazolyl group having on the ring one to four substituents each independently selected from the substituent group A;

(b77) a furopyridyl group;

(b78) a substituted furopyridyl group having on the ring one to four substituents each independently selected from the substituent group A;

(b79) a thienopyridyl group;

(b80) a substituted thienopyridyl group having on the ring one to four substituents each independently selected from the substituent group A;

(b81) an indolizinyl group;

(b82) a substituted indolizinyl group having on the ring one to six substituents each independently selected from the substituent group A;

(b83) a pyrrolopyridyl group;

(b84) a substituted pyrrolopyridyl group having on the ring one to five substituents each independently selected from the substituent group A;

(b85) a pyrrolopyrimidinyl group;

(b86) a substituted pyrrolopyrimidinyl group having on the ring one to five substituents each independently selected from the substituent group A;

(b87) an oxazolopyridyl group;

(b88) a substituted oxazolopyridyl group having on the ring one to three substituents each independently selected from the substituent group A;

(b89) an isoxazolopyridyl group;

(b90) a substituted isoxazolopyridyl group having on the ring one to three substituents each independently selected from the substituent group A;

(b91) an isothiazolopyridyl group;

(b92) a substituted isothiazolopyridyl group having on the ring one to three substituents each independently selected from the substituent group A;

(b93) an imidazopyrimidinyl group;

(b94) a substituted imidazopyrimidinyl group having on the ring one to five substituents each independently selected from the substituent group A;

(b95) a pyrazolopyridyl group;

(b96) a substituted pyrazolopyridyl group having on the ring one to five substituents each independently selected from the substituent group A;

(b97) a pyrazolopyrimidinyl group;

(b98) a substituted pyrazolopyrimidinyl group having on the ring one to five substituents each independently selected from the substituent group A;

(b99) a triazolopyridyl group;

(b100) a substituted triazolopyridyl group having on the ring one to four substituents each independently selected from the substituent group A;

(b101) a triazolopyrimidinyl group;

(b102) a substituted triazolopyrimidinyl group having on the ring one to four substituents each independently selected from the substituent group A;

(b103) an isoquinolinyl group;

(b104) a substituted isoquinolinyl group having on the ring one to six substituents each independently selected from the substituent group A;

(b105) a cinnolinyl group;

(b106) a substituted cinnolinyl group having on the ring one to five substituents each independently selected from the substituent group A;

(b107) a phthalazinyl group;

(b108) a substituted phthalazinyl group having on the ring one to five substituents each independently selected from the substituent group A;

(b109) a quinazolinyl group;

(b110) a substituted quinazolinyl group having on the ring one to five substituents each independently selected from the substituent group A;

(b111) a naphthyridinyl group; or (b112) a substituted naphthyridinyl group having on the ring one to five substituents each independently selected from the substituent group A.

7. The compound or a salt thereof according to claim 5, wherein $R^1$ represents (a1) a hydrogen atom;

(a2) a $(C_1-C_6)$alkyl group; or (a4) a $(C_2-C_6)$alkynyl group, $R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b15) a furyl group;

(b16) a substituted furyl group having on the ring one to three substituents each independently selected from the substituent group A;

(b17) a thienyl group;

(b18) a substituted thienyl group having on the ring one to three substituents each independently selected from the substituent group A;

(b19) an isoxazolyl group;

(b20) a substituted isoxazolyl group having on the ring one to two substituents each independently selected from the substituent group A;

(b21) an oxazolyl group;

(b22) a substituted oxazolyl group having on the ring one to two substituents each independently selected from the substituent group A;

(b23) a pyrazolyl group;

(b24) a substituted pyrazolyl group having on the ring one to three substituents each independently selected from the substituent group A;

(b25) an imidazolyl group;

(b26) a substituted imidazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b31) an isothiazolyl group;

(b32) a substituted isothiazolyl group having on the ring one to two substituents each independently selected from the substituent group A;

(b33) a thiadiazolyl group;

(b34) a substituted thiadiazolyl group having on the ring one substituent each independently selected from the substituent group A;

(b35) an imidazopyridyl group;

(b36) a substituted imidazopyridyl group having on the ring one to five substituents each independently selected from the substituent group A;

(b37) a quinoxalinyl group;

(b38) a substituted quinoxalinyl group having on the ring one to five substituents each independently selected from the substituent group A;

(b39) a benzoxazolyl group;

(b40) a substituted benzoxazolyl group having on the ring one to four substituents each independently selected from the substituent group A;

(b41) a benzimidazolyl group;

(b42) a substituted benzimidazolyl group having on the ring one to five substituents each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group; or (b48) a substituted quinolinyl group having on the ring one to six substituents each independently selected from the substituent group A, the substituent group A consists of (e1) a halogen atom;

(e2) a cyano group;

(e4) a hydroxyl group;

(e5) a carboxyl group;

(e6) a $(C_1-C_6)$alkyl group;

(e9) a $(C_1-C_6)$alkoxy group;

(e10) a $(C_3-C_6)$cycloalkyl group;

(e11) a $(C_1-C_6)$alkylthio group;

(e12) a $(C_1-C_6)$alkylsulfinyl group;

(e13) a $(C_1-C_6)$alkylsulfonyl group;

(e14) a halo$(C_1-C_6)$alkyl group;

(e17) a halo$(C_1-C_6)$alkoxy group;

(e18) a halo$(C_3-C_6)$cycloalkyl group;

(e19) a halo$(C_1-C_6)$alkylthio group;

(e20) a halo$(C_1-C_6)$alkylsulfinyl group;

(e21) a halo$(C_1-C_6)$alkylsulfonyl group;

(e22) a $(C_1-C_6)$alkylcarbonylamino group;

(e24) a $(C_1-C_6)$alkylsulfonylamino group;

(e28) an N—$(C_1-C_6)$alkylcarboxamide group;

(e30) an oxadiazolyl group;

(e31) a substituted oxadiazolyl group having on the ring one substituent each independently selected from the group consisting of a halogen atom, a cyano group, a $(C_1-C_6)$alkyl group, a $(C_1-C_6)$alkoxy group, a $(C_3-C_6)$cycloalkyl group, a $(C_1-C_6)$alkylthio group, a $(C_1-C_6)$alkylsulfinyl group, a $(C_1-C_6)$alkylsulfonyl group, a halo$(C_1-C_6)$alkyl group, and a halo$(C_1-C_6)$alkoxy group;

(e32) a $(C_1-C_6)$alkoxycarbonyl group;

(e33) a methylenedioxy group formed by two adjacent substituents, wherein the methylenedioxy group is optionally substituted with one or two substituents selected from the group consisting of a halogen atom, a phenyl group, and a $(C_1-C_6)$alkyl group;

(e34) an N—$(C_1-C_6)$alkylaminosulfonyl group;

(e35) an N,N-di$(C_1-C_6)$alkylaminosulfonyl group;

(e36) an $R^6$—($R^7$—N=)O=S group, wherein $R^6$ represents a $(C_1-C_6)$alkyl group, a $(C_3-C_6)$cycloalkyl group, a halo$(C_1-C_6)$alkyl group, or a $(C_1-C_6)$alkoxy$(C_1-C_6)$alkyl group, and $R^7$ represents a hydrogen atom, a cyano group, a $(C_1-C_6)$alkyl group, a $(C_3-C_6)$cycloalkyl group, a halo$(C_1-C_6)$alkyl group, a $(C_2-C_6)$alkylcarbonyl group, or a halo$(C_2-C_6)$alkylcarbonyl group; and (e37) a substituted $(C_3-C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group.

8. The compound or a salt thereof according to claim 5, wherein $R^1$ is (a1) a hydrogen atom;

$R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b23) a pyrazolyl group;

(b24) a substituted pyrazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b33) a thiadiazolyl group;

(b34) a substituted thiadiazolyl group having on the ring one substituent each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group; or (b48) a substituted quinolinyl group having on the ring one to six substituents each independently selected from the substituent group A, and the substituent group A consists of (e1) a halogen atom;

(e2) a cyano group;

(e6) a $(C_1-C_6)$alkyl group;

(e9) a $(C_1-C_6)$alkoxy group;

(e11) a $(C_1-C_6)$alkylthio group;

(e12) a $(C_1-C_6)$alkylsulfinyl group;

(e13) a $(C_1-C_6)$alkylsulfonyl group;

(e14) a halo$(C_1-C_6)$alkyl group;

(e17) a halo$(C_1-C_6)$alkoxy group;

(e19) a halo$(C_1-C_6)$alkylthio group;

(e21) a halo$(C_1-C_6)$alkylsulfonyl group;

(e32) a $(C_1-C_6)$alkoxycarbonyl group;

(e34) an N—$(C_1-C_6)$alkylaminosulfonyl group; and (e35) an N,N-di$(C_1-C_6)$alkylaminosulfonyl group.

9. A compound represented by general formula (3A):

(3A)

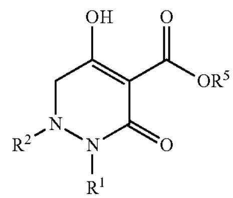

wherein, $R^1$ represents (a1) a hydrogen atom;

(a2) a $(C_1-C_6)$alkyl group;

(a3) a $(C_2-C_6)$alkenyl group;

(a4) a $(C_2-C_6)$alkynyl group;

(a5) a $(C_3-C_6)$cycloalkyl group;

(a6) a $(C_1-C_6)$alkoxy group;

(a7) a halo$(C_1-C_6)$alkyl group;

(a8) a $(C_1-C_6)$alkylcarbonyl group;

(a9) a $(C_1-C_6)$alkoxycarbonyl group;

(a10) a substituted $(C_1-C_6)$alkyl group having on the chain one to three substituents each independently selected from the group consisting of a cyano group, a $(C_1-C_6)$alkoxy group, and a $(C_3-C_6)$cycloalkyl group;

(a11) a thiazolylmethyl group;

(a12) a substituted thiazolylmethyl group having on the ring one or two substituents each independently selected from the group consisting of a halogen atom, a $(C_1-C_6)$alkyl group, and a $(C_1-C_6)$alkoxy group;

(a13) a benzyl group; or (a14) a substituted benzyl group having on the ring one to three substituents each independently selected from the group consisting of a halogen atom, a $(C_1-C_6)$alkyl group, and a $(C_1-C_6)$alkoxy group, $R^2$ represents (b1) an aryl group;

(b2) a substituted aryl group having on the ring one or more substituents each independently selected from substituent group A;

(b3) a 5- to 10-membered ring heterocyclic group; or (b4) a substituted 5- to 10-membered ring heterocyclic group having on the ring one or more substituents each independently selected from the substituent group A, provided that $R^2$ does not have a substitution with a $(C_1-C_6)$alkylsulfonyl group, a halo$(C_1-C_6)$alkylsulfonyl group, an N—$(C_1-C_6)$alkylaminosulfonyl group, an N,N-di$(C_1-C_6)$alkylaminosulfonyl group, and an $R^6$—$(R^7$—N=)O=S group (wherein $R^6$ represents a $(C_1-C_6)$alkyl group, a $(C_3-C_6)$cycloalkyl group, a halo$(C_1-C_6)$alkyl group, or a $(C_1-C_6)$alkoxy$(C_1-C_6)$alkyl group, and $R^7$ represents a hydrogen atom, a cyano group, a $(C_1-C_6)$alkyl group, a $(C_3-C_6)$cycloalkyl group, a halo$(C_1-C_6)$alkyl group, a $(C_2-C_6)$alkylcarbonyl group, or a halo$(C_2-C_6)$alkylcarbonyl group) at an adjacent atom to an atom attached to the tetrahydropyridazine ring, $R^5$ represents (i1) a $(C_1-C_6)$alkyl group; or (i2) a $(C_1-C_6)$alkoxy$(C_1-C_6)$alkyl group, and the substituent group A consists of (e1) a halogen atom;

(e2) a cyano group;

(e3) a nitro group;

(e4) a hydroxyl group;

(e5) a carboxyl group;
(e6) a $(C_1-C_6)$alkyl group;
(e7) a $(C_2-C_6)$alkenyl group;
(e8) a $(C_2-C_6)$alkynyl group;
(e9) a $(C_1-C_6)$alkoxy group;
(e10) a $(C_3-C_6)$cycloalkyl group;
(e11) a $(C_1-C_6)$alkylthio group;
(e12) a $(C_1-C_6)$alkylsulfinyl group;
(e13) a $(C_1-C_6)$alkylsulfonyl group;
(e14) a halo$(C_1-C_6)$alkyl group;
(e15) a halo$(C_2-C_6)$alkenyl group;
(e16) a halo$(C_2-C_6)$alkynyl group;
(e17) a halo$(C_1-C_6)$alkoxy group;
(e18) a halo$(C_3-C_6)$cycloalkyl group;
(e19) a halo$(C_1-C_6)$alkylthio group;
(e20) a halo$(C_1-C_6)$alkylsulfinyl group;
(e21) a halo$(C_1-C_6)$alkylsulfonyl group;
(e22) a $(C_1-C_6)$alkylcarbonylamino group;
(e23) a halo$(C_1-C_6)$alkylcarbonylamino group;
(e24) a $(C_1-C_6)$alkylsulfonylamino group;
(e25) a halo$(C_1-C_6)$alkylsulfonylamino group;
(e26) an $SF_5$ group;
(e27) a $(C_1-C_6)$alkoxy$(C_1-C_6)$alkyl group;
(e28) an N—$(C_1-C_6)$alkylcarboxamide group;
(e29) an N-halo$(C_1-C_6)$alkylcarboxamide group;
(e30) an oxadiazolyl group;
(e31) a substituted oxadiazolyl group having on the ring one substituent each independently selected from the group consisting of a halogen atom, a cyano group, a $(C_1-C_6)$alkyl group, a $(C_1-C_6)$alkoxy group, a $(C_3-C_6)$cycloalkyl group, a $(C_1-C_6)$alkylthio group, a $(C_1-C_6)$alkylsulfinyl group, a $(C_1-C_6)$alkylsulfonyl group, a halo$(C_1-C_6)$alkyl group, and a halo$(C_1-C_6)$alkoxy group;
(e32) a $(C_1-C_6)$alkoxycarbonyl group;
(e33) a methylenedioxy group formed by two adjacent substituents, wherein the methylenedioxy group is optionally substituted with one or two substituents selected from the group consisting of a halogen atom, a phenyl group, and a $(C_1-C_6)$alkyl group;
(e34) an N—$(C_1-C_6)$alkylaminosulfonyl group;
(e35) an N,N-di$(C_1-C_6)$alkylaminosulfonyl group;
(e36) an $R^6$—($R^7$—N=)O=S group, wherein $R^6$ represents a $(C_1-C_6)$alkyl group, a $(C_3-C_6)$cycloalkyl group, a halo$(C_1-C_6)$alkyl group, or a $(C_1-C_6)$alkoxy$(C_1-C_6)$alkyl group, and $R^7$ represents a hydrogen atom, a cyano group, a $(C_1-C_6)$alkyl group, a $(C_3-C_6)$cycloalkyl group, a halo$(C_1-C_6)$alkyl group, a $(C_2-C_6)$alkylcarbonyl group, or a halo$(C_2-C_6)$alkylcarbonyl group; and
(e37) a substituted $(C_3-C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group, or a salt thereof.

10. The compound or a salt thereof according to claim 9, wherein $R^1$, $R^5$, and the substituent group A are as defined in claim 9, and $R^2$ represents (b5) a phenyl group;
(b6) a substituted phenyl group having on the ring one to five substituents each independently selected from the substituent group A;
(b7) a pyridyl group;
(b8) a substituted pyridyl group having on the ring one to four substituents each independently selected from the substituent group A;
(b9) a pyridazinyl group;
(b10) a substituted pyridazinyl group having on the ring one to three substituents each independently selected from the substituent group A;
(b11) a pyrimidinyl group;
(b12) a substituted pyrimidinyl group having on the ring one to three substituents each independently selected from the substituent group A;
(b13) a pyrazinyl group;
(b14) a substituted pyrazinyl group having on the ring one to three substituents each independently selected from the substituent group A;
(b15) a furyl group;
(b16) a substituted furyl group having on the ring one to three substituents each independently selected from the substituent group A;
(b17) a thienyl group;
(b18) a substituted thienyl group having on the ring one to three substituents each independently selected from the substituent group A;
(b19) an isoxazolyl group;
(b20) a substituted isoxazolyl group having on the ring one to two substituents each independently selected from the substituent group A;
(b21) an oxazolyl group;
(b22) a substituted oxazolyl group having on the ring one to two substituents each independently selected from the substituent group A;
(b23) a pyrazolyl group;
(b24) a substituted pyrazolyl group having on the ring one to three substituents each independently selected from the substituent group A;
(b25) an imidazolyl group;
(b26) a substituted imidazolyl group having on the ring one to three substituents each independently selected from the substituent group A;
(b27) a triazolyl group;
(b28) a substituted triazolyl group having on the ring one to two substituents each independently selected from the substituent group A;
(b29) a thiazolyl group;
(b30) a substituted thiazolyl group having on the ring one to two substituents each independently selected from the substituent group A;
(b31) an isothiazolyl group;
(b32) a substituted isothiazolyl group having on the ring one to two substituents each independently selected from the substituent group A;
(b33) a thiadiazolyl group;
(b34) a substituted thiadiazolyl group having on the ring one substituent each independently selected from the substituent group A;
(b35) an imidazopyridyl group;
(b36) a substituted imidazopyridyl group having on the ring one to five substituents each independently selected from the substituent group A;
(b37) a quinoxalinyl group;
(b38) a substituted quinoxalinyl group having on the ring one to five substituents each independently selected from the substituent group A;
(b39) a benzoxazolyl group;
(b40) a substituted benzoxazolyl group having on the ring one to four substituents each independently selected from the substituent group A;

(b41) a benzimidazolyl group;
(b42) a substituted benzimidazolyl group having on the ring one to five substituents each independently selected from the substituent group A;
(b43) a benzothiazolyl group;
(b44) a substituted benzothiazolyl group having on the ring one to four substituents each independently selected from the substituent group A;
(b45) a thiazolopyridyl group;
(b46) a substituted thiazolopyridyl group having on the ring one to four substituents each independently selected from the substituent group A;
(b47) a quinolinyl group;
(b48) a substituted quinolinyl group having on the ring one to six substituents each independently selected from the substituent group A;
(b49) a naphthyl group;
(b50) a substituted naphthyl group having on the ring one to seven substituents each independently selected from the substituent group A;
(b51) a triazinyl group;
(b52) a substituted triazinyl group having on the ring one to two substituents each independently selected from the substituent group A;
(b53) a pyrrolyl group;
(b54) a substituted pyrrolyl group having on the ring one to four substituents each independently selected from the substituent group A;
(b55) a tetrazolyl group;
(b56) a substituted tetrazolyl group having on the ring one substituent each independently selected from the substituent group A;
(b57) an oxadiazonyl group;
(b58) a substituted oxadiazonyl group having on the ring one substituent each independently selected from the substituent group A;
(b59) a 2-oxopyridyl group;
(b60) a substituted 2-oxopyridyl group having on the ring one to four substituents each independently selected from the substituent group A;
(b61) a benzofuranyl group;
(b62) a substituted benzofuranyl group having on the ring one to five substituents each independently selected from the substituent group A;
(b63) a benzisoxazolyl group;
(b64) a substituted benzisoxazolyl group having on the ring one to four substituents each independently selected from the substituent group A;
(b65) a benzothienyl group;
(b66) a substituted benzothienyl group having on the ring one to five substituents each independently selected from the substituent group A;
(b67) a benzisothiazolyl group;
(b68) a substituted benzisothiazolyl group having on the ring one to four substituents each independently selected from the substituent group A;
(b69) an indolyl group;
(b70) a substituted indolyl group having on the ring one to six substituents each independently selected from the substituent group A;
(b71) an isoindolyl group;
(b72) a substituted isoindolyl group having on the ring one to six substituents each independently selected from the substituent group A;
(b73) an indazolyl group;
(b74) a substituted indazolyl group having on the ring one to five substituents each independently selected from the substituent group A;
(b75) a benzotriazolyl group;
(b76) a substituted benzotriazolyl group having on the ring one to four substituents each independently selected from the substituent group A;
(b77) a furopyridyl group;
(b78) a substituted furopyridyl group having on the ring one to four substituents each independently selected from the substituent group A;
(b79) a thienopyridyl group;
(b80) a substituted thienopyridyl group having on the ring one to four substituents each independently selected from the substituent group A;
(b81) an indolizinyl group;
(b82) a substituted indolizinyl group having on the ring one to six substituents each independently selected from the substituent group A;
(b83) a pyrrolopyridyl group;
(b84) a substituted pyrrolopyridyl group having on the ring one to five substituents each independently selected from the substituent group A;
(b85) a pyrrolopyrimidinyl group;
(b86) a substituted pyrrolopyrimidinyl group having on the ring one to five substituents each independently selected from the substituent group A;
(b87) an oxazolopyridyl group;
(b88) a substituted oxazolopyridyl group having on the ring one to three substituents each independently selected from the substituent group A;
(b89) an isoxazolopyridyl group;
(b90) a substituted isoxazolopyridyl group having on the ring one to three substituents each independently selected from the substituent group A;
(b91) an isothiazolopyridyl group;
(b92) a substituted isothiazolopyridyl group having on the ring one to three substituents each independently selected from the substituent group A;
(b93) an imidazopyrimidinyl group;
(b94) a substituted imidazopyrimidinyl group having on the ring one to five substituents each independently selected from the substituent group A;
(b95) a pyrazolopyridyl group;
(b96) a substituted pyrazolopyridyl group having on the ring one to five substituents each independently selected from the substituent group A;
(b97) a pyrazolopyrimidinyl group;
(b98) a substituted pyrazolopyrimidinyl group having on the ring one to five substituents each independently selected from the substituent group A;
(b99) a triazolopyridyl group;
(b100) a substituted triazolopyridyl group having on the ring one to four substituents each independently selected from the substituent group A;
(b101) a triazolopyrimidinyl group;
(b102) a substituted triazolopyrimidinyl group having on the ring one to four substituents each independently selected from the substituent group A;
(b103) an isoquinolinyl group;
(b104) a substituted isoquinolinyl group having on the ring one to six substituents each independently selected from the substituent group A;
(b105) a cinnolinyl group;
(b106) a substituted cinnolinyl group having on the ring one to five substituents each independently selected from the substituent group A;

(b107) a phthalazinyl group;
(b108) a substituted phthalazinyl group having on the ring one to five substituents each independently selected from the substituent group A;
(b109) a quinazolinyl group;
(b110) a substituted quinazolinyl group having on the ring one to five substituents each independently selected from the substituent group A;
(b111) a naphthyridinyl group; or
(b112) a substituted naphthyridinyl group having on the ring one to five substituents each independently selected from the substituent group A.

11. The compound or a salt thereof according to claim 9, wherein $R^1$ represents
(a1) a hydrogen atom;
(a2) a $(C_1-C_6)$alkyl group; or
(a4) a $(C_2-C_6)$alkynyl group;
$R^2$ represents
(b5) a phenyl group;
(b6) a substituted phenyl group having on the ring one to five substituents each independently selected from the substituent group A;
(b7) a pyridyl group;
(b8) a substituted pyridyl group having on the ring one to four substituents each independently selected from the substituent group A;
(b9) a pyridazinyl group;
(b10) a substituted pyridazinyl group having on the ring one to three substituents each independently selected from the substituent group A;
(b11) a pyrimidinyl group;
(b12) a substituted pyrimidinyl group having on the ring one to three substituents each independently selected from the substituent group A;
(b13) a pyrazinyl group;
(b14) a substituted pyrazinyl group having on the ring one to three substituents each independently selected from the substituent group A;
(b15) a furyl group;
(b16) a substituted furyl group having on the ring one to three substituents each independently selected from the substituent group A;
(b17) a thienyl group;
(b18) a substituted thienyl group having on the ring one to three substituents each independently selected from the substituent group A;
(b19) an isoxazolyl group;
(b20) a substituted isoxazolyl group having on the ring one to two substituents each independently selected from the substituent group A;
(b21) an oxazolyl group;
(b22) a substituted oxazolyl group having on the ring one to two substituents each independently selected from the substituent group A;
(b23) a pyrazolyl group;
(b24) a substituted pyrazolyl group having on the ring one to three substituents each independently selected from the substituent group A;
(b25) an imidazolyl group;
(b26) a substituted imidazolyl group having on the ring one to three substituents each independently selected from the substituent group A;
(b27) a triazolyl group;
(b28) a substituted triazolyl group having on the ring one to two substituents each independently selected from the substituent group A;
(b29) a thiazolyl group;
(b30) a substituted thiazolyl group having on the ring one to two substituents each independently selected from the substituent group A;
(b31) an isothiazolyl group;
(b32) a substituted isothiazolyl group having on the ring one to two substituents each independently selected from the substituent group A;
(b33) a thiadiazolyl group;
(b34) a substituted thiadiazolyl group having on the ring one substituent each independently selected from the substituent group A;
(b35) an imidazopyridyl group;
(b36) a substituted imidazopyridyl group having on the ring one to five substituents each independently selected from the substituent group A;
(b37) a quinoxalinyl group;
(b38) a substituted quinoxalinyl group having on the ring one to five substituents each independently selected from the substituent group A;
(b39) a benzoxazolyl group;
(b40) a substituted benzoxazolyl group having on the ring one to four substituents each independently selected from the substituent group A;
(b41) a benzimidazolyl group;
(b42) a substituted benzimidazolyl group having on the ring one to five substituents each independently selected from the substituent group A;
(b43) a benzothiazolyl group;
(b44) a substituted benzothiazolyl group having on the ring one to four substituents each independently selected from the substituent group A;
(b45) a thiazolopyridyl group;
(b46) a substituted thiazolopyridyl group having on the ring one to four substituents each independently selected from the substituent group A;
(b47) a quinolinyl group; or
(b48) a substituted quinolinyl group having on the ring one to six substituents each independently selected from the substituent group A,
$R^5$ represents
(i1) a $(C_1-C_6)$alkyl group; or
(i2) a $(C_1-C_6)$alkoxy$(C_1-C_6)$alkyl group, and
the substituent group A consists of
(e1) a halogen atom;
(e2) a cyano group;
(e4) a hydroxyl group;
(e5) a carboxyl group;
(e6) a $(C_1-C_6)$alkyl group;
(e9) a $(C_1-C_6)$alkoxy group;
(e10) a $(C_3-C_6)$cycloalkyl group;
(e11) a $(C_1-C_6)$alkylthio group;
(e12) a $(C_1-C_6)$alkylsulfinyl group;
(e13) a $(C_1-C_6)$alkylsulfonyl group;
(e14) a halo$(C_1-C_6)$alkyl group;
(e17) a halo$(C_1-C_6)$alkoxy group;
(e18) a halo$(C_3-C_6)$cycloalkyl group;
(e19) a halo$(C_1-C_6)$alkylthio group;
(e20) a halo$(C_1-C_6)$alkylsulfinyl group;
(e21) a halo$(C_1-C_6)$alkylsulfonyl group;
(e22) a $(C_1-C_6)$alkylcarbonylamino group;
(e24) a $(C_1-C_6)$alkylsulfonylamino group;
(e28) an N—$(C_1-C_6)$alkylcarboxamide group;
(e30) an oxadiazolyl group;
(e31) a substituted oxadiazolyl group having on the ring one substituent each independently selected from the group consisting of a halogen atom, a cyano group, a $(C_1-C_6)$alkyl group, a $(C_1-C_6)$alkoxy group, a $(C_3-C_6)$cycloalkyl group, a $(C_1-C_6)$alkylthio group, a $(C_1-C_6)$alkylsulfinyl group, a $(C_1-C_6)$alkylsulfonyl group, a halo$(C_1-C_6)$alkyl group, and a halo$(C_1-C_6)$alkoxy group;

(e32) a $(C_1-C_6)$alkoxycarbonyl group;

(e33) a methylenedioxy group formed by two adjacent substituents, wherein the methylenedioxy group is optionally substituted with one or two substituents selected from the group consisting of a halogen atom, a phenyl group, and a $(C_1-C_6)$alkyl group;

(e34) an N—$(C_1-C_6)$alkylaminosulfonyl group;

(e35) an N,N-di$(C_1-C_6)$alkylaminosulfonyl group;

(e36) an $R^6$—($R^7$—N=)O=S group, wherein $R^6$ represents a $(C_1-C_6)$alkyl group, a $(C_3-C_6)$cycloalkyl group, a halo$(C_1-C_6)$alkyl group, or a $(C_1-C_6)$alkoxy$(C_1-C_6)$alkyl group, and $R^7$ represents a hydrogen atom, a cyano group, a $(C_1-C_6)$alkyl group, a $(C_3-C_6)$cycloalkyl group, a halo$(C_1-C_6)$alkyl group, a $(C_2-C_6)$alkylcarbonyl group, or a halo$(C_2-C_6)$alkylcarbonyl group; and (e37) a substituted $(C_3-C_6)$cycloalkyl group having on the ring one to three substituents each independently selected from the group consisting of a halogen atom, a cyano group, a $(C_1-C_6)$alkyl group, a $(C_1-C_6)$alkoxy group, and a $(C_1-C_6)$alkylcarbonyl group.

12. The compound or a salt thereof according to claim 9, wherein $R^1$ is (a1) a hydrogen atom;

$R^2$ represents (b5) a phenyl group;

(b6) a substituted phenyl group having on the ring one to five substituents each independently selected from the substituent group A;

(b7) a pyridyl group;

(b8) a substituted pyridyl group having on the ring one to four substituents each independently selected from the substituent group A;

(b9) a pyridazinyl group;

(b10) a substituted pyridazinyl group having on the ring one to three substituents each independently selected from the substituent group A;

(b11) a pyrimidinyl group;

(b12) a substituted pyrimidinyl group having on the ring one to three substituents each independently selected from the substituent group A;

(b13) a pyrazinyl group;

(b14) a substituted pyrazinyl group having on the ring one to three substituents each independently selected from the substituent group A;

(b23) a pyrazolyl group;

(b24) a substituted pyrazolyl group having on the ring one to three substituents each independently selected from the substituent group A;

(b27) a triazolyl group;

(b28) a substituted triazolyl group having on the ring one to two substituents each independently selected from the substituent group A;

(b29) a thiazolyl group;

(b30) a substituted thiazolyl group having on the ring one to two substituents each independently selected from the substituent group A;

(b33) a thiadiazolyl group;

(b34) a substituted thiadiazolyl group having on the ring one substituent each independently selected from the substituent group A;

(b43) a benzothiazolyl group;

(b44) a substituted benzothiazolyl group having on the ring one to four substituents each independently selected from the substituent group A;

(b45) a thiazolopyridyl group;

(b46) a substituted thiazolopyridyl group having on the ring one to four substituents each independently selected from the substituent group A;

(b47) a quinolinyl group; or (b48) a substituted quinolinyl group having on the ring one to six substituents each independently selected from the substituent group A, $R^5$ represents (i1) a $(C_1-C_6)$alkyl group, and the substituent group A consists of (e1) a halogen atom;

(e2) a cyano group;

(e6) a $(C_1-C_6)$alkyl group;

(e9) a $(C_1-C_6)$alkoxy group;

(e11) a $(C_1-C_6)$alkylthio group;

(e12) a $(C_1-C_6)$alkylsulfinyl group;

(e13) a $(C_1-C_6)$alkylsulfonyl group;

(e14) a halo$(C_1-C_6)$alkyl group;

(e17) a halo$(C_1-C_6)$alkoxy group;

(e19) a halo$(C_1-C_6)$alkylthio group;

(e21) a halo$(C_1-C_6)$alkylsulfonyl group;

(e32) a $(C_1-C_6)$alkoxycarbonyl group;

(e34) an N—$(C_1-C_6)$alkylaminosulfonyl group; and (e35) an N,N-di$(C_1-C_6)$alkylaminosulfonyl group.

13. A composition comprising the compound of claim 1, or salt thereof or N-oxide thereof as an active ingredient, wherein the composition is an insecticidal composition, agricultural and horticultural insecticide composition, animal ectoparasite control composition, or animal endoparasite control composition.

14. A method of using an insecticidal agent, comprising applying an effective amount of the insecticidal agent according to claim 13 to a plant or soil.

15. A method of controlling insect infestation in a plant or soil, the method comprising applying an effective amount of the compound or salt thereof or N-oxide thereof according to claim 2 to said plant or soil.

16. A method for controlling animal ectoparasites, comprising orally or parenterally administering, to an animal in need thereof, an effective amount of the compound or a salt thereof according to claim 1 or an N-oxide as an active ingredient.

17. A method for controlling animal endoparasites, comprising orally or parenterally administering, to an animal in need thereof, an effective amount of the compound or a salt thereof according to claim 1 or an N-oxide as an active ingredient.

* * * * *